(12) United States Patent  
Choi et al.

(10) Patent No.: US 11,656,197 B2  
(45) Date of Patent: May 23, 2023

(54) SOLID STATE SEQUENCING DEVICES COMPRISING TWO DIMENSIONAL LAYER MATERIALS

(71) Applicant: Roswell Biotechnologies, Inc., San Diego, CA (US)

(72) Inventors: Chulmin Choi, San Diego, CA (US); Sungho Jin, San Diego, CA (US); Barry L. Merriman, San Diego, CA (US); Paul Mola, San Diego, CA (US); Tim Geiser, San Diego, CA (US)

(73) Assignee: Roswell ME Inc., San Diego, CA (US)

( * ) Notice: Subject to any disclaimer, the term of this patent is extended or adjusted under 35 U.S.C. 154(b) by 0 days.

(21) Appl. No.: 16/479,257

(22) PCT Filed: Nov. 22, 2017

(86) PCT No.: PCT/US2017/063105  
§ 371 (c)(1),  
(2) Date: Jul. 19, 2019

(87) PCT Pub. No.: WO2018/136148  
PCT Pub. Date: Jul. 26, 2018

(65) Prior Publication Data  
US 2019/0383770 A1  Dec. 19, 2019

Related U.S. Application Data

(60) Provisional application No. 62/448,078, filed on Jan. 19, 2017.

(51) Int. Cl.  
*G01N 27/414* (2006.01)  
*C12Q 1/6869* (2018.01)  
*G01N 27/447* (2006.01)

(52) U.S. Cl.  
CPC ....... *G01N 27/4145* (2013.01); *C12Q 1/6869* (2013.01); *G01N 27/44791* (2013.01)

(58) Field of Classification Search  
CPC ......... G01N 27/4145; G01N 27/44791; G01N 27/414; G01N 33/48721; C12Q 1/6869;  
(Continued)

(56) References Cited

U.S. PATENT DOCUMENTS 4,923,586 A  5/1990  Katayama et al.  
5,082,627 A  1/1992  Stanbro  
(Continued)

FOREIGN PATENT DOCUMENTS

CN  101231287  7/2008  
CN  102706940  10/2012  
(Continued)

OTHER PUBLICATIONS

Liu et al. ACS Nano, Feb. 18, 2014, vol. 8 pp. 2504-2511, entire document. (Year: 2014).*  
(Continued)

*Primary Examiner* — Benjamin R Whatley  
*Assistant Examiner* — Jacqueline Brazin  
(74) *Attorney, Agent, or Firm* — Spectrum IP Law Group LLC

(57) ABSTRACT

A sequencing device is disclosed. The sequence device includes an array of conducting electrode pairs, each pair of electrodes comprising a source and a drain electrode arrangement separated by a nanogap, the electrode array deposited and patterned on a dielectric substrate; at least one transition metal dichalcogenide (TMD) layer disposed on each pair of electrodes, wherein the TMD layer connects each source and drain electrode within each pair, and bridges each nanogap of each pair of electrodes; and a dielectric masking layer disposed on the TMD layer and comprising at  
(Continued)

least one opening that defines an exposed TMD region, wherein the at least one opening is sized so as to allow a single biomolecule to fit therein and to attach on to the exposed TMD region. In embodiments of the disclosure, the TMD layer be a defective TMD layer.

22 Claims, 33 Drawing Sheets

(58) Field of Classification Search
CPC .... C12Q 1/527; C12Q 1/68; C12Q 2565/607; B82Y 5/00; B82Y 15/00
USPC .................................................... 422/82.01
See application file for complete search history.

(56) References Cited

U.S. PATENT DOCUMENTS

| | | |
|---|---|---|
| 5,194,133 A | 3/1993 | Clark et al. |
| 5,366,140 A | 11/1994 | Koskenmaki et al. |
| 5,414,588 A | 5/1995 | Barbee, Jr. |
| 5,486,449 A | 1/1996 | Honso et al. |
| 5,532,128 A | 7/1996 | Eggers et al. |
| 5,583,359 A | 12/1996 | Ng et al. |
| 5,639,507 A | 6/1997 | Galvagni et al. |
| 5,646,420 A | 7/1997 | Yamashita |
| 5,767,687 A | 6/1998 | Geist |
| 5,871,918 A | 2/1999 | Thorp et al. |
| 5,881,184 A | 3/1999 | Guidash |
| 5,965,452 A | 10/1999 | Kovacs |
| 5,982,018 A | 11/1999 | Wark |
| 6,051,380 A | 4/2000 | Sosnowski et al. |
| 6,060,023 A | 5/2000 | Maracas |
| 6,094,335 A | 7/2000 | Early |
| 6,110,354 A | 8/2000 | Saban |
| 6,123,819 A | 9/2000 | Peeters |
| 6,144,023 A | 11/2000 | Clerc |
| 6,238,927 B1 | 5/2001 | Abrams et al. |
| 6,440,662 B1 | 8/2002 | Gerwen et al. |
| 6,464,889 B1 | 10/2002 | Lee et al. |
| 6,506,564 B1 | 1/2003 | Mirkin et al. |
| 6,537,747 B1 | 3/2003 | Mills, Jr. et al. |
| 6,670,131 B2 | 12/2003 | Hashimoto |
| 6,673,533 B1 | 1/2004 | Wohlstadter et al. |
| 6,716,620 B2 | 4/2004 | Bashir et al. |
| 6,749,731 B2 | 6/2004 | Kobori |
| 6,762,050 B2 | 7/2004 | Fukushima et al. |
| 6,764,745 B1 | 7/2004 | Karasawa et al. |
| 6,790,341 B1 | 9/2004 | Saban |
| 6,824,974 B2 | 11/2004 | Pisharody et al. |
| 6,861,224 B2 | 3/2005 | Fujita et al. |
| 6,916,614 B1 | 7/2005 | Takenaka et al. |
| 6,958,216 B2 | 10/2005 | Kelley |
| 7,015,046 B2 | 3/2006 | Wohlstadter et al. |
| 7,075,428 B1 | 7/2006 | Oleynik |
| 7,169,272 B2 | 1/2007 | Fritsch et al. |
| 7,183,055 B2 | 2/2007 | Van Der Weide |
| 7,189,435 B2 | 3/2007 | Tuominen et al. |
| 7,202,480 B2 | 4/2007 | Yokoi et al. |
| 7,208,077 B1 | 4/2007 | Albers et al. |
| 7,276,206 B2 | 10/2007 | Augustine et al. |
| 7,399,585 B2 | 7/2008 | Gau |
| 7,432,120 B2 | 10/2008 | Mascolo et al. |
| 7,470,533 B2 | 12/2008 | Xu et al. |
| 7,507,320 B2 | 3/2009 | Hwang et al. |
| 7,531,120 B2 | 5/2009 | Van Rijn et al. |
| 7,579,823 B1 | 8/2009 | Ayliffe |
| 7,691,433 B2 | 4/2010 | Kronholz et al. |
| 7,785,785 B2 | 8/2010 | Pourmand et al. |
| 7,834,344 B2 | 11/2010 | Mascolo et al. |
| 7,851,045 B2 | 12/2010 | Gandon et al. |
| 7,886,601 B2 | 2/2011 | Merassi et al. |
| 7,901,629 B2 | 3/2011 | Calatzis et al. |
| 7,943,394 B2 | 5/2011 | Flandre et al. |
| 8,241,508 B2 | 8/2012 | D'Urso |
| 8,313,633 B2 | 11/2012 | Li et al. |
| 8,351,181 B1 | 1/2013 | Ahn |
| 8,591,816 B2 | 11/2013 | Calatzis et al. |
| 8,652,768 B1 | 2/2014 | Huber et al. |
| 8,753,893 B2 | 6/2014 | Liu et al. |
| 8,927,464 B2 | 1/2015 | Aizenberg et al. |
| 8,940,663 B2 | 1/2015 | Iqbal et al. |
| 9,070,733 B2 | 6/2015 | Rajagopal et al. |
| 9,108,880 B2 | 8/2015 | Jin et al. |
| 9,139,614 B2 | 9/2015 | Medintz et al. |
| 9,306,164 B1 | 4/2016 | Chang et al. |
| 9,829,456 B1 | 11/2017 | Merriman et al. |
| 9,956,743 B2 | 5/2018 | Jin et al. |
| 10,036,064 B2 | 7/2018 | Merriman et al. |
| 10,125,420 B2 | 11/2018 | Jin et al. |
| 10,151,722 B2 | 12/2018 | Jin et al. |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,648,941 B2 | 5/2020 | Merriman et al. |
| 10,712,334 B2 | 7/2020 | Choi et al. |
| 2002/0022223 A1 | 2/2002 | Connolly |
| 2002/0090649 A1 | 7/2002 | Chan et al. |
| 2002/0137083 A1 | 9/2002 | Kobori et al. |
| 2002/0138049 A1 | 9/2002 | Allen et al. |
| 2002/0142150 A1 | 10/2002 | Baumann et al. |
| 2002/0142477 A1 | 10/2002 | Lewis et al. |
| 2002/0172963 A1 | 11/2002 | Kelley et al. |
| 2002/0184939 A1 | 12/2002 | Yadav |
| 2003/0025133 A1 | 2/2003 | Brousseau |
| 2003/0040000 A1 | 2/2003 | Connolly et al. |
| 2003/0040173 A1 | 2/2003 | Fonash et al. |
| 2003/0064390 A1 | 4/2003 | Schülein et al. |
| 2003/0087296 A1 | 5/2003 | Fujita et al. |
| 2003/0109031 A1 | 6/2003 | Chafin et al. |
| 2003/0141189 A1 | 7/2003 | Lee et al. |
| 2003/0141276 A1 | 7/2003 | Lee |
| 2003/0186263 A1 | 10/2003 | Frey et al. |
| 2003/0224387 A1 | 12/2003 | Kunwar et al. |
| 2004/0014106 A1 | 1/2004 | Patno et al. |
| 2004/0023253 A1 | 2/2004 | Kunwar et al. |
| 2004/0038090 A1 | 2/2004 | Faris |
| 2004/0048241 A1 | 3/2004 | Freeman et al. |
| 2004/0063100 A1 | 4/2004 | Wang |
| 2004/0086929 A1 | 5/2004 | Weide et al. |
| 2004/0096866 A1 | 5/2004 | Hoffman et al. |
| 2004/0012161 A1 | 6/2004 | Chiu |
| 2004/0146863 A1 | 7/2004 | Pisharody et al. |
| 2004/0209355 A1 | 10/2004 | Edman et al. |
| 2004/0209435 A1 | 10/2004 | Patridge et al. |
| 2004/0229247 A1 | 11/2004 | DeBoer et al. |
| 2004/0235016 A1 | 11/2004 | Hamers |
| 2004/0248282 A1 | 12/2004 | Sobha |
| 2005/0029227 A1 | 2/2005 | Chapman |
| 2005/0067086 A1 | 3/2005 | Ito et al. |
| 2005/0074911 A1 | 4/2005 | Kornilovich et al. |
| 2005/0151541 A1 | 7/2005 | Brinz et al. |
| 2005/0156157 A1 | 7/2005 | Parsons et al. |
| 2005/0164371 A1 | 7/2005 | Arinaga |
| 2005/0172199 A1 | 8/2005 | Miller et al. |
| 2005/0181195 A1 | 8/2005 | Dubrow |
| 2005/0221473 A1 | 10/2005 | Dubin et al. |
| 2005/0227373 A1 | 10/2005 | Flandre et al. |
| 2005/0247573 A1 | 11/2005 | Nakamura et al. |
| 2005/0285275 A1 | 12/2005 | Son |
| 2005/0287548 A1 | 12/2005 | Bao et al. |
| 2005/0287589 A1 | 12/2005 | Connolly |
| 2006/0003482 A1 | 1/2006 | Chinthakindi et al. |
| 2006/0019273 A1 | 1/2006 | Connolly et al. |
| 2006/0024504 A1 | 2/2006 | Nelson et al. |
| 2006/0024508 A1 | 2/2006 | D'Urso et al. |
| 2006/0029808 A1 | 2/2006 | Zhai et al. |
| 2006/0051919 A1 | 3/2006 | Mascolo et al. |
| 2006/0051946 A1 | 3/2006 | Mascolo et al. |
| 2006/0105449 A1 | 5/2006 | Larmer et al. |
| 2006/0105467 A1 | 5/2006 | Niksa et al. |
| 2006/0128239 A1 | 5/2006 | Nun et al. |
| 2006/0147983 A1 | 7/2006 | O'uchi |

(56) References Cited

U.S. PATENT DOCUMENTS

| | | |
|---|---|---|
| 2006/0154489 A1 | 7/2006 | Tornow |
| 2006/0275853 A1 | 12/2006 | Matthew et al. |
| 2007/0026193 A1 | 2/2007 | Luzinov et al. |
| 2007/0048748 A1 | 3/2007 | Williams et al. |
| 2007/0140902 A1 | 6/2007 | Calatzis et al. |
| 2007/0148815 A1 | 6/2007 | Chao et al. |
| 2007/0186628 A1 | 8/2007 | Curry et al. |
| 2007/0184247 A1 | 9/2007 | Simpson et al. |
| 2007/0207487 A1 | 9/2007 | Emig et al. |
| 2007/0231542 A1 | 10/2007 | Deng |
| 2008/0012007 A1 | 1/2008 | Li et al. |
| 2008/0098815 A1 | 5/2008 | Merassi et al. |
| 2008/0149479 A1 | 6/2008 | Olofsson et al. |
| 2008/0199657 A1 | 8/2008 | Capron et al. |
| 2008/0199659 A1 | 8/2008 | Zhao |
| 2009/0006284 A1 | 1/2009 | Liu et al. |
| 2009/0011222 A1 | 1/2009 | Xiu et al. |
| 2009/0017571 A1 | 1/2009 | Nuckolls |
| 2009/0020428 A1 | 1/2009 | Levitan |
| 2009/0027036 A1 | 1/2009 | Nuckolls et al. |
| 2009/0062684 A1 | 3/2009 | Gregersen et al. |
| 2009/0152109 A1 | 6/2009 | Whitehead et al. |
| 2009/0162927 A1 | 6/2009 | Naaman et al. |
| 2009/0170716 A1* | 7/2009 | Su .................... C12Q 1/6869 506/9 |
| 2009/0178935 A1 | 7/2009 | Reymond et al. |
| 2009/0295372 A1 | 12/2009 | Krstic et al. |
| 2009/0297913 A1 | 12/2009 | Zhang et al. |
| 2009/0306578 A1 | 12/2009 | Sivan et al. |
| 2009/0324308 A1 | 12/2009 | Law et al. |
| 2010/0038342 A1 | 2/2010 | Lim et al. |
| 2010/0044212 A1 | 2/2010 | Kim et al. |
| 2010/0055397 A1 | 3/2010 | Kurihara et al. |
| 2010/0132771 A1 | 6/2010 | Lu |
| 2010/0142259 A1 | 6/2010 | Drndic et al. |
| 2010/0149530 A1 | 6/2010 | Tomaru |
| 2010/0167938 A1 | 7/2010 | Su et al. |
| 2010/0184062 A1 | 7/2010 | Steinmueller-Nethl et al. |
| 2010/0188109 A1 | 7/2010 | Edel et al. |
| 2010/0194409 A1 | 8/2010 | Gao et al. |
| 2010/0201381 A1 | 8/2010 | Iqbal et al. |
| 2010/0206367 A1 | 8/2010 | Jeong et al. |
| 2010/0227416 A1 | 9/2010 | Koh et al. |
| 2010/0280397 A1 | 11/2010 | Feldman et al. |
| 2010/0285275 A1 | 11/2010 | Baca et al. |
| 2010/0285601 A1 | 11/2010 | Kong et al. |
| 2010/0288543 A1 | 11/2010 | Hung et al. |
| 2010/0300899 A1 | 12/2010 | Levine et al. |
| 2011/0056845 A1 | 3/2011 | Stellacci |
| 2011/0065588 A1 | 3/2011 | Su et al. |
| 2011/0076783 A1 | 3/2011 | Liu et al. |
| 2011/0091787 A1 | 4/2011 | McGrath et al. |
| 2011/0160077 A1 | 6/2011 | Chaisson et al. |
| 2011/0166034 A1 | 7/2011 | Kwong et al. |
| 2011/0217763 A1 | 9/2011 | Rasooly et al. |
| 2011/0227558 A1 | 9/2011 | Mannion et al. |
| 2011/0229667 A1 | 9/2011 | Jin et al. |
| 2011/0233075 A1 | 9/2011 | Soleymani et al. |
| 2011/0248315 A1 | 10/2011 | Nam et al. |
| 2011/0287956 A1 | 11/2011 | Iqbal et al. |
| 2011/0291673 A1 | 12/2011 | Shibata et al. |
| 2011/0306039 A1* | 12/2011 | Chiou .................. G01N 21/648 435/6.1 |
| 2011/0311853 A1 | 12/2011 | Fratti |
| 2011/0312529 A1 | 12/2011 | He et al. |
| 2012/0060905 A1 | 3/2012 | Fogel et al. |
| 2012/0122715 A1 | 5/2012 | Gao et al. |
| 2012/0220046 A1 | 8/2012 | Chao |
| 2012/0258870 A1 | 10/2012 | Schwartz et al. |
| 2012/0286332 A1 | 11/2012 | Rothberg et al. |
| 2012/0309106 A1 | 12/2012 | Eichen et al. |
| 2013/0049158 A1 | 2/2013 | Hong et al. |
| 2013/0071289 A1 | 3/2013 | Knoll |
| 2013/0108956 A1 | 5/2013 | Lu et al. |
| 2013/0109577 A1 | 5/2013 | Korlach et al. |
| 2013/0162276 A1 | 6/2013 | Lee et al. |
| 2013/0183492 A1 | 7/2013 | Lee et al. |
| 2013/0214875 A1 | 8/2013 | Duncan et al. |
| 2013/0239349 A1 | 9/2013 | Knights et al. |
| 2013/0245416 A1 | 9/2013 | Yarmush et al. |
| 2013/0273340 A1 | 10/2013 | Neretina et al. |
| 2013/0281325 A1 | 10/2013 | Elibol et al. |
| 2013/0331299 A1 | 12/2013 | Reda et al. |
| 2014/0001055 A1 | 1/2014 | Elibol et al. |
| 2014/0011013 A1 | 1/2014 | Jin |
| 2014/0018262 A1 | 1/2014 | Reda et al. |
| 2014/0027775 A1* | 1/2014 | Quick ............... H01L 21/02568 257/53 |
| 2014/0048776 A1 | 2/2014 | Huang et al. |
| 2014/0054788 A1 | 2/2014 | Majima et al. |
| 2014/0057283 A1 | 2/2014 | Wang et al. |
| 2014/0061049 A1 | 3/2014 | Lo et al. |
| 2014/0079592 A1 | 3/2014 | Chang et al. |
| 2014/0170567 A1 | 6/2014 | Sakamoto et al. |
| 2014/0174927 A1 | 6/2014 | Bashir et al. |
| 2014/0197459 A1* | 7/2014 | Kis .................. H01L 29/40111 257/194 |
| 2014/0218637 A1 | 8/2014 | Gao et al. |
| 2014/0235493 A1 | 8/2014 | Zang et al. |
| 2014/0253827 A1 | 9/2014 | Gao et al. |
| 2014/0284667 A1 | 9/2014 | Basker et al. |
| 2014/0320849 A1 | 10/2014 | Chou et al. |
| 2014/0367749 A1 | 12/2014 | Bai et al. |
| 2014/0377900 A1 | 12/2014 | Yann et al. |
| 2015/0005188 A1 | 1/2015 | Levner et al. |
| 2015/0017655 A1 | 1/2015 | Huang et al. |
| 2015/0049332 A1 | 2/2015 | Sun et al. |
| 2015/0057182 A1 | 2/2015 | Merriman et al. |
| 2015/0065353 A1 | 3/2015 | Turner et al. |
| 2015/0068892 A1 | 3/2015 | Ueno et al. |
| 2015/0077183 A1 | 3/2015 | Ciubotaru |
| 2015/0148264 A1 | 5/2015 | Esfandyarpour et al. |
| 2015/0177150 A1 | 6/2015 | Rothberg et al. |
| 2015/0191709 A1 | 7/2015 | Heron et al. |
| 2015/0263203 A1 | 9/2015 | Lewis et al. |
| 2015/0293025 A1 | 10/2015 | Ninomiya et al. |
| 2015/0294875 A1* | 10/2015 | Khondaker ....... H01L 21/02271 257/411 |
| 2015/0344945 A1 | 12/2015 | Mandell et al. |
| 2016/0017416 A1* | 1/2016 | Boyanov ............. C12Q 1/6825 506/4 |
| 2016/0045378 A1 | 2/2016 | Geloen |
| 2016/0155971 A1 | 6/2016 | Strachan et al. |
| 2016/0187282 A1 | 6/2016 | Gardner et al. |
| 2016/0265047 A1 | 9/2016 | van Rooyen et al. |
| 2016/0284811 A1* | 9/2016 | Yu ......................... H01L 29/786 |
| 2016/0290957 A1 | 10/2016 | Ram et al. |
| 2016/0319342 A1 | 11/2016 | Kawai et al. |
| 2016/0377564 A1 | 12/2016 | Carmignani et al. |
| 2017/0018626 A1* | 1/2017 | Hoffman ............... H01L 27/085 |
| 2017/0023512 A1 | 1/2017 | Cummins et al. |
| 2017/0037462 A1 | 2/2017 | Turner et al. |
| 2017/0038333 A1 | 2/2017 | Turner et al. |
| 2017/0043355 A1 | 2/2017 | Fischer |
| 2017/0044605 A1 | 2/2017 | Merriman |
| 2017/0131237 A1 | 5/2017 | Ikeda |
| 2017/0184542 A1 | 6/2017 | Chatelier et al. |
| 2017/0234825 A1 | 8/2017 | Elibol et al. |
| 2017/0240962 A1 | 8/2017 | Merriman |
| 2017/0288017 A1 | 10/2017 | Majima et al. |
| 2017/0332918 A1 | 11/2017 | Keane |
| 2018/0014786 A1 | 1/2018 | Keane |
| 2018/0031508 A1 | 2/2018 | Jin |
| 2018/0031509 A1 | 2/2018 | Jin |
| 2018/0045665 A1 | 2/2018 | Jin |
| 2018/0259474 A1 | 9/2018 | Jin |
| 2018/0297321 A1 | 10/2018 | Jin et al. |
| 2018/0305727 A1 | 10/2018 | Merriman |
| 2018/0340220 A1 | 11/2018 | Merriman |
| 2019/0004003 A1 | 1/2019 | Merriman |
| 2019/0033244 A1 | 1/2019 | Jin |
| 2019/0039065 A1 | 2/2019 | Choi |
| 2019/0041355 A1 | 2/2019 | Merriman |
| 2019/0041378 A1 | 2/2019 | Choi |

(56) References Cited

U.S. PATENT DOCUMENTS

| | | | |
|---|---|---|---|
| 2019/0094175 A1 | 3/2019 | Merriman | |
| 2019/0194801 A1 | 6/2019 | Jin et al. | |
| 2019/0355442 A1 | 11/2019 | Merriman et al. | |
| 2019/0376925 A1 | 12/2019 | Choi et al. | |
| 2019/0383770 A1 | 12/2019 | Choi et al. | |
| 2020/0157595 A1 | 5/2020 | Merriman et al. | |
| 2020/0217813 A1 | 7/2020 | Merriman et al. | |
| 2020/0242482 A1 | 7/2020 | Merriman et al. | |
| 2020/0277645 A1 | 9/2020 | Merriman et al. | |
| 2020/0385850 A1 | 12/2020 | Merriman et al. | |
| 2020/0385855 A1 | 12/2020 | Jin et al. | |
| 2020/0393440 A1 | 12/2020 | Jin et al. | |

FOREIGN PATENT DOCUMENTS

| | | |
|---|---|---|
| CN | 104685066 | 6/2015 |
| CN | 104703700 | 6/2015 |
| CN | 108027335 | 5/2018 |
| DE | 102012008375 | 10/2012 |
| DE | 102013012145 | 1/2015 |
| EP | 2053383 | 4/2009 |
| EP | 3403079 | 11/2018 |
| EP | 3408219 | 12/2018 |
| EP | 3408220 | 12/2018 |
| EP | 3414784 | 12/2018 |
| EP | 3420580 | 1/2019 |
| GB | 2485559 | 5/2012 |
| JP | 0233981 | 7/1990 |
| JP | 2008-258594 | 10/2008 |
| JP | 2018-522236 | 8/2018 |
| KR | 20070059880 | 6/2007 |
| KR | 20110104245 | 9/2011 |
| WO | 2001044501 | 6/2001 |
| WO | 2002049980 | 6/2002 |
| WO | 2001044501 A3 | 7/2002 |
| WO | 2002074985 | 9/2002 |
| WO | 2003042396 | 5/2003 |
| WO | 2003091458 A1 | 11/2003 |
| WO | 2004096986 | 11/2004 |
| WO | 2004099307 | 11/2004 |
| WO | 2004096986 A3 | 3/2005 |
| WO | 2005108612 | 11/2005 |
| WO | 2007054649 | 5/2007 |
| WO | 2007102960 | 9/2007 |
| WO | 2007126432 | 11/2007 |
| WO | 2007128965 | 11/2007 |
| WO | 2009003208 | 1/2009 |
| WO | 2009035647 | 3/2009 |
| WO | 2010022107 | 2/2010 |
| WO | 2012083249 | 6/2012 |
| WO | 2012087352 | 6/2012 |
| WO | 2012152056 | 11/2012 |
| WO | 2013096851 | 6/2013 |
| WO | 2014018630 A1 | 1/2014 |
| WO | 2014182630 | 7/2014 |
| WO | 2015167019 | 11/2015 |
| WO | 2015176990 | 11/2015 |
| WO | 2015188197 | 12/2015 |
| WO | 2016016635 | 2/2016 |
| WO | 2016100635 | 6/2016 |
| WO | 2016100637 | 6/2016 |
| WO | 2016196755 | 12/2016 |
| WO | 2016210386 | 12/2016 |
| WO | 2017027518 | 2/2017 |
| WO | 2017041056 | 3/2017 |
| WO | 2017042038 | 3/2017 |
| WO | 2017061129 | 4/2017 |
| WO | 2017123416 | 7/2017 |
| WO | 2017132567 | 8/2017 |
| WO | 2017132586 | 8/2017 |
| WO | 2017139493 | 8/2017 |
| WO | 2017147187 | 8/2017 |
| WO | 2017151680 | 9/2017 |
| WO | 2017184677 | 10/2017 |
| WO | 2018022799 | 2/2018 |
| WO | 2018026855 | 2/2018 |
| WO | 2018098286 | 5/2018 |
| WO | 2018132457 | 7/2018 |
| WO | 2018136148 | 7/2018 |
| WO | 2018200687 | 11/2018 |
| WO | 2018208505 | 11/2018 |
| WO | 2020210832 A1 | 10/2020 |
| WO | 2021226291 A1 | 11/2021 |
| WO | 2021237180 A1 | 11/2021 |
| WO | 2021237182 A1 | 11/2021 |
| WO | 2021262739 A1 | 12/2021 |
| WO | 2022051558 A1 | 3/2022 |

OTHER PUBLICATIONS

USPTO; Requirement for Restriction dated Nov. 2, 2011 in U.S. Appl. No. 12/667,583.
USPTO; Non-Final Office Action dated Sep. 28, 2018 in U.S. Appl. No. 12/667,583.
USPTO; Final Office Action dated Feb. 19, 2019 in U.S. Appl. No. 12/667,583.
USPTO; Non-Final Office Action dated Aug. 19, 2019 in U.S. Appl. No. 12/667,583.
USPTO; Requirement for Restriction dated Dec. 1, 2016 in U.S. Appl. No. 13/996,477.
USPTO; Non-Final Office Action dated May 5, 2017 in U.S. Appl. No. 13/996,477.
USPTO; Final Office Action dated Oct. 4, 2017 in U.S. Appl. No. 13/996,477.
USPTO; Notice of Allowance dated Jan. 3, 2018 in U.S. Appl. No. 13/996,477.
USPTO; Final Office Action dated Dec. 30, 2016 in U.S. Appl. No. 15/050,270.
USPTO; Advisory Action dated Mar. 14, 2017 in U.S. Appl. No. 15/050,270.
USPTO; Non-Final Office Action dated Sep. 29, 2017 in U.S. Appl. No. 15/050,270.
USPTO; Final Office Action dated Jul. 10, 2018 in U.S. Appl. No. 15/050,270.
USPTO; Advisory Action dated Sep. 26, 2018 in U.S. Appl. No. 15/050,270.
USPTO; Non-Final Office Action dated Feb. 26, 2019 in U.S. Appl. No. 15/050,270.
USPTO; Final Office Action dated Jul. 10, 2019 in U.S. Appl. No. 15/050,270.
USPTO; Notice of Allowance dated Jan. 6, 2020 in U.S. Appl. No. 15/050,270.
USPTO; Non-Final Office Action dated Oct. 19, 2016 in U.S. Appl. No. 15/220,307.
USPTO; Notice of Allowance dated Jul. 28, 2017 in U.S. Appl. No. 15/220,307.
USPTO; Requirement for Restriction dated Jan. 17, 2017 in U.S. Appl. No. 15/336,557.
USPTO; Non-Final Office Action dated May 16, 2017 in U.S. Appl. No. 15/336,557.
USPTO; Final Office Action dated Mar. 8, 2018 in U.S. Appl. No. 15/336,557.
USPTO; Notice of Allowance dated May 25, 2018 in U.S. Appl. No. 15/336,557.
USPTO; Non-Final Office Action dated Feb. 9, 2018 in U.S. Appl. No. 15/728,400.
USPTO; Final Office Action dated Jul. 10, 2018 in U.S. Appl. No. 15/728,400.
USPTO; Advisory Action dated Oct. 12, 2018 in U.S. Appl. No. 15/728,400.
USPTO; Advisory Action dated Nov. 14, 2018 in U.S. Appl. No. 15/728,400.
USPTO; Notice of Allowance dated Dec. 6, 2018 in U.S. Appl. No. 15/728,400.
USPTO; Non-Final Office Action dated Feb. 23, 2018 in U.S. Appl. No. 15/728,412.
USPTO; Notice of Allowance dated Sep. 12, 2018 in U.S. Appl. No. 15/728,412.

(56) References Cited

OTHER PUBLICATIONS

USPTO; Final Office Action dated Jun. 13, 2018 in U.S. Appl. No. 15/728,412.
USPTO; Non-Final Office Action dated Feb. 23, 2018 in U.S. Appl. No. 15/796,080.
USPTO; Final Office Action dated Jun. 14, 2018 in U.S. Appl. No. 15/796,080.
USPTO; Advisory Action dated Sep. 4, 2018 in U.S. Appl. No. 15/796,080.
USPTO; Notice of Allowance dated Oct. 11, 2018 in U.S. Appl. No. 15/796,080.
USPTO; Non-Final Office Action dated Mar. 7, 2019 in U.S. Appl. No. 15/944,356.
USPTO; Non-Final Office Action dated Sep. 4, 2018 in U.S. Appl. No. 15/979,135.
USPTO; Non-Final Office Action dated Nov. 30, 2018 in U.S. Appl. No. 15/979,135.
USPTO; Final Office Action dated Mar. 1, 2019 in U.S. Appl. No. 15/979,135.
USPTO; Advisory Action dated May 22, 2019 in U.S. Appl. No. 15/979,135.
USPTO; Non-Final Office Action dated Jun. 25, 2019 in U.S. Appl. No. 15/979,135.
USPTO; Notice of Allowance dated Dec. 11, 2019 in U.S. Appl. No. 15/979,135.
USPTO; Non-Final Office Action dated Aug. 22, 2019 in the U.S. Appl. No. 16/011,065.
USPTO; Final Office Action dated Mar. 6, 2020 in U.S. Appl. No. 16/011,065.
USPTO; Requirement for Restriction dated Oct. 15, 2018 in U.S. Appl. No. 16/015,028.
USPTO; Non-Final Office Action dated Dec. 26, 2018 in U.S. Appl. No. 16/015,028.
USPTO; Final Office Action dated Apr. 15, 2019 in U.S. Appl. No. 16/015,028.
USPTO; Non-Final Office Action dated Jul. 30, 2019 in the U.S. Appl. No. 16/015,028.
USPTO; Notice of Allowance dated Nov. 8, 2019 in U.S. Appl. No. 16/015,028.
USPTO; Requirement for Restriction dated Dec. 17, 2018 in U.S. Appl. No. 16/015,049.
USPTO; Non-Final Office Action dated Mar. 6, 2019 in U.S. Appl. No. 16/015,049.
USPTO; Final Office Action dated Jun. 19, 2019 in U.S. Appl. No. 16/015,049.
USPTO; Non-Final Office Action dated Nov. 5, 2019 in U.S. Appl. No. 16/015,049.
USPTO; Notice of Allowance dated Feb. 20, 2020 in U.S. Appl. No. 16/015,049.
USPTO; Non-Final Office Action dated Apr. 13, 2020 in U.S. Appl. No. 16/070,133.
USPTO; Restriction Requirement dated Sep. 19, 2019 in U.S. Appl. No. 16/073,706.
USPTO; Non-Final Office Action dated Oct. 24, 2019 in U.S. Appl. No. 16/073,706.
USPTO; Non-Final Office Action dated Jan. 10, 2020 in U.S. Appl. No. 16/076,673.
USPTO; Non-Final Office Action dated Feb. 1, 2019 in U.S. Appl. No. 16/152,190.
USPTO; Notice of Allowance dated May 30, 2019, in U.S. Appl. No. 16/152,190.
USPTO; Restriction Requirement dated May 29, 2019 in U.S. Appl. No. 16/250,929.
USPTO; Notice of Allowance dated Oct. 23, 2019 in U.S. Appl. No. 16/250,929.
USPTO; Restriction Requirement dated Apr. 8, 2020 in U.S. Appl. No. 16/479,257.
PCT; International Search Report and Written Opinion dated Nov. 29, 2012 in Application No. PCT/US2011/001995.
PCT; International Search Report and Written Opinion dated Apr. 13, 2018 in Application No. PCT/US2018/013140.
PCT; International Search Report and Written Opinion dated Jan. 27, 2017 in Application No. PCT/US2017/015437.
PCT; International Search Report and Written Opinion dated Jan. 27, 2017 in Application No. PCT/US2017/015465.
PCT; International Search Report and Written Opinion dated Jul. 26, 2017 in Application No. PCT/US2017/017231.
PCT; International Search Report and Written Opinion dated May 25, 2017 in Application No. PCT/US2017/018950.
PCT; International Search Report and Written Opinion dated Jul. 20, 2018 in Application No. PCT/US2018/029382.
PCT; International Search Report and Written Opinion dated Jul. 20, 2018 in Application No. PCT/US2018/029393.
PCT; International Search Report and Written Opinion dated Sep. 27, 2016 in Application No. PCT/US2016/039446.
PCT; International Search Report and Written Opinion dated Nov. 22, 2017 in Application No. PCT/US2017/044023.
PCT; International Search Report and Written Opinion dated Dec. 26, 2017 in Application No. PCT/US2017/044965.
PCT; International Search Report and Written Opinion received Nov. 9, 2018 in Application No. PCT/US2018/048873.
PCT; International Search Report and Written Opinion dated Apr. 8, 2010 in Application No. PCT/US2009/054235.
PCT; International Search Report and Written Opinion dated Jan. 18, 2019 in Application No. PCT/US2018/055264.
PCT; International Search Report and Written Opinion dated Mar. 12, 2018 in Application No. PCT/US2017/063025.
PCT; International Search Report and Written Opinion dated Mar. 7, 2018 in Application No. PCT/US2017/063105.
PCT; International Search Report and Written Opinion dated Apr. 18, 2017 in Application No. PCT/US2016/068922.
CN; Notice of the First Office Action dated Sep. 2, 2019 in Chinese Application No. 201680049272.8.
CN; Notice of the First Office Action dated Sep. 30, 2019 in Chinese Application No. 201780020478.2.
EP; European Search Report dated Jan. 30, 2019 in Application No. 16815467.2.
EP; European Search Report dated Aug. 2, 2019 in Application No. 16885434.7.
EP; European Search Report dated Jan. 29, 2020 in Application No. 17745013.7.
EP; European Search Report dated Aug. 2, 2019 in Application No. 17745026.9.
EP; European Search Report dated Jan. 29, 2020 in Application No. 17750776.1.
EP; European Search Report dated Oct. 24, 2019 in Application No. 17757146.0.
EP; European Search Report dated Mar. 6, 2020 in Application No. 17835231.6.
EP; European Search Report dated Feb. 7, 2020 in Application No. 17837566.3.
Ahn et al., "Electrical Immunosensor Based on a Submicron-Gap Interdigitated Electrode and Gold Enhancement," Biosensors and Bioelectronics, vol. 26, pp. 4690-4696, (2011).
Alayo et al., "Gold Interdigitated Nanoelectrodes as a Sensitive Analytical Tool for Selective Detection of Electroactive Species via Redox Cycling," Microchim Acta, vol. 183, pp. 1633-1639, (2016).
Antibody Structure Downloaded from https://absoluteantibody.com/antibody-resources/antibody-overview/antibody-structure/ (Mar. 1, 2019).
Bai et al., "Review: Gas Sensors Based on Conducting Polymers," Sensors, vol. 7, pp. 267-307, (2007).
Bailey et al., "DNA-Encoded Antibody Libraries: A Unified Platform for Multiplexed Cell Sorting and Detection of Genes and Proteins," Journal of American Chemical Society, vol. 129, pp. 1959-1967, (2007).
Bechelany et al. "Synthesis Mechanisms of Organized Nanoparticles: Influence of Annealing Temperature and Atmosphere," Crystal Growth and Design, vol. 10, pp. 587-596 (Oct. 21, 2010).
Berdat et al., "Label-Free Detection of DNA with Interdigitated Micro-Electrodes in a Fluidic Cell," Lab on a Chip, vol. 8, pp. 302-308, (2008).

(56) References Cited

OTHER PUBLICATIONS

Bhura, "3D Interdigitated Electrode Array (IDEA) Biosensor for Detection of Serum Biomarker," Master Thesis, Portland State University, 68 Pages, (2011).
Blossey, R., "Self-Cleaning Surfaces—Virtual Realities," Nature Materials, vol. 2(5), pp. 301-306, (May 2006).
Bonilla et al., "Electrical Readout of Protein Microarrays on Regular Glass Slides," Analytical Chemistry, vol. 83, pp. 1726-1731, (2011).
Botsialas et al., "A Miniaturized Chemocapacitor System for the Detection of Volatile Organic Compounds," Sensors and Actuators B, Chemical, vol. 177, pp. 776-784, (2013).
Branagan et al., "Enhanced Mass Transport of Electroactive Species to Annular Nanoband Electrodes Embedded in Nanocapillary Array Membranes," Journal of the American Chemical Society, vol. 134, pp. 8617-8624, (2012).
Braun et al., "DNA-Templated Assembly and Electrode Attachment of a Conducting Silver Wire," Letters to Nature, vol. 391(6669), pp. 775-778, (Feb. 1998).
Briglin et al., "Exploitation of Spatiotemporal Information and Geometric Optimization of Signal/Noise Performance Using Arrays of Carbon Black-Polymer Composite Vapor Detectors," Sensors and Actuators B, vol. 82, pp. 54-74, (2002).
Cassie, A.B.D. et al., "Wettability of Porous Surfaces," Transitions of the Faraday Society, vol. 40, pp. 546-551, (Jan. 1944) (Abstract Only).
Cerofolini et al., "A Hybrid Approach to Nanoelectronics: A Hybrid Approach to Nanoelectrics," Nanotechnology, Institute of Physics Publishing, GB, vol. 16, No. 8, pp. 1040-1047 (2005).
Chen, X. et al., "Electrical Nanogap Devices for Biosensing," Materials Today, vol. 13, pp. 28-41, (Nov. 2010).
Chen et al., "Electrochemical Approach for Fabricating Nanogap Electrodes with Well Controllable Separation," Applied Physics Letters, vol. 86, pp. 123105.1-123105.3, (2005).
Chen et al., "Fabrication of Submicron-Gap Electrodes by Silicon Volume Expansion for DNA-Detection," Sensors and Actuators A, vol. 175, pp. 73-77, (2012).
Choi, J. E. et al., "Fabrication of Microchannel with 60 Electrodes and Resistance Measurement," Flow Measurement and Instrumentation, vol. 21, pp. 178-183, (Sep. 2010) (Abstract Only).
Choi Y.S. et al., "Hybridization by an Electroatomical Genome on Detection on Using an Indicator-Free DNA on a Microelectrode-Array DNA Chip," Bulletin of the Korean Chemistry Society, vol. 26, pp. 379-383, (2005).
Choi, C. et al., "Strongly Superhydrophobic Silicon Nanowires by Supercritical CO2 Drying," Electronic Materials Letters, vol. 6 (2), pp. 59-64, (Jun. 2010).
Church et al., "Next-Generation Digital Information Storage in DNA," Science, vol. 337(6102), p. 6102, (Sep. 28, 2012).
Cosofret et al., "Microfabricated Sensor Arrays Sensitive to pH and K+ for Ionic Distribution Measurements in the Beating Heart," Analytical Chemistry, vol. 67, pp. 1647-1653, (1995).
Coulson S.R. et al., "Super-Repellent Composite Fluoropolymer Surfaces," The Journal of Physical Chemistry B., vol. 104(37), pp. 8836-8840, (Aug. 2000).
Dickey et al., "Electrically Addressable Parallel Nanowires with 30 NM Spacing from Micromolding and Nanoskiving," Nano Letters, vol. 8(12), pp. 4568-4573, (2008).
Fan et al., "Detection of MicroRNAs Using Target-Guided Formation of Conducting Polymer Nanowires in Nanogaps," Journal of the American Chemical Society, vol. 129, pp. 5437-5443, (2007).
Fink et al. "Electrical Conduction Through DNA Molecules," Nature, vol. 398, pp. 407-410 (Jan. 20, 1999).
Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-5523, (May 10, 2016).
Gapin, A.I. et al., "CoPt Patterned Media in Anodized Aluminum Oxide Templates," Journal of Applied Physics, vol. 99(8), pp. 08G902 (1-3), (Apr. 2006).

Ghindilis, A. et al., "Real Time Biosensor Platforms Fully Integrated Device for Impedimetric Assays," ECS Transactions, vol. 33, pp. 59-68, (2010).
Guo et al., "Conductivity of a single DNA duplex bridging a carbon nanotube gap," Nat. Nanotechnol., vol. 3, No. 3, pp. 1-12 (2008).
Han, "Energy Band Gap Engineering of Graphene Nanoribbons," Physical Review Letters, vol. 98, pp. 1-7, (May 16, 2007).
Han et al., "Redox Cycling in Nanopore-Confined Recessed Dual-Ring Electrode Arrays," Journal of Physical Chemistry C, vol. 120, pp. 20634-20641, (2016).
Hanief, Topic, Pineda-Vargas, "Solid State Dewetting of Continuous Thin Platinum Coatings," Nuclear Instruments and Methods in Physics Research, vol. 363, pp. 173-176, (2015).
Hashioka et al., "Deoxyribonucleic Acid Sensing Device with 40-NM-Gap-Electrodes Fabricated by Low-Cost Conventional Techniques," Applied Physics Letters, vol. 85(4), p. 687-688, (Jul. 2004).
He et al., "Electromechanical Fabrication of Atomically Thin Metallic Wires and Electrodes Separated with Molecular-Scale Gaps," Journal of Electroanalytical Chemistry, vol. 522, pp. 167-172, (Jan. 2002).
Heerema et al., "Graphene Nanodevices for DNA Sequencing," Nature Nanotechnology, vol. 11, pp. 127-136, (Feb. 3, 2016).
Henry et al., "Microcavities Containing Individually Addressable Recessed Microdisk and Tubular Nanoband Electrodes," Journal of The Electrochemical Society, vol. 146(9), pp. 3367-3373, (1999).
Hwang et al., "Electrical Transport Through 60 Base Pairs of Poly (dG)-Poly (dC) DNA Molecules," Applied Physics Letters, vol. 81(6), p. 1134-1136, (Aug. 2002).
Ino et al., "Addressable Electrode Array Device with IDA Electrodes for High-Throughput Detection," Lab on a Chip, vol. 11, p. 385-388, (2011).
Ino et al., "Local Redox-Cycling-Based Electrochemical Chip Device with Seep Microwells for Evaluation of Embryoid Bodies," Angewandte Chemie International Edition, vol. 51, pp. 6648-6652, (2012).
Iqbal et al., "Direct Current Electrical Characterization of ds-DNA in Nanogap Junctions," Applied Physics Letter, vol. 86, p. 153901-1-153901-3, (Apr. 2005).
Javey et al., "Layer-By-Layer Assembly of Nanowires for Three-Dimensional, Multifunctional Electronics," Nano Letters, vol. 7, pp. 773-777, (2007).
Khawli et al., "Charge Variants in IgGI-Isolation, Characterization, In Vitro Binding Properties and Pharmacokinetics in Rats," Landes Bioscience, vol. 2(6), pp. 613-623, (2010).
Kim, J. Y. et al., "Optically Transparent Glass with Vertically Aligned Surface Al2O3 Nanowires Having Superhydrophobic Characteristics," NANO: Brief Reports and Reviews, vol. 5(2), pp. 89-95, (Apr. 2010) (Abstract Only).
Kim et al., "Rapid Fabrication of Uniformly Sized Nanopores and Nanopore Arrays for Parallel DNA Analysis," Advances Materials, vol. 18, pp. 3149-3153, (Dec. 4, 2006).
Kitsara et al., "Single Chip Interdigitated Electrode Capacitive Chemical Sensor Arrays," Sensors and Actuators B, vol. 127, pp. 186-192, (2007).
Kitsara et al., "Small-Volume Multiparametric Electrochemical Detection at Low Cost Polymeric Devices Featuring Nanoelectrodes," SPIE, vol. 9518, 9 Pages, (2015).
Kraft, "Doped Diamond: A Compact Review on a New, Versatile Electrode Material," International Journal of Electrochemistry, vol. 2, pp. 355-385, (May 2007).
Kumar et al., "Terminal Phosphate Labeled Nucleotides: Synthesis, Applications and Linker Effect on Incorporation by DNA Polymerases," Nucleosides, Nucleotides and Nucleic Acids, Taylor and Francis, vol. 24, No. 5-7, pp. 401-408 (2005).
Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).
Lin et al., "An Addressable Microelectrode Array for Electrichemical Detection," Analytical Chemistry, vol. 80, pp. 6830-6833, (2008).
Liu et al., "Atomically Thin Molybdenum Disulfide Nanopores with High Sensitivity for DNA Translocation," ACS Nano, vol. 8, pp. 2504-2511, (Feb. 18, 2014).

(56) References Cited

OTHER PUBLICATIONS

Liu et al., "An Enzyme-Based E-DNA Sensor for Sequence-Specific Detection of Femtomolar DNA Targets," J. Am. Chem. Soc., vol. 130(21), pp. 6820-6825, (2008).
Liu et al., "Controllable Nanogap Fabrication on Microchip by Chronopotentiometry," Electrochimica Acta, vol. 50, pp. 3041-3047, (2005).
MacNaughton et al., "High-Throughput Heterogeneous Integration of Diverse Nanomaterials on a Single Chip for Sensing Applications," PLOS One, vol. 9(10), e111377, 7 Pages, (2014).
Mastrototaro et al., "Thin-Film Flexible Multielectrode Arrays for Voltage Measurements in the Heart," IEEE Engineering in Medicine & Biology Society 11th Annual International Conference, 1 Page, (1989).
Mastrototaro et al., "Rigid and Flexible Thin-Film Multielectrode Arrays for Transmural Cardiac Recording," IEEE Transactions on Biomedical Engineering, vol. 39, pp. 217-279, (1992).
Mirando-Castro et al., "Hairpin-DNA Probe for Enzyme-Amplified Electrochemical Detection of Legionella pnuemophila," Anal. Chem., vol. 79, pp. 4050-4055, (Jun. 1, 2007).
Nishida, et al. "Self-Oriented Immobilization of DNA Polymerase Tagged by Titanium-Binding Peptide Motif," Langmuir, vol. 31, pp. 732-740 (Dec. 17, 2014).
Niwa, O. et al., "Fabrication and Characteristics of Vertically Separated Interdigitated Array Electrodes," Journal of Electroanalytical Chemistry and Interfacial Electrochemistry, vol. 267 pp. 291-297, (Aug. 10, 1989) (Abstract Only).
Okinaka et al., ""Polymer" Inclusions in Cobalt-Hardened Electroplated Gold," Journal the of Electrochemical Society, vol. 125, p. 1745, (1978). (Abstract Only).
Park, S.J. et al., "Array-Based Electrical Detection of DNA with Nanoparticle Probes," Science, vol. 295, pp. 1503-1506, (Feb. 22, 2002).
Park, C.W. et al., "Fabrication of Poly-Si/ AU Nano-Gaps Using Atomic-Layer-Deposited $Al_2O_3$ as a Sacrificial Layer," Nanotechnology, vol. 16, pp. 361-364, (Feb. 1, 2005) (Abstract Only).
Parkin, I. P. et al., "Self-Cleaning Coatings," Journal of Materials Chemistry, vol. 15(17), pp. 1689-1695, (Dec. 2004).
Prins et al., "Room-Temperature Gating of Molecular Junctions Using Few-Layer Graphene Nanogap Electrodes," Nano Letters, vol. 11, pp. 4607-4611, (Oct. 21, 2011).
Pugliese et al., "Processive Inforporation of Deoxynucleoside Triphosphate Analogs by Single-Molecule DNA Polymerase I (Klenow Fragment) Nanocircuits," Journal of the American Chemical Society, vol. 137, No. 30, pp. 9587-9594 (2015).
Qing et al., "Finely Tuning Metallic Nanogap Size with Electrodeposition by Utilizing High-Frequency Impedance in Feedback," Angewandte Chemie Int ed, vol. 44, pp. 7771-7775,(2005).
Reed et al., "Conductance of a Molecular Junction Reports," Science, vol. 278, pp. 252-254, (Oct. 1997).
Reichert et al., "Driving Current Through Single Organic Molecules," Physical Review Letters, vol. 88(17), pp. 176804-1-176804-4, (Apr. 2002).
Roppert et al., "A New Approach for an Interdigitated Electrodes DNA-Sensor," XVIIIth International Symposium on Bioelectrochemistry and Bioenergetics, Bioelectrochemistry, p. 143, (2005).
Roy, S. et al., "Mass-Produced Nanogap Sensor Arrays for Ultra-Sensitive Detection of DNA," Journal of the American Chemical Society, vol. 131, pp. 12211-12217, (Aug. 5, 2009) (Abstract Only).
Ruttkowski, E. et al., "CMOS based Arrays of Nanogaps Devices for Molecular Devices," Proceedings of 2005 5th IEEE Conference on Nanotechnology, vol. 1, pp. 438-441, (Jul. 2005) (Abstract Only).
Sanguino et al., "Interdigitated Capacitive Immunosensors with PVDF Immobilization Layers," IEEE Sensors Journal, vol. 14(4), pp. 1260-1265, (Apr. 2014).
Santschi et al., "Interdigitated 50nm Ti Electrode Arrays Fabricated using $XeF_2$ Enhanced Focused Ion Beam Etching," Nanotechnology, vol. 17, pp. 2722-2729, (2006).
Schaefer et al., "Stability and Dewetting Kinetics of Thin Gold Films on Ti, TiOx, and ZnO Adhesion Layers," Acta Materialia, vol. 61, pp. 7841-7848, (2013).
Schrott, W. et al., "Metal Electrodes in Plastic Microfluidic Systems," Microelectronic Engineering, vol. 86, pp. 1340-1342, (Jun. 2009).
Shimanovsky et al., "Hiding Data in DNA," International Workshop on Information Hiding, Lecture Notes in Computer Science, pp. 373-386, (Dec. 18, 2012).
Shimoda, T. et al., "Solution-Processed Silicon Films and Transistors," Nature, vol. 440(7085), pp. 783-786, (Apr. 2006).
Sholders et al., "Distinct Conformations of a Putative Translocation Element in Poliovirus Polymerase," Journal of Molecular Biology, vol. 426(7), pp. 1407-1419, (Apr. 3, 2014).
Singh et al., "3D Nanogap Interdigitated Electrode Array Biosensors," Analytical and Bioanalytical Chemistry, vol. 397, pp. 1493-1502, (2010).
Singh et al., "Evaluation of Nanomaterials-Biomolecule Hybrids for Signals Enhancement of Impedimetric Biosensors," 11th IEEE International Conference on Nanotechnology, pp. 707-710, (2011).
Singh et al., "Nanoparticle-Enhanced Sensitivity of a Nanogap-Interdigitated Electrode Array Impedimetric Biosensor," Langmuir, vol. 27, pp. 13931-13939, (2011).
Stagni, C. et al., "CMOS DNA Sensor Array with Integrated A/D Conversation Based on Label-Free Capacitance Measurement," IEEE Journal of Solid-State Circuits, vol. 41, pp. 2956-2964, (Nov. 20, 2006).
Stenning, "The Investigation of Grain Boundary Development and Crystal Synthesis of Thin Gold Films on Silicon Wafers," http://www.ucl.ac.uk/~ucapikr/projects, (Mar. 31, 2009).
Su, Y., "Modeling and Characteristic Study of Thin Film Based Biosensor Based on COMSOL," Mathematical Problems in Engineering, Article 581063 (6 Pages), (Apr. 7, 2014).
Thompson, "Solid-State Dewetting of Thin Films," Department of Materials Science and Engineering, vol. 42, pp. 399-434, (2012).
Urban, M. et al., "A Paralleled Readout System for an Electrical DNA-Hybridization Assay Based on a Microstructured Electrode Array," Review of Scientific Instruments, vol. 74, pp. 1077-1081, (Jan. 2003) (Abstract Only).
Van Gerwin et al., "Nanoscaled Interdigitated Electrode Arrays for Biochemical Sensors," Sensors and Actuators B, vol. 49, pp. 73-80, (1998).
Van Megan et al., "Submicron Electrode Gaps Fabricated by Gold Electrodeposition at Interdigitated Electrodes," Key Engineering Materials, vol. 605, pp. 107-110, (2014).
Wang et al., "Electronics and Optoelectronics of Two-Dimensional Transition Metal Dichalcogenides," Nature Nanotechnology, vol. 7, pp. 699-712, (Nov. 6, 2012).
Xu et al., "Fabrication of Complex Metallic Nanostructures by Nanoskiving," American Chemical Society Nano, vol. 1(3), pp. 215-227, (2007).
Zafarani et al., "Electrochemical Redox Cycling in a New Nanogap Sensor: Design and Simulation," Journal of Electroanalytical Chemistry, vol. 760, pp. 42-47, (2015).
USPTO; Notice of Allowance dated May 11, 2020 in U.S. Appl. No. 16/073,706.
USPTO; Notice of Allowance dated Jun. 1, 2020 in U.S. Appl. No. 16/076,673.
USPTO; Non-Final Office Action dated Jun. 2, 2020 in U.S. Appl. No. 16/684,338.
USPTO; Non-Final Office Action dated Jun. 15, 2020 in U.S. Appl. No. 16/878,484.
USPTO; Non-Final Office Action dated Jun. 30, 2020 in U.S. Appl. No. 16/479,257.
USPTO; Non-Final Office Action dated Jun. 30, 2020 in U.S. Appl. No. 16/477,106.
EP; European Search Report dated Jun. 18, 2020 in Application No. 16815467.2.
CN; Office Action dated Jun. 5, 2020 in Chinese Patent Application No. 2017800204782.
EP; European Search Report dated Jun. 26, 2020 in Application No. 17874229.2.

(56) References Cited

OTHER PUBLICATIONS

Li et al., "Graphene Channel Liquid Container Field Effect Transistor as pH Sensor," Hindawi Publishing Corp., Journal of Nanomaterials 2014.
USPTO; Notice of Allowance dated Nov. 24, 2020 in U.S. Appl. No. 16/477,106.
USPTO; Notice of Allowance dated Dec. 7, 2020 in U.S. Appl. No. 16/878,484.
USPTO; Final Office Action dated Dec. 14, 2020 in U.S. Appl. No. 16/684,338.
USPTO; Final Office Action dated Jan. 6, 2021 in U.S. Appl. No. 16/070,133.
USPTO; Non-Final Office Action dated Dec. 15, 2020 in U.S. Appl. No. 16/831,722.
USPTO; Non-Final Office Action dated Dec. 30, 2020 in U.S. Appl. No. 16/652,672.
EP; European Search Report dated Nov. 19, 2020 in Application No. 18739158.6.
JP; Office Action dated Dec. 2, 2020 in Japanese Patent Application No. 2018-536737.
EP; European Search Report dated Dec. 23, 2020 in Application No. 18790713.4.
EP; European Search Report dated Dec. 14, 2020 in Application No. 18799263.1.
Ali et al., "DNA hybridization detection using less than 10-nm gap silicon nanogap structure," Sensors and Actuators A. vol. 199, pp. 304-309 (2013).
Bornholt et al., "A DNA-Based Archival Storage System", Architectural Support For Programming Languages and Operating Systems, pp. 637-649 (2016).
Chen et al., "Silicon nanowire field-effect transistor-based biosensors for biomedical diagnosis and cellular recording investigation", Nano Today, Elsevier, Amsterdam, NL, vol. 6, No. 2, pp. 131-154 (2011).
Grass et al., "Robust Chemical Preservation of Digital Information on DNA in Silica with Error-Correcting Codes", Angewandte Chemie International Edition, vol. 54, No. 8, pp. 2552-2555 (2015).
Hatcher et al., "PNA versus DNA: Effects of Structural Fluctuations on Electronic Structure and Hole-Transport Mechanisms," J. Amer. Chem. Soc., 130, pp. 11752-11761 (2008).
Korlach et al., "Real-time DNA sequencing from single polymerase molecules," 11, Methods In Enzymology, Academy Press, vol. 472, pp. 431-455 (2010).
Paul et al., "Charge transfer through Single-Stranded Peptide Nucleic Acid Composed of Thymine Nucleotides," J. Phy. Chem. C 2008, 112, pp. 7233-7240 (2008).
Shin et al., "Distance Dependence of Electron Transfer Across Peptides with Different Secondary Structures: The Role of Peptide Energetics and Electronic Coupling," J. Amer. Chem. Soc. 2003, 125, pp. 3722-3732 (2003).
Venkatramani et al., "Nucleic Acid Charge Transfer: Black, White and Gray," Coard Chem Rev., 255(7-8): pp. 635-648 (2011).
Office Action dated Jun. 15, 2020 for U.S. Appl. No. 16/878,484.
Office Action dated Jun. 2, 2020 for U.S. Appl. No. 16/684,338.
Office Action dated Jun. 30, 2020 for U.S. Appl. No. 16/477,106.
Office Action dated Oct. 2, 2020 for U.S. Appl. No. 16/073,693.
Office Action dated Sep. 22, 2020 for U.S. Appl. No. 16/639,716.

* cited by examiner

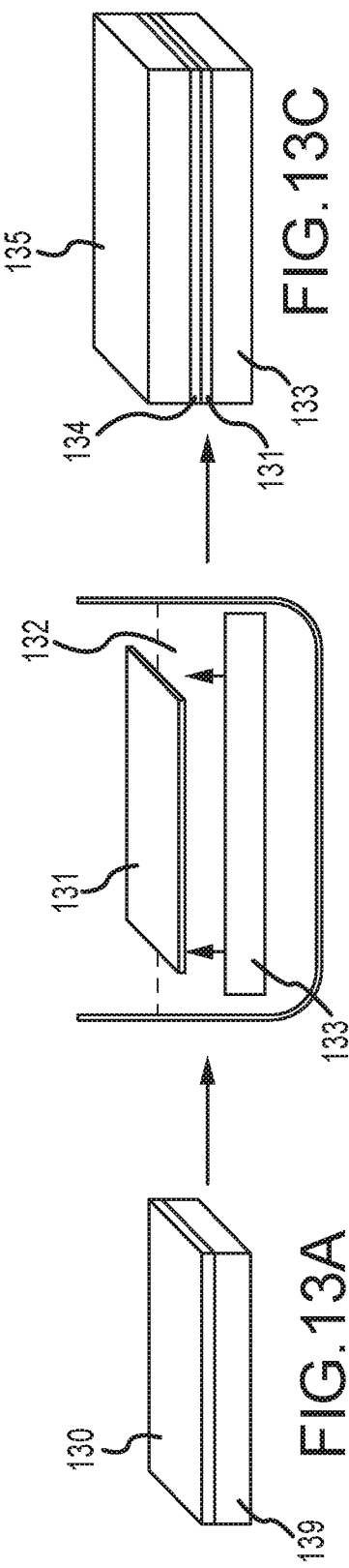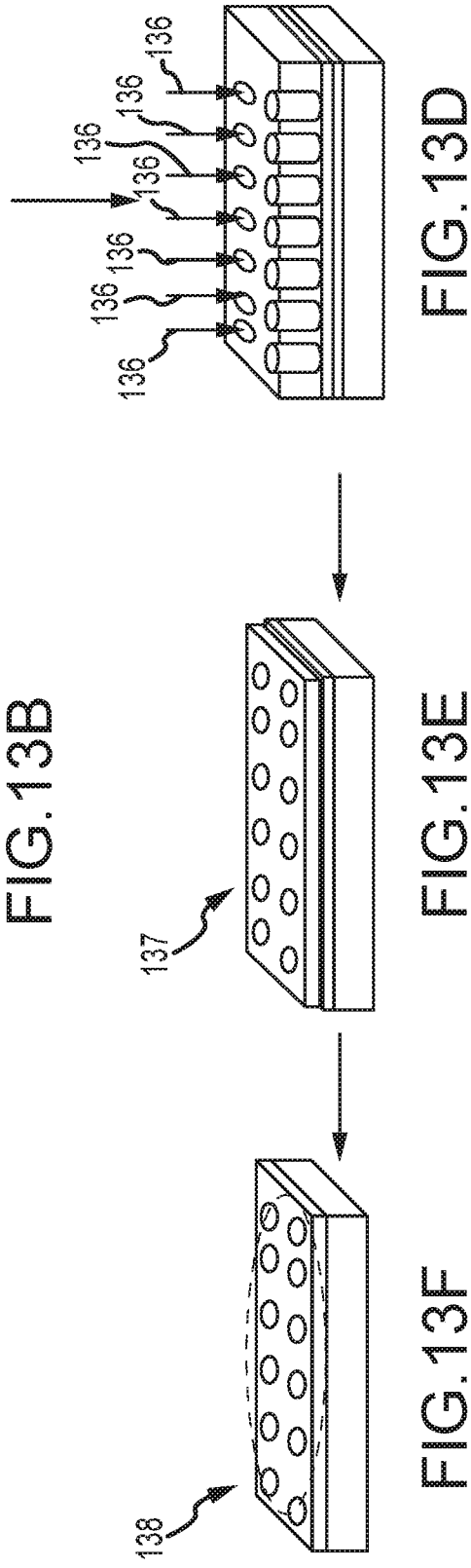

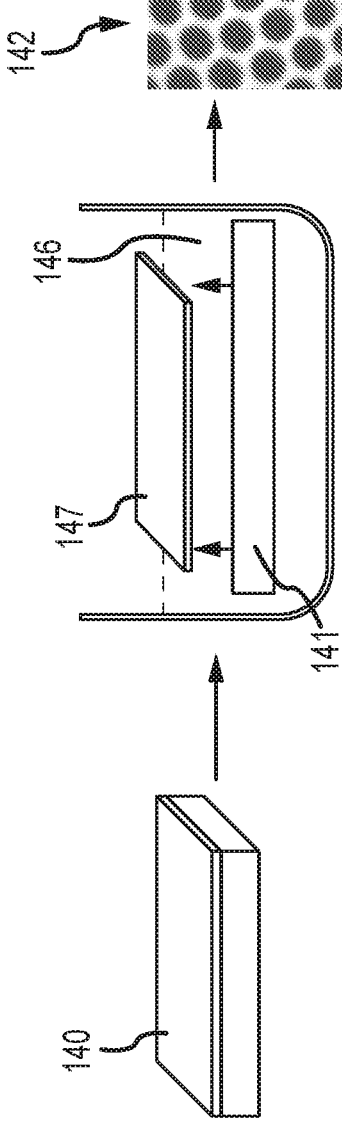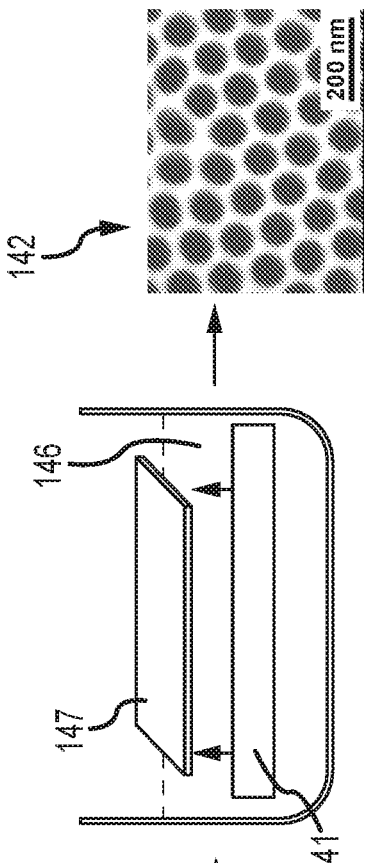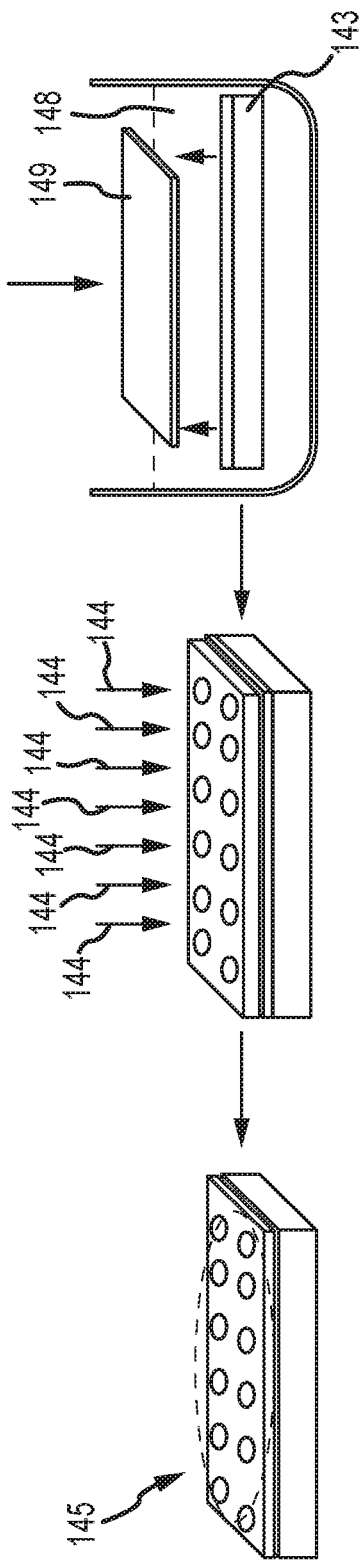

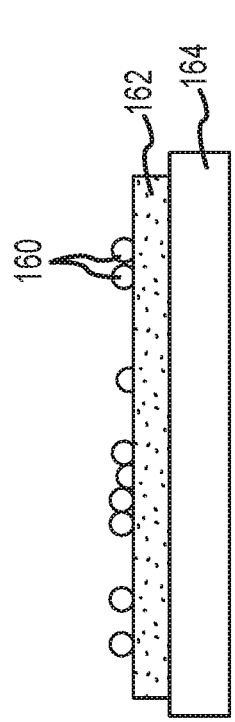
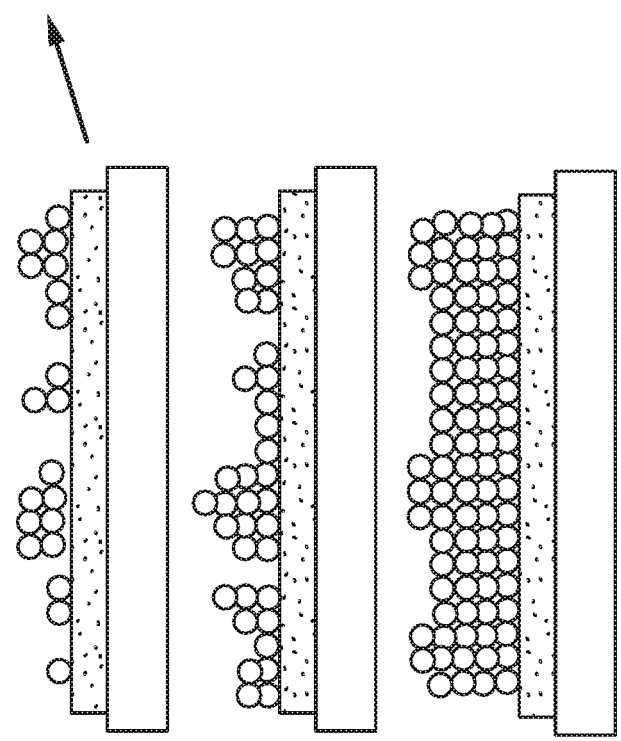
FIG. 14A
FIG. 14B
FIG. 14C
FIG. 14D
FIG. 14E

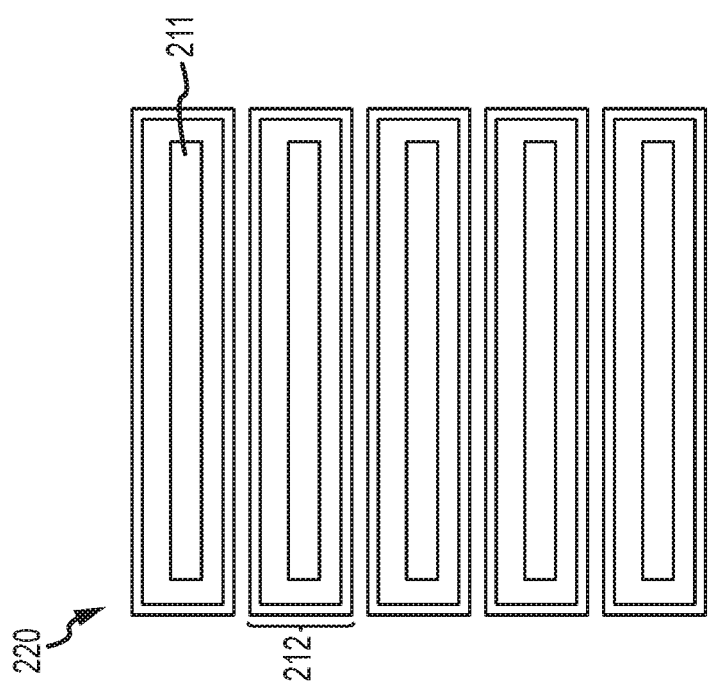
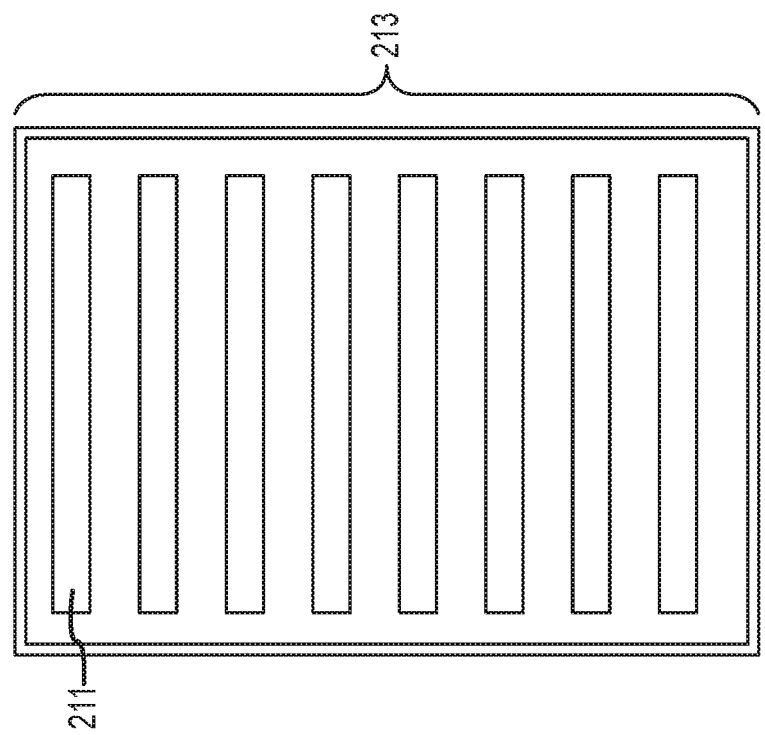
FIG.22A
FIG.22B

SOLID STATE SEQUENCING DEVICES COMPRISING TWO DIMENSIONAL LAYER MATERIALS

CROSS-REFERENCE TO RELATED APPLICATIONS

This application is a U.S. national phase filing under 35 U.S.C. § 371 of PCT/US2017/063105, filed on Nov. 22, 2017 entitled "SOLID STATE SEQUENCING DEVICES COMPRISING TWO DIMENSIONAL LAYER MATERIALS," which claims priority to U.S. Provisional Patent Application Serial Number 62/448,078, filed on Jan. 19, 2017, the disclosures of which are is incorporated herein by reference in its entirety their entireties.

FIELD

The present disclosure relates to nanofabrication of biomolecular sensing devices. More particularly, the present disclosure relates to the fabrication of devices for analyzing DNA and related biomolecules, wherein the devices contain two dimensional layer materials.

BACKGROUND

Analysis of biomolecules including DNAs and genomes has received an increasing amount of attention in recent years in various fields of precision medicine or nanotechnology. The seminal work of Maclyn McCarty and Oswald T. Avery in 1946 (see, "Studies On The Chemical Nature Of The Substance Inducing Transformation Of Pneumococcal Types II. Effect Of Deoxyribonuclease On The Biological Activity Of The Transforming Substance," The *Journal of Experimental Medicine* 83(2), 89-96 (1946)), demonstrated that DNA was the material that determined traits of an organism. The molecular structure of DNA was then first described by James D. Watson and Francis H C Crick in 1953, (see a published article, "Molecular structure of nucleic acids.", *Nature* 171, 737-738 (1953)), for which they received the 1962 Nobel Prize in Medicine. This work made it clear that the sequence of chemical letters (bases) of the DNA molecules encode the fundamental biological information. Since this discovery, there has been a concerted effort to develop means to actually experimentally measure this sequence. The first method for systematically sequencing DNA was introduced by Sanger, et al in 1978, for which he received the 1980 Nobel Prize in Chemistry. See an article, Sanger, Frederick, et al., "The nucleotide sequence of bacteriophage φX174." *J. Mol. Bio.* 125, 225-246 (1978).

Sequencing techniques for genome analysis evolved into utilizing automated commercial instrument platform in the late 1980's, which ultimately enabled the sequencing of the first human genome in 2001. This was the result of a massive public and private effort taking over a decade, at a cost of billions of dollars, and relying on the output of thousands of dedicated DNA sequencing instruments. The success of this effort motivated the development of a number of "massively parallel" sequencing platforms with the goal of dramatically reducing the cost and time required to sequence a human genome. Such massively parallel sequencing platforms generally rely on processing millions to billions of sequencing reactions at the same time in highly miniaturized microfluidic formats. The first of these was invented and commercialized by Jonathan M. Rothberg's group in 2005 as the 454 platform, which achieved thousand fold reductions in cost and instrument time. See, an article by Marcel Margulies, et al., "Genome Sequencing in Open Microfabricated High Density Picoliter Reactors," *Nature* 437, 376-380 (2005). However, the 454 platform still required approximately a million dollars and took over a month to sequence a genome.

The 454 platform was followed by a variety of other related techniques and commercial platforms. See, articles by M. L. Metzker, "Sequencing Technologies—the Next Generation," *Nature Rev. Gen.* 11(1), 31-46 (2010), and by C. W. Fuller et. al, "The Challenges of Sequencing by Synthesis," *Nature Biotech.* 27(11), 1013-1023 (2009). This progress lead to the realization of the long-sought "$1,000 genome" in 2014, in which the cost of sequencing a human genome at a service lab was reduced to approximately $1,000, and could be performed in several days. However, the highly sophisticated instrument for this sequencing cost nearly one million dollars, and the data was in the form of billions of short reads of approximately 100 bases in length. The billions of short reads often further contained errors so the data required interpretation relative to a standard reference genome with each base being sequenced multiple times to assess a new individual genome.

Thus, further improvements in quality and accuracy of sequencing, as well as reductions in cost and time are still needed. This is especially true to make genome sequencing practical for widespread use in precision medicine (see the aforementioned article by Fuller et al), where it is desirable to sequence the genomes of millions of individuals with a clinical grade of quality.

While many DNA sequencing techniques utilize optical means with fluorescence reporters, such methods can be cumbersome, slow in detection speed, and difficult to mass produce to further reduce costs. Label-free DNA or genome sequencing approaches provide advantages of not having to use fluorescent type labeling processes and associated optical systems, especially when combined with electronic signal detection that can be achieved rapidly and in an inexpensive way.

While current molecular electronic devices can electronically measure molecules for various applications, they lack the reproducibility as well as scalability and manufacturability needed for rapidly sensing many analytes at a scale of up to millions in a practical manner. Such highly scalable methods are particularly important for DNA sequencing applications, which often need to analyze millions to billions of independent DNA molecules. In addition, the manufacture of current molecular electronic devices is generally costly due to the high level of precision needed.

SUMMARY

In various embodiments described herein, specially processed, 2D layer-containing enzyme polymerase sensor device structures and methods of manufacture for a multitude of devices for use in electronic DNA, RNA or genome sequencing systems are disclosed. Such label-free, single molecule based sequencing analysis systems utilize preferably a microstructurally controlled transition metal dichalcogenide (TMD) layer with intentionally defective structures, so as to utilize altered bandgaps and enhanced attachment of single biomolecules such as enzyme polymerase molecules. The electronic system may also be used in analyzing other types of biomolecules, such as proteins, depending on how the molecular sensors are functionalized to interact with biomolecule sensing targets. The TMD-based sequencing systems invented here can be assembled into a massively parallel configuration for rapid analysis of targets including nucleotides, in particular for applications to sequencing of a DNA molecule, or a collection of such molecules constituting an entire human genome.

In an aspect, a sequencing device is disclosed. The sequencing device includes an electrode array of conducting electrode pairs, each pair of electrodes comprising a source and a drain electrode separated by a nanogap, said electrode array deposited and patterned on a dielectric substrate; a single-layer or few-layer thick transition metal dichalcogenide (TMD) layer disposed on each pair of electrodes, connecting each source and drain electrode within each pair, and bridging each nanogap of each pair; a dielectric masking layer disposed on the TMD layer and comprising size-limited openings that define exposed TMD regions, each opening sized so as to allow only a single enzyme biomolecule to fit therein and to attach onto the exposed TMD region defined by each opening; an enzyme molecule attached to each exposed TMD region such that only one enzyme molecule is found within each opening; and a microfluidic system encasing the electrode array, wherein attachment or detachment of a biomolecule selected from the group consisting of a nucleotide monomer, a protein, and a DNA segment, onto the enzyme molecule, one at a time, can be monitored as a uniquely identifiable electrical signal pulse to determine the specific nature of the biomolecule attaching or detaching. In embodiments, the TMD is selected from $MoS_2$, $WS_2$, $TiS_2$, $ZrS_2$, $HfS_2$, $VS_2$, $NbS_2$, $TaS_2$, $TcS_2$, $ReS_2$, $CoS_2$, $RhS_2$, $IrS_2$, $NiS_2$, $PdS_2$, $PtS_2$ and their modifications or combinations, including modified stoichiometry of sulfur contents having $MX_{(2-x)}$ or $MX_{(2+x)}$ wherein x is in the range of 0-1.0, preferably in the range of 0-0.5, even more preferably 0-0.3. In embodiments, the sulfur stoichiometry is intentionally altered so as to provide vacancy defects, interstitial defects, and aggregated defects so as to increase the surface energy and enhance the adhesion of biomolecule to the bridge sensor, increasing the bandgap for stronger electrical signal pulse. In embodiments, the TMD is selected from $MoSe_2$, $WSe_2$, or $TiSe_2$, $ZrSe_2$, $HfSe_2$, $VSe_2$, $NbSe_2$, $TaSe_2$, $TcSe_2$, $ReSe_2$, $CoSe_2$, $RhSe_2$, $IrSe_2$, $NiSe_2$, $PdSe_2$, $PtSe_2$ and their modifications or combinations, including modified stoichiometry of selenium contents having $MX_{(2-x)}$ or $MX_{(2+x)}$ with the desired value of x in the range of 0-1.0, preferably in the range of 0-0.5, even more preferably 0-0.3. In embodiments, the selenium stoichiometry is intentionally altered so as to provide vacancy defects, interstitial defects, and aggregated defects in order to increase the surface energy of the TMD layer and enhance the adhesion of biomolecule to the bridge sensor for stronger sensor signals. In embodiments, the TMD is selected from $MoTe_2$, $WTe_2$, or $TiTe_2$, $ZrTe_2$, $HfTe_2$, $VTe_2$, $NbTe_2$, $TaTe_2$, $TcTe_2$, $ReTe_2$, $CoTe_2$, $RhTe_2$, $IrTe_2$, $NiTe_2$, $PdTe_2$, $PtTe_2$ and their modifications or combinations, including modified stoichiometry of tellurium contents having $MX_{(2-x)}$ or $MX_{(2+x)}$ with the desired value of x in the range of 0-1.0, preferably in the range of 0-0.5, even more preferably 0-0.3. In embodiments, the tellurium stoichiometry is intentionally altered so as to provide vacancy defects, interstitial defects, and aggregated defects in order to increase the surface energy of the TMD layer and enhance the adhesion of biomolecule to the bridge sensor for stronger sensor signals. In embodiments, the TMD comprises a mixed TMD selected from TMD compounds in which the $MX_2$ compound has mixed metals and/or mixed chalcogenide, selected from the group consisting of $Mo(S_xSe_yTe_z)_2$, $W(S_xSe_yTe_z)_2$, $Ti(S_xSe_yTe_z)_2$, $Zr(S_xSe_yTe_z)_2$, $Hf(S_xSe_yTe_z)_2$, $V(S_xSe_yTe_z)_2$, $Nb(S_xSe_yTe_z)_2$, $Ta(S_xSe_yTe_z)_2$, $Tc(S_xSe_yTe_z)_2$, $Re(S_xSe_yTe_z)_2$, $Co(S_xSe_yTe_z)_2$, $Rh(S_xSe_yTe_z)_2$, $Ir(S_xSe_yTe_z)_2$, $Ni(S_xSe_yTe_z)_2$, $Pd(S_xSe_yTe_z)_2$, and $Pt(S_xSe_yTe_z)_2$ wherein the combined (x+y+z) is 1-3, 0.5-1.5, or 0.7-1.3. In further embodiments, two or more metals are combined for sulfur containing, Se-containing or Te-containing TMD layers. In embodiments, the TMD layer comprises $Mo_xW_yCo_z)S_2$ or $(Hf_xW_yCo_z)Te_2$. In embodiments, the TMD comprises a $M_{(1-w)}N_wX_{(2-z)}Y_z$ structure in which the transition metal M is partially substituted with non-transition elements N, with a concentration of w and the N element selected from one or more of Al, Si, Ga, Ge, In, Sn, Sb, Bi, Al, Na, K, Ca, Mg, Sr, Ba, with the w value in the range of 0-0.3, and the chalcogenide element X partially substituted with a non-chalcogenide element Y, with the Y element selected from one or more of Li, B, C, N, O, P, F, Cl, I, with the z value in the range of 0-0.3. In embodiments, the metallic conducting electrode pair is selected from Au, Pt, Ag, Pd, Rh, or their alloys. In embodiments, the nanogap is about 2 nm to about 20 nm. In embodiments, the size-limited openings are preferably less than 30 nm average equivalent diameter each, more preferably less than about 20 nm equivalent diameter, even more preferably less than about 10 nm equivalent diameter, by lithographically defined coverage of dielectric material layer of polymer or ceramic outside a specific region intended for attaching only a single molecule. In embodiments, the size-limited openings are about 30 nm equivalent diameter each, or about 20 nm equivalent diameter each, or about 10 nm equivalent diameter each, and wherein the TMD layer comprises an intentionally damaged structure with insulator or very high resistivity characteristics serving as the mask material to enable single molecule attachment; with at least 100 ohm-cm, preferably at least 10,000 ohm-cm, even more preferably at least 1 mega ohm-cm resistivity for the regions outside a specific region intended for attaching only a single molecule; and with the intentional damaging performed by electron bombardment, laser radiation bombardment, ion bombardment, or ion implant doping.

In further embodiments, the TMD layer is defective with the defects selected from linear nano-ribbon parallel array, patterned shape nano-ribbon array, strained lattice defects, vacancies, interstitial defects, dislocation defects, foreign atom implanted defects, or nanoporous defects. In embodiments, the size-limited TMD layer contains strained lattice defects, vacancies, interstitial defects, dislocation defects or foreign atom implanted defects with a defect density of at least about $10^5/cm^2$. In embodiments, the defects in the TMD layer are nanoporous defects having an equivalent diameter of at least 2 nm with a defect density of at least about $10^3/cm^2$. In embodiments, the TMD layer is defective with the bandgap opened additionally by at least 0.2 eV, preferably by at least 0.5 eV compared to the TMD without defects. In embodiments, the TMD layer surface exhibits hydrophilic characteristics with a hydrophilic area having a water droplet contact angle of at most 50 degrees, preferably at most 30 degrees, even more preferably at most 15 degrees; with an improved biomolecule attachment frequency with the adhesion improvement by at least 30%, preferably by at least 50%, even more preferably by at least 100% increased adhesion event as compared to the all hydrophobic TMD surface during microfluidic chamber processing of fluid supplying to provide biomolecules, nucleotides, and related biological or chemical components, as well as washing or fluid replacement operations; and the hydrophilic characteristics are associated with defects including strained lattice, vacancies, interstitials, dislocations, nanopores, nano-pinholes, foreign atom doping, with the defect density being at least about $10^3/cm^2$, and preferably at least about $10^5/cm^2$. In embodiments, the TMD layer surface consists of a mixed structure of a hydrophilic region and a hydrophobic region, and the hydrophilic area has a water droplet contact angle of at most 50 degrees, preferably at most 30 degrees, even more preferably at most 15 degrees; the area fraction of the hydrophilic region is at least 10%, preferably at least 30%, even more preferably at least 50% area fraction of the exposed TMD surface to attract a single biomolecule; the hydrophilic regions are in the form of circular, oval, rectangular, or irregular islands, or in a striped configuration; the TMD surface has defects such as vacancies, interstitials, dislocations or aggregated defects, nanopores, chemically doped regions with foreign atoms, or striped pores, with the density of such defects being at least $10^3/cm^2$, preferably at least $10^5/cm^2$, and such a composite hydrophilic-hydrophobic configuration enables improved biomolecule attachment frequency with the adhesion improvement by at least 30%, preferably by at least 50%, even more preferably by at least 100% increased adhesion event as compared to the all hydrophobic TMD surface during microfluidic chamber processing of fluid supplying to provide biomolecules, nucleotides, and related biological or chemical components, as well as washing or fluid replacement operations; and/or the size of either hydrophilic islands or hydrophobic islands is desirably 1-30 nm, preferably 1-10 nm, and more preferably 1-5 nm. In further embodiments, the TMD layer has tunable hydrophilicity, wherein: the TMD layer is either suspended between two electrodes or fixed on top of two electrodes without suspended structural configuration; the TMD bridge surface is size-limited for attachment of single biomolecule; on-demand switching of hydrophobic to hydrophilic surface state is enabled by a device configuration of at least a pair of vertical electrodes positioned below and above the sensor bridge structure so as to apply electric field of at least 10 V/nm, preferably at least 30 V/nm to alter the semiconducting properties and widen the bandgap by at least 5%, preferably at least 10%, and make the TMD more hydrophilic with the water droplet contact angle to decrease by at least 5 degrees, preferably by at least 20 degrees for easier accommodation of microfluidic chamber environment and improved adhesion probability of single enzyme molecule such as DNA or RNA polymerase increasing by at least 30%; the electric field applied is a DC electric field or AC electric field; hydrophilic improvement is capable of being reversed to return to hydrophobic state to enable a release of previously used biomolecule and to avoid unnecessary attachment of biomolecules; and/or optionally having at least 1,000, preferably as many as 10,000 or even more preferably at least 1 million devices, with one or more selected electrode-paired devices simultaneously or in a series operation tunable to be hydrophilic or hydrophobic. In embodiments, the biomolecule to be attached onto the TMD is a polymerase enzyme. In embodiments, the biomolecule to be attached onto the TMD is selected from various other biopolymers of DNA, RNA, proteins, ribozyme, aptamer or polysaccharide. In embodiments, the two-dimension shaped TMD layer is locally converted to three-dimensionally shaped TMD, so as to provide mechanical support for robust and reliable TMD positioning, with additional defects at the curved or kinked position with displaced or strained lattice in TMD, to produce higher-energy-state positions for enhanced adhesion of enzyme biomolecules, with the altered shape TMD having the following structural characteristics of: an introduction of new modes of defects and shape discontinuity for higher-energy-state local regions; a shape-altering insert structure made of dielectric material selected from polymer materials or ceramics materials; the shape-altering insert structure having a uniformly or non-uniformly protruding structure beyond the level of metallic conductor electrode top surface so as to make the TMD layer non-flat geometry selected the configuration of being bent, curvatured, dome-shaped, irregular-shaped, buckled, or locally punctured shape and introduce displaced; the shape-altered TMD layer already possessing a defective structure comprising lattice defects of strained lattice, vacancies, interstitials, dislocations, nanopores, chemically doped regions with a defect density of at least $10^3/cm^2$; the altered shape selected from hemispherical, rectangle, oval, wavy, or other periodic or irregular geometry; and/or the shape-altering insert permanently left underneath the TMD layer to serve as a beneficial mechanical support to guard against mechanical detachment or damage of the TMD layer during microfluidic handling of the sequencing device systems and associated inadvertent force applied to the suspended or barely bonded TMD layer on the nanogap region, or etched away to leave a mechanically compliant, protruding TMD layer.

In further embodiments, the TMD layer is in contact with the dielectric substrate with no nanogap, and a pair of metallic electrodes extend from both ends of the TMD island as electric lead wires. In further embodiments, the polymerase enzyme connection to the TMD surface is via functional groups or functional group pairs selected from a list of streptavidin-biotin pair, antigen-antibody interaction, bifunctional ligands using mercaptocarbonic acids [HS—$(CH_2)n$—COOH, n=1-15], peptide functional groups, thiol-alkyne pair, COOH—$NH_2$ functional group pair, a thiol-maleimide azide pair, silanization linkage using mercaptosilane compounds, and a NHS (N-hydroxysuccinimide) ester-amine pair. In embodiments, the dNTP nucleotide being attached to the enzyme polymerase molecule is a modified nucleotide type to enhance the incorporation signals, or produce signals with enhanced differences between the different base (A, C, G, T) incorporation events, for greater accuracy determining the template sequence, with such dNTP modifications include modifications of: the base, such as 7-deaza forms, 8-bromo forms; the alpha- and beta-phosphates, such as thiolated forms or bromated forms of these phosphates; the gamma-phosphate modifications, including the addition of phosphates, such as tetra-, penta- or hexa-phosphates forms; or the groups added to the terminal phosphate.

In further embodiments, the electrode arrangement comprises a triode configuration with a gate electrode placed parallel to each of said source and drain electrodes or perpendicular to each nanogap between each of source and drain electrodes in the electrode array. In further embodiments, the electrodes, TMD layer, masking dielectric, and enzyme molecule are arranged into an array configuration so as to allow massively parallel electronic sequencing analysis using devices organized into a system having at least 1,000, preferably at least 1 million devices. In embodiments, a sequential interrogation of an array of electrodes in the TMD-containing polymerase enzyme molecular sensor is enabled for DNA or genome sequencing by using a common lead wire on one side of the array. In embodiments, the electrodes, TMD layer, masking dielectric, and enzyme molecule are arranged into a three-dimensional array of molecular electronics genome-sequencing platform using a stacked microfluidic chamber or a common microfluidic chamber for a stacked layer devices, so as to allow massively parallel electronic sequencing analysis using devices organized into a system having at least 1,000, preferably at least 1 million devices.

In another aspect, a method of fabricating a TMD based DNA or genome sequencing device is provided. The method involves providing an array of metallic conducting electrode pairs with a source and drain arrangement deposited and patterned on a dielectric substrate; depositing a single-layer or few-layer TMD by using a liquid container lift-up placement method onto the electrode array, by using a vacuum transfer method, or by using a stamp transfer method; nanopatterning a dielectric masking layer placed on the TMD surface with an opening which is size-limited so as to allow only a single enzyme biomolecule to attach onto the exposed TMD surface for sequencing analysis; placing the sequencing device into a microfluidic system and supplying a fluid containing denaturized nucleotide molecules or modified nucleotides, and chemical agents; and making an electronic measurement and computer analysis on the event of individual nucleotide monomers or modified nucleotide components attachment onto an enzyme polymerase molecule one at a time to obtain electrical pulse signals to determine the specific nature of the nucleotide being attached. In embodiments, the TMD layer is made defective by nanopatterning into linear nano-ribbon parallel array or patterned shape nano-ribbon array, or introducing disturbed lattice defects of strained lattice, vacancies, interstitials, dislocations, chemical doped or ion implant doped regions, or providing nanoporous defects or nano-pinholes defects. In embodiments, the defects in TMD layer are introduced by beam irradiation selected from ion implantation beam, plasma reactive ion etch (RIE) atmosphere, broadened optical, electron, ion or neutron beam, so as to introduce defect density of at least about $10^5/cm^2$. In embodiments, the irradiated structure is post-irradiation annealed at about 100° C. to about 600° C. In embodiments, the TMD lattice defects or nanopores are introduced by chemical etching using oxidizing chemicals, strong acids, strong alkaline solutions, so as to introduce defect density of at least about $10^5/cm^2$. In embodiments, the TMD with nanoporous defects are introduced by using a nano-hole containing template selected from block copolymer or anodized aluminum oxide so as to introduce defect density of at least $10^5/cm^2$. In embodiments, the TMD with nanoporous defects are introduced by using completely deposited thin films comprising nano-pinholes as a mask through which the TMD layer is etched so as to introduce nano-pinholes defect density of at least about $10^5/cm^2$. In embodiments, the TMD with nanoporous defects are introduced by using nanoimprinting patterning so as to introduce defect density of at least $10^5/cm^2$. In embodiments, the TMD with nanoporous defects are introduced by using metallic nanoparticles spray deposited onto TMD, allowing diffusional reactions and differential chemical etching. In embodiments, the TMD layer material outside a specific region that is intended for a single biomolecule to be attached is intentionally damaged, with the crystal structure of TMD material affected and behave like an insulator or very high resistivity material with at least 100 ohm-cm, preferably at least 10,000 ohm-cam, even more preferably at least 1 mega ohm-cm resistivity using a processing methods selected from the group consisting of electron beam irradiation, ion beam irradiation, optical or laser beam irradiation, particle beam irradiation, and ion implantation of foreign species atoms. In embodiments, the TMD layer material is made to exhibit a hydrophilic state obtained by using one or more of the following processing techniques: by using a plasma treatment using oxygen-containing plasma or other types of plasma containing nitrogen, chlorine, fluorine or mixed elements, or by using imperfect crystallization with defects such as strained lattice, vacancies, interstitials, dislocations nanopores or aggregated defects) in the $MoS_2$ structure (or TMD structure in general), e.g., by sulfurization anneal (or selenium or tellurium diffusion anneal process) at lower temperatures during sulfurization synthesis of TMD layer from the pre-deposited metal layer, with the process temperature selected to be lower by at least 50° C., preferably by at least 200° C. lower than the temperature for obtaining high-quality crystallization with more than 90% of the material having well crystallized TMD layer material, or by using a non-completed crystallization process with defects such as strained lattice, vacancies, interstitials, dislocations nanopores or aggregated defects) in the $MoS_2$ structure (or TMD structure in general), e.g., by sulfurization anneal (or selenium or tellurium diffusion anneal process) for shorter time periods during sulfurization synthesis of TMD layer from the pre-deposited metal layer, with the process time selected to be shorter by a factor of at least 3, preferably by a factor of 10 than the annealing time needed for obtaining high-quality crystallization with more than 90% of the material having well crystallized TMD layer material or by a deposition of a thin hydrophilic surface layer less than 10 nm thickness, such as transition metals like Ti, Zr, Hf, V, Nb, Ta, Cr, Mo, W, Mn, Fe, Co, Ni, Cu, Zn, or ceramic islands of these elements such as $TiO_2$, NiO, $Fe_2O_3$ using physical deposition, chemical deposition, electrochemical deposition, or ion implantation. In further embodiments, the TMD layer material is made to exhibit a combined hydrophilic and hydrophilic mixed phase state obtained by using one or more of the following processing techniques: by using a plasma treatment using oxygen-containing plasma or other types of plasma containing nitrogen, chlorine, fluorine or mixed elements, or by using imperfect crystallization with at least 10%, preferably at least 30% area fraction of TMD surface material having an imperfect crystal lattice configuration, with defects such as vacancies, interstitials, dislocations nanopores or aggregated defects) in the $MoS_2$ structure (or TMD structure in general), e.g., by sulfurization anneal (or selenium or tellurium diffusion anneal process) at lower temperatures and shorter times during sulfurization synthesis of TMD layer from the pre-deposited metal layer, with the process temperature selected to be lower by at least 50° C., preferably by at least 200° C. lower than the temperature for obtaining high-quality crystallization with more than 90% of the material having well crystallized TMD layer material, or by using a non-completed crystallization process with at least 10%, preferably at least 30% area fraction of TMD surface material having an imperfect crystal lattice configuration, with defects such as vacancies, interstitials, dislocations nanopores or aggregated defects) in the $MoS_2$ structure (or TMD structure in general), e.g., by sulfurization anneal (or selenium or tellurium diffusion anneal process) for shorter time periods during sulfurization synthesis of TMD layer from the pre-deposited metal layer, with the process time selected to be shorter by a factor of at least 3, preferably by a factor of 10 than the annealing time needed for obtaining high-quality crystallization with more than 90% of the material having well crystallized TMD layer material, or by a partial deposition of hydrophilic islands such as metallic islands of transition metals like Ti, Zr, Hf, V, Nb, Ta, Cr, Mo, W, Mn, Fe, Co, Ni, Cu, Zn, or ceramic islands of these elements such as $TiO_2$, NiO, $Fe_2O_3$., with an areal fraction of 5-50%, preferably at least 10%, more preferably at least 30%, using physical deposition, chemical deposition, electrochemical deposition, or ion implantation.

In further embodiments, a tunable hydrophilic TMD layer material is produced by using the following processing method: a DC or AC electric field is applied to the vertically arranged two electrodes, one above and one below the TMD layer with the applied electric field being at least 10 V/nm, preferably at least 30 V/nm to alter the semiconducting properties, with the bandgap widened by at least 5%, preferably at least 10%, and with the TMD made more hydrophilic with the water droplet contact angle to decrease by at least 5 degrees, preferably by at least 20 degrees for easier accommodation of fluidic chamber environment and improved adhesion of single enzyme molecule such as DNA or RNA polymerase. In certain embodiments, when the device is not in use, the device is evacuated and back-filled with inert gas so as to minimize inadvertent adhesion or adsorption of unwanted molecules. The devices disclosed herein may be used for whole genome sequences or to diagnose diseases, including but not limited to cancers.

In another aspect, a sequencing device is disclosed. The sequencing device includes an array of conducting electrode pairs, each pair of electrodes comprising a source and a drain electrode arrangement separated by a nanogap, the electrode array deposited and patterned on a dielectric substrate; at least one transition metal dichalcogenide (TMD) layer disposed on each pair of electrodes, wherein the TMD layer connects each source and drain electrode within each pair, and bridges each nanogap of each pair of electrodes; and a dielectric masking layer disposed on the TMD layer and comprising at least one opening that defines an exposed TMD region, wherein the at least one opening is sized so as to allow a single biomolecule to fit therein and to attach on to the exposed TMD region. In embodiments, at least one biomolecule is attached to the exposed TMD region. In embodiments, the at least one biomolecule comprises a polymerase enzyme. In embodiments, the sequencing device further includes a microfluidic system in fluid combination with the sequencing device to provide the at least one biomolecule. In embodiments, the TMD layer comprises $MoS_2$, $WS_2$, $TiS_2$, $ZrS_2$, $HfS_2$, $VS_2$, $NbS_2$, $TaS_2$, $TcS_2$, $ReS_2$, $CoS_2$, $RhS_2$, $IrS_2$, $NiS_2$, $PdS_2$, $PtS_2$, or any of their modifications or combinations, including modified stoichiometry of sulfur contents having $MX_{(2-x)}$ or $MX_{(2+x)}$, wherein x is in the range of 0-1.0. In embodiments, the sulfur stoichiometry is intentionally altered so as to provide vacancy defects, interstitial defects, and aggregated defects so as to increase the surface energy and enhance the adhesion of the biomolecule to the exposed TMD region. In embodiments, the TMD layer comprises $MoSe_2$, $WSe_2$, $TiSe_2$, $ZrSe_2$, $HfSe_2$, $VSe_2$, $NbSe_2$, $TaSe_2$, $TcSe_2$, $ReSe_2$, $CoSe_2$, $RhSe_2$, $IrSe_2$, $NiSe_2$, $PdSe_2$, $PtSe_2$, or any of their modifications or combinations, including modified stoichiometry of selenium contents having $MX_{(2-x)}$ or $MX_{(2+x)}$, wherein x is in the range of 0-1.0. In embodiments, the selenium stoichiometry is intentionally altered so as to provide vacancy defects, interstitial defects, and aggregated defects in order to increase the surface energy of the TMD layer and enhance the adhesion of the biomolecule to the exposed TMD region. In embodiments, the TMD layer comprises $MoTe_2$, $WTe_2$, $TiTe_2$, $ZrTe_2$, $HfTe_2$, $VTe_2$, $NbTe_2$, $TaTe_2$, $TcTe_2$, $ReTe_2$, $CoTe_2$, $RhTe_2$, $IrTe_2$, $NiTe_2$, $PdTe_2$, $PtTe_2$, or any of their modifications or combinations, including modified stoichiometry of tellurium contents having $MX_{(2-x)}$ or $MX_{(2+x)}$, wherein x is in the range of 0-1.0. In embodiments, the tellurium stoichiometry is intentionally altered so as to provide vacancy defects, interstitial defects, and aggregated defects in order to increase the surface energy of the TMD layer and enhance the adhesion of the biomolecule to the exposed TMD region. In embodiments, the TMD layer comprises $Mo_xW_yCo_z)S_2$ or $(Hf_xW_yCo_z)Te_2$. In embodiments, the conducting electrode pairs comprise at least one of Au, Pt, Ag, Pd, Rh, or their alloys. In embodiments, the nanogap is about 2 nm to about 20 nm in length. In embodiments, the TMD layer comprises a defective TMD layer. In embodiments, the defective TMD layer comprises a linear nano-ribbon parallel array, a patterned shape nano-ribbon array, strained lattice defects, vacancies, interstitial defects, dislocation defects, foreign atom implanted defects, or nanoporous defects. In embodiments, the defective TMD layer comprises strained lattice defects, vacancies, interstitial defects, dislocation defects or foreign atom implanted defects with a defect density of at least about $10^5/cm^2$. In embodiments, the defective TMD layer comprises nanoporous defects having an equivalent diameter of at least 2 nm with a defect density of at least $10^3/cm^2$. In embodiments, the defective TMD layer has a bandgap opened to a value of at least 0.2 eV.

In another aspect, a method of fabricating a sequencing device is disclosed. The method involves depositing and patterning an array of conducting electrode pairs on a dielectric substrate, each electrode paid defining a source and drain arrangement separated by a nanogap; depositing at least one TMD layer over each electrode pair; and nanopatterning a dielectric masking layer on the TMD layer. In embodiments, the method further involves processing the at least one TMD layer to obtain a defective TMD layer.

BRIEF DESCRIPTION OF THE DRAWINGS

The features and advantages of the embodiments of the present disclosure will become more apparent from the detailed description set forth below when taken in conjunction with the drawings. The drawings and the associated descriptions are provided to illustrate embodiments of the disclosure and not to limit the scope of what is claimed.

FIG. 1A illustrates linear or zig-zag shape $MoS_2$ or $WS_2$ ribbon array; FIG. 1B illustrates intentionally damaged surrounding area except for the linear ribbon regions; and FIG. 1C illustrates periodic or random defects;

FIGS. 13A-13F illustrate exemplary fabrication steps for a nanopatterned TMD bridge using diblock copolymer mask. In FIG. 13A, CVD grown, exfoliated or sulfurization activated TMD layer like $MoS_2$ or $WS_2$ on metal foil, forms the starting material. In FIG. 13B, after the metal is etched away, the TMD layer is transferred onto device surface, e.g., nano-gapped, Au, Pd or Pt electrode pair on $SiO_2$ (or $SiO_2$-coated Si substrate), to place the TMD layer as a suspended bridge. In FIG. 13C, TMD is covered by a thin layer of evaporated $SiO_2$ and a thin film of spin-coated block-copolymer PS-b-P4VP. In FIG. 13D, the PS-b-P4VP block-copolymer film is annealed and developed into a nanoscale two-phase structure, leaving the porous PS matrix as the template for subsequent patterning. In FIG. 13E, fluoride-based reactive ion etching (RIE) is used to penetrate and pattern the $SiO_2$ oxide layer, partially degrading the PS film, and to form the hard mask hole pattern out of the thin $SiO_2$. In FIG. 13F, TMD layer in the exposed hole area is etched away by $O_2$ plasma and then $SiO_2$ is removed. Finally, nanoporous TMD on $SiO_2$ is obtained, which is then patterned into a size-limited island TMD by dielectric masking for single molecule (e.g., enzyme) attachment;

FIGS. 13G-13L illustrate an embodiment of AAO membrane based nanopatterning of TMD layer like $MoS_2$ or $WS_2$ for molecular bridge sensors for DNA sequencing. FIG. 13G depicts exfoliated, CVD or sulfurization grown $MoS_2$; FIG. 13H depicts placement of $MoS_2$ on substrate; FIG. 13I depicts AAO nanohole membrane fabricated; FIG. 13J depicts AAO placed on $MoS_2$ surface; FIG. 13K depicts RIE etching of $MoS_2$ through the AAO holes, and FIG. 13L depicts nano-patterned $MoS_2$ on substrate obtained after AAO mask removal;

FIGS. 14A-14E illustrate an example evolution of mask layer being deposited on $MoS_2$, e.g., by sputtering or evaporation. As shown in FIGS. 14A and 14B, at the early stage of deposition, the mask material can have a more defective structure. The nano-pinholes via incomplete deposition such as in FIG. 14B can be used as a mask through which the $MoS_2$ can be etched to create nano-pinhole defects. As shown in FIGS. 14C and 14D, as the film gets thicker for longer period deposition, the pinholes or defects gradually gets less frequent. As shown in FIG. 14E, the incompletely deposited mask material in FIG. 14B is utilized to form nano-pinhole defects in $MoS_2$. The mask material is then removed by chemical or plasma etch.

FIG. 15A depicts a TMD layer on dielectric substrate starting material; FIG. 15B depicts coating the TMD surface with metallic nano-islands of 1-20 nm size; FIG. 15C depicts inducing diffusional reactions by heating to form altered composition defects, or nanopores in the TMD layer by differential chemical etching or RIE etching; and FIG. 15D depicts adding electrical lead wires and size-limiting dielectric layer (polymer or ceramic) to make the solid state electronic sensor for single enzyme molecule attachment and associated analytes attachment and sequencing analysis;

FIG. 16A depicts placing a TMD layer; FIG. 16B depicts irradiating TMD with ion implantation beam, plasma reactive ion etch (RIE) atmosphere, broadened optical, electron, ion or neutron beam; FIG. 16C depicts inducing defective TMD (with optional addition of post-irradiation annealing); and FIG. 16D depicts adding electrical lead wires and size-limiting dielectric mask layer (polymer or ceramic) to make the solid state electronic sensor for single enzyme molecule and associated analytes attachment and sequencing analysis. The desired density of defects in TMD layer like $MoS_2$ or $WS_2$ is at least $10^5/cm^2$, preferably at least $10^7/cm^2$;

FIG. 17A depicts s TMD layer; FIG. 17B depicts chemical etching of TMD surface; FIG. 17C depicts defective TMD (with optional addition of post-etch annealing); and FIG. 17D depicts adding electrical lead wires and size-limiting dielectric layer (polymer or ceramic) to make the solid state molecular electronic sensor for single enzyme molecule and associated analytes attachment and sequencing analysis;

FIGS. 22A-22B illustrate an exemplary three-dimensional array of molecular electronics genome-sequencing platform comprising TMD-based enzyme polymerase structure, e.g., with $MoS_2$ or $WS_2$ layer. An electrically insulating top coating (not shown) such as polymer or oxide layer (e.g., $Al_2O_3$, $SiO_2$, etc.) is applied except the exposed TMD region having enzyme polymerase structure for nucleotide attachment. FIG. 22A depicts a two-dimensional molecular electronics genome-sequencing device array is separately packaged into an individual microfluidic system, with each of the microfluidic layer stacked into a three-dimensional system, FIG. 22B depicts a two-dimensional molecular electronics genome-sequencing device arrays are stacked into three dimensional configuration but are housed in a single microfluidic system. The total number of molecular sensors can be at least 1,000, and can be as many as 1 million or more for massive parallel genome sequencing analysis.

Figure 1A:
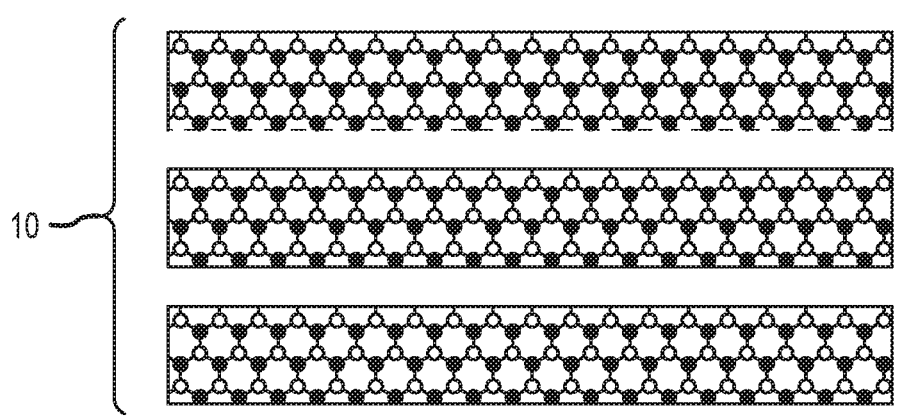
FIGS. 1A-1C illustrate example defects to be artificially introduced to a transition metal dichalcogenide (TMD) sheet such as $MoS_2$ or $WS_2$, using various techniques to provide an increased bandgap or to provide many active site edge locations for strong adhesion of bridge structures or biomolecules (such as enzyme molecules). The TMD layer can be a single layer type or few layer type.

It is to be understood that the drawings are for purposes of illustrating the concepts of the embodiments disclosed herein and are not to scale.

DETAILED DESCRIPTION

In an aspect, a new improved sequencing apparatus, structures, and methods using two-dimensional, layer structured semiconductors which provide reliable DNA and genome analysis performance and are amenable to scalable manufacturing are disclosed.

Two dimensional (2D) layered materials such as transition metal dichalcogenides (TMDs) materials and devices have received attention by virtue of their unique electronic, physical and chemical properties. An example is molybdenum dichalcogenide $MoS_2$ which can be incorporated as a sensor device. $MoS_2$ type 2D materials can be a single layered material or several layered material. The 2D layer materials such as $MoS_2$ can be produced by various known techniques, e.g., by isolation of very thin $MoS_2$ layer through mechanical exfoliation, physical or chemical vapor deposition, molecular beam epitaxy (MBE) type construction, or sulfurization of a transition metal layer such as Mo or W.

Definitions

As used herein, "bandgap" means the energy range in a solid in which electrons do not exist.

As used herein, "nano-pinhole defects" means through-hole defects with a diameter typically less than about 10 nm, which are formed during incomplete deposition of thin films. The nano-pinhole defects can be present in a mono atomic layer or a multi atomic layer, and can be configured as vertical holes or inclined holes having a circular, oval or irregular shape, As used herein, "nucleotide" means either the native dNTPs like A, T, C, G (i.e., dATP, dTTP, dCTP and dGTP), or collectively refers to various types of modified dNTPs as described above.

As used herein, "polymerase" means an enzyme that synthesizes long chains or polymers of nucleic acids. For example, DNA polymerase and RNA polymerase can copy a DNA or RNA template strand, respectively, using base-pairing interactions, which is utilized to assemble DNA and RNA molecules.

As used herein, "stoichiometry" means the relative quantities of elements in a compound.

As used herein, "van der Waals" means a residual attractive force between molecules or atomic groups that are the result of covalent or electrostatic interactions.

TMD Layers and Combined TMD Materials for Sensor Bridges

In some embodiments, a TMD layer is incorporated as a part of sensor bridge structure to attach an enzyme type biomolecule to attract various types of nucleotides for electronic detection signals.

Two dimensional transition metal dichalcogenide (TMD) monolayers are in general atomically thin semiconductors of the type $MX_2$, with M a transition metal atom (notably including Mo, W, or Ti, Zr, Hf, V, Nb, Ta, Tc, Re, Co, Rh, Ir, Ni, Pd, Pt) and X a chalcogen atom (such as S, Se, or Te.). One layer of M atoms is sandwiched between two layers of X atoms. Both the transition metal and the chalcogenide element can be partly replaced (or doped) with other elements. Therefore, the two dimensional TMD layer incorporated into the molecular sensor bridge construction can have various modified or altered composition ranges, including the following;

(i) $MoS_2$, $WS_2$, or $TiS_2$, $ZrS_2$, $HfS_2$, $VS_2$, $NbS_2$, $TaS_2$, $TcS_2$, $ReS_2$, $CoS_2$, $RhS_2$, $IrS_2$, $NiS_2$, $PdS_2$, $PtS_2$ and their modifications or combinations, including modified stoichiometry of sulfur contents having $MX_{(2-x)}$ or $MX_{(2+x)}$ with the desired value of x in the range of 0-1.0, preferably in the range of 0-0.5, even more preferably 0-0.3. For some embodiments, the sulfur stoichiometry is intentionally altered so as to provide vacancy defects, interstitial defects, and aggregated defects so as to increase the surface energy and enhance the adhesion of biomolecule to the bridge sensor. Such defects can also increase the bandgap for stronger sensor signals;

(ii) $MoSe_2$, $WSe_2$, or $TiSe_2$, $ZrSe_2$, $HfSe_2$, $VSe_2$, $NbSe_2$, $TaSe_2$, $TcSe_2$, $ReSe_2$, $CoSe_2$, $RhSe_2$, $IrSe_2$, $NiSe_2$, $PdSe_2$, $PtSe_2$ and their modifications or combinations, including modified stoichiometry of selenium contents having $MX_{(2-x)}$ or $MX_{(2+x)}$ with the desired value of x in the range of 0-1.0, preferably in the range of 0-0.5, even more preferably 0-0.3. For some embodiments, the selenium stoichiometry is intentionally altered so as to provide vacancy defects, interstitial defects, and aggregated defects so as to increase the surface energy and enhance the adhesion of biomolecule to the bridge sensor. Such defects can also increase the bandgap for stronger sensor signals;

(iii) $MoTe_2$, $WTe_2$, or $TiTe_2$, $ZrTe_2$, $HfTe_2$, $VTe_2$, $NbTe_2$, $TaTe_2$, $TcTe_2$, $ReTe_2$, $CoTe_2$, $RhTe_2$, $IrTe_2$, $NiTe_2$, $PdTe_2$, $PtTe_2$ and their modifications or combinations, including modified stoichiometry of tellurium contents having $MX_{(2-x)}$ or $MX_{(2+x)}$ with the desired value of x in the range of 0-1.0, preferably in the range of 0-0.5, even more preferably 0-0.3. For some embodiments, the tellurium stoichi-ometry is intentionally altered so as to provide vacancy defects, interstitial defects, and aggregated defects so as to increase the surface energy and enhance the adhesion of biomolecule to the bridge sensor. Such defects can also increase the bandgap for stronger sensor signals;

(iv) Mixed TMD compounds in which the $MX_2$ compound has mixed metals and/or mixed chalcogenide. For example $Mo(S_xSe_yTe_z)_2$, $W(S_xSe_yTe_z)_2$, or $Ti(S_xSe_yTe_z)_2$, $Zr(S_xSe_yTe_z)_2$, $Hf(S_xSe_yTe_z)_2$, $V(S_xSe_yTe_z)_2$, $Nb(S_xSe_yTe_z)_2$, $Ta(S_xSe_yTe_z)_2$, $Tc(S_xSe_yTe_z)_2$, $Re(S_xSe_yTe_z)_2$, $Co(S_xSe_yTe_z)_2$, $Rh(S_xSe_yTe_z)_2$, $Ir(S_xSe_yTe_z)_2$, $Ni(S_xSe_yTe_z)_2$, $Pd(S_xSe_yTe_z)_2$, $Pt(S_xSe_yTe_z)_2$ where the combined (x+y+z) is 1-3, preferably 0.5-1.5, even more preferably 0.7-1.3. Alternatively two or more metals can be combined for sulfur containing, Se-containing or Te-containing TMD layers, e.g., $(Mo_xW_yCo_z)S_2$, $(Hf_xW_yCo_z)Te_2$ and so forth; or (v) $M_{(1-w)}N_wX_{2-z}Y_z$ structure in which the transition metal M is partially substituted with non-transition elements N, with a concentration of w and the N element selected from one or more of Al, Si, Ga, Ge, In, Sn, Sb, Bi, Al, Na, K, Ca, Mg, Sr, Ba, with the w value in the range of 0-0.3, and the chalcogenide element X partially substituted with a non-chalcogenide element Y, with the Y element selected from one or more of Li, B, C, N, O, P, F, Cl, I, with the z value in the range of 0-0.3.

As the intentionally induced defects in the TMD layers of (i) to (v) described above enhances the biomolecule adhesion and sensor signal, the adhesion of biomolecule such as enzyme polymerase to the sensor bridge, is improved by using such intentionally defective TMD layer, with the probability and frequency of reliable and robust biomolecule increased by at least 20%, preferably at least 50%, even more preferably by at least 100%.

Typical thickness of a $MoS_2$ monolayer is 6.5 Å. These TMD materials in their simplest monolayer structure, e.g., $MoS_2$, $WS_2$, $MoSe_2$, $WSe_2$, $MoTe_2$, have a direct band gap, and hence can be used in electronics as transistors or sensors. Either monolayer TMD or few layer TMD can be structurally modified, to be utilized as solid state DNA or genome sensors, without labeling with optical capability. Being an ultrathin direct bandgap semiconductor, a transition metal dichalcogenide such as single-layer $MoS_2$ has found some useful applications in nanoelectronics, optoelectronics, and energy harvesting. However, not many sensor applications have been attempted or demonstrated with proper characteristics, especially for DNA or genome sequencing purposes.

Disclosed herein are label-free DNA or RNA sequencing device structures utilizing a TMD-based frame with an enzyme polymerase for detection of electronic signals when an individual nucleotide is attached onto a nucleic acid template. In some embodiments, two dimensional semiconductors of processed, defective or nanoporous Transition Metal Dichalcogenide (TMD) layer material are employed so as to utilize altered bandgaps of the TMD layer and enhanced attachment of single biomolecules. In some embodiments, the defective-TMD-based sequencing systems invented here can be assembled into a massively parallel configuration for rapid analysis of targets including nucleotides, in particular for applications of sequencing of a DNA molecule, or a collection of such molecules constituting an entire genome.

Devices

In some embodiments, a sequencing device is provided comprising: (a) an electrode array of conducting electrode pairs, each pair of electrodes comprising a source and a drain electrode separated by a nanogap, said electrode array deposited and patterned on a dielectric substrate; (b) a single-layer or few-layer thick transition metal dichalcogenide (TMD) layer disposed on each pair of electrodes, connecting each source and drain electrode within each pair, and bridging each nanogap of each pair; (c) a dielectric masking layer disposed on the TMD layer and comprising size-limited openings that define exposed TMD regions, each opening sized so as to allow only a single enzyme biomolecule to fit therein and to attach onto the exposed TMD region defined by each opening; (d) an enzyme molecule attached to each exposed TMD region such that only one enzyme molecule is found within each opening; and (d) a microfluidic system encasing the electrode array, wherein attachment or detachment of a biomolecule selected from the group consisting of a nucleotide monomer, a protein, and a DNA segment, onto the enzyme molecule, one at a time, can be monitored as a uniquely identifiable electrical signal pulse to determine the specific nature of the biomolecule attaching or detaching.

In some embodiments, the dielectric substrate comprises $SiO_2$. In some embodiments, the dielectric substrate comprises $Al_2O_3$.

In some embodiments, the TMD is selected from $MoS_2$, $WS_2$, $TiS_2$, $ZrS_2$, $HfS_2$, $VS_2$, $NbS_2$, $TaS_2$, $TcS_2$, $ReS_2$, $CoS_2$, $RhS_2$, $IrS_2$, $NiS_2$, $PdS_2$, $PtS_2$ and their modifications or combinations. In some embodiments, the TMD is $MoS_2$. In some embodiments, the TMD is $WS_2$ In some embodiments, the TMD is selected from $MoS_2$, $WS_2$, $TiS_2$, $ZrS_2$, $HfS_2$, $VS_2$, $NbS_2$, $TaS_2$, $TcS_2$, $ReS_2$, $CoS_2$, $RhS_2$, $IrS_2$, $NiS_2$, $PdS_2$, $PtS_2$ and their modifications or combinations, including modified stoichiometry of sulfur contents having $MX_{(2-x)}$ or $MX_{(2+x)}$ wherein x is in the range of 0-1.0, preferably in the range of 0-0.5, even more preferably 0-0.3. In some embodiments, the TMD is selected from $MoS_2$, $WS_2$, $TiS_2$, $ZrS_2$, $HfS_2$, $VS_2$, $NbS_2$, $TaS_2$, $TcS_2$, $ReS_2$, $CoS_2$, $RhS_2$, $IrS_2$, $NiS_2$, $PdS_2$, $PtS_2$ and their modifications or combinations and the stoichiometry of sulfur is not modified.

In some embodiments, the TMD layer comprises defects. In some embodiments, the defects are vacancy defects. In some embodiments, the defects are interstitial defects. In some embodiments, the defects are nano-pinhole pores. In some embodiments, the defects are aggregated defects so as to increase the surface energy and enhance the adhesion of the biomolecule to the bridge sensor, increasing the bandgap for stronger electrical signal pulse.

In some embodiments, the sulfur stoichiometry is intentionally altered so as to provide vacancy defects, interstitial defects, nano-pinhole defects and aggregated defects so as to increase the surface energy and enhance the adhesion of the biomolecule to the bridge sensor, increasing the bandgap for stronger electrical signal pulse.

In some embodiments, the TMD is selected from $MoSe_2$, $WSe_2$, or $TiSe_2$, $ZrSe_2$, $HfSe_2$, $VSe_2$, $NbSe_2$, $TaSe_2$, $TcSe_2$, $ReSe_2$, $CoSe_2$, $RhSe_2$, $IrSe_2$, $NiSe_2$, $PdSe_2$, $PtSe_2$ and their modifications or combinations, including modified stoichiometry of selenium contents having $MX_{(2-x)}$ or $MX_{(2+x)}$ with the desired value of x in the range of 0-1.0, preferably in the range of 0-0.5, even more preferably 0-0.3. In some embodiments, the TMD is selected from $MoSe_2$, $WSe_2$, or $TiSe_2$, $ZrSe_2$, $HfSe_2$, $VSe_2$, $NbSe_2$, $TaSe_2$, $TcSe_2$, $ReSe_2$, $CoSe_2$, $RhSe_2$, $IrSe_2$, $NiSe_2$, $PdSe_2$, $PtSe_2$ and their modifications or combinations and the stoichiometry of selenium is not modified.

In some embodiments, defects are artificially introduced into TMD. In some embodiments, the defects are introduced to increase bandgap. In some embodiments, the defects are introduced to provide active site edge locations for strong adhesion of bridge structures or biomolecules such as enzyme molecules.

In some embodiments, TMD is selected from $MoTe_2$, $WTe_2$, or $TiTe_2$, $ZrTe_2$, $HfTe_2$, $VTe_2$, $NbTe_2$, $TaTe_2$, $TcTe_2$, $ReTe_2$, $CoTe_2$, $RhTe_2$, $IrTe_2$, $NiTe_2$, $PdTe_2$, $PtTe_2$ and their modifications or combinations.

In some embodiments, TMD is selected from $MoTe_2$, $WTe_2$, or $TiTe_2$, $ZrTe_2$, $HfTe_2$, $VTe_2$, $NbTe_2$, $TaTe_2$, $TcTe_2$, $ReTe_2$, $CoTe_2$, $RhTe_2$, $IrTe_2$, $NiTe_2$, $PdTe_2$, $PtTe_2$ and their modifications or combinations, including modified stoichiometry of Tellurium contents having $MX_{(2-x)}$ or $MX_{(2+x)}$ with the desired value of x in the range of 0-1.0, preferably in the range of 0-0.5, even more preferably 0-0.3. In some embodiments, TMD is selected from $MoTe_2$, $WTe_2$, or $TiTe_2$, $ZrTe_2$, $HfTe_2$, $VTe_2$, $NbTe_2$, $TaTe_2$, $TcTe_2$, $ReTe_2$, $CoTe_2$, $RhTe_2$, $IrTe_2$, $NiTe_2$, $PdTe_2$, $PtTe_2$ and their modifications or combinations and the stoichiometry of tellurium is not modified.

In some embodiments, the tellurium stoichiometry is intentionally altered so as to provide vacancy defects, interstitial defects, and aggregated defects in order to increase the surface energy of the TMD layer and enhance the adhesion of biomolecule to the bridge sensor for stronger sensor signals.

In some embodiments, the TMD comprises a mixed TMD selected from TMD compounds in which the $MX_2$ compound has mixed metals and/or mixed chalcogenide, selected from the group consisting of $Mo(S_xSe_yTe_z)_2$, $W(S_xSe_yTe_z)_2$, $Ti(S_xSe_yTe_z)_2$, $Zr(S_xSe_yTe_z)_2$, $Hf(S_xSe_yTe_z)_2$, $V(S_xSe_yTe_z)_2$, $Nb(S_xSe_yTe_z)_2$, $Ta(S_xSe_yTe_z)_2$, $Tc(S_xSe_yTe_z)_2$, $Re(S_xSe_yTe_z)_2$, $Co(S_xSe_yTe_z)_2$, $Rh(S_xSe_yTe_z)_2$, $Ir(S_xSe_yTe_z)_2$, $Ni(S_xSe_yTe_z)_2$, $Pd(S_xSe_yTe_z)_2$, and $Pt(S_xSe_yTe_z)_2$ wherein the combined (x+y+z) is 1-3, 0.5-1.5, or 0.7-1.3.

In some embodiments, two or more metals are combined for sulfur containing, Se-containing or Te-containing TMD layers.

In some embodiments, the TMD layer comprises $Mo_xW_yCo_z)S_2$ or $(Hf_xW_yCo_z)Te_2$.

In some embodiments, the TMD comprises a $M_{(1-w)}N_yX_{(2-z)}Y_z$ structure in which the transition metal M is partially substituted with non-transition elements N, with a concentration of w and the N element selected from one or more of Al, Si, Ga, Ge, In, Sn, Sb, Bi, Al, Na, K, Ca, Mg, Sr, Ba, with the w value in the range of 0-0.3, and the chalcogenide element X partially substituted with a non-chalcogenide element Y, with the Y element selected from one or more of Li, B, C, N, O, P, F, Cl, I, with the z value in the range of 0-0.3. In some embodiments, the w value is greater than 0.3, for example, greater than 0.4, greater than 0.5, greater than 0.6, greater than 0.7, greater than 0.8, greater than 0.9, or greater than 1.0. In some embodiments, the z value is greater than 0.3, for example, greater than 0.4, greater than 0.5, greater than 0.6, greater than 0.7, greater than 0.8, greater than 0.9, or greater than 1.0.

In some embodiments, the metallic conducting electrode pair is selected from Au, Pt, Ag, Pd, Rh, or their alloys.

In some embodiments, the nanogap is 2-20 nm. In some embodiments, the nanogap is less than 2 nm, for example less than 1.5 nm, less than 1.0 nm, or less than 0.5 nm. In some embodiments, the nanogap is greater than 20 nm, for example, greater than 25 nm, greater than 30 nm, greater than 35 nm, greater than 40 nm, greater than 45 nm, or greater than 50 nm.

In some embodiments, the size-limited openings are preferably less than 30 nm average equivalent diameter each, more preferably less than 20 nm equivalent diameter, even more preferably less than 10 nm equivalent diameter, by lithographically defined coverage of dielectric material layer of polymer or ceramic outside a specific region intended for attaching only a single molecule. In some embodiments, the size-limited openings are greater than 30 nm, for example, greater than 35 nm, greater than 40 nm, greater than 45 nm, or greater than 50 nm.

In some embodiments, the size-limited openings are 30 nm equivalent diameter each, or 20 nm equivalent diameter each, or 10 nm equivalent diameter each, and wherein: (i) the TMD layer comprises an intentionally damaged structure with insulator or very high resistivity characteristics serving as the mask material to enable single molecule attachment; (i) with at least 100 ohm-cm, preferably at least 10,000 ohm-cm, even more preferably at least 1 mega ohm-cm resistivity for the regions outside a specific region intended for attaching only a single molecule; and (ii) with the intentional damaging performed by electron bombardment, laser radiation bombardment, ion bombardment, or ion implant doping.

In some embodiments, the size-limited openings are less than 10 nm equivalent diameter each and wherein: (i) the TMD layer comprises an intentionally damaged structure with insulator or very high resistivity characteristics serving as the mask material to enable single molecule attachment; (i) with at least 100 ohm-cm, preferably at least 10,000 ohm-cm, even more preferably at least 1 mega ohm-cm resistivity for the regions outside a specific region intended for attaching only a single molecule; and (ii) with the intentional damaging performed by electron bombardment, laser radiation bombardment, ion bombardment, or ion implant doping.

In some embodiments, the size-limited openings are greater than 30 nm equivalent diameter each and wherein: (i) the TMD layer comprises an intentionally damaged structure with insulator or very high resistivity characteristics serving as the mask material to enable single molecule attachment; (i) with at least 100 ohm-cm, preferably at least 10,000 ohm-cm, even more preferably at least 1 mega ohm-cm resistivity for the regions outside a specific region intended for attaching only a single molecule; and (ii) with the intentional damaging performed by electron bombardment, laser radiation bombardment, ion bombardment, or ion implant doping.

In some embodiments, the resistivity for the regions outside a specific region intended for attaching only a single molecule of any of the devices disclosed herein is greater than 1 mega ohm-cm resistivity, for example, greater than 1.5 mega ohm-cm resistivity, greater than 2.0 mega ohm-cm resistivity, greater than 2.5 mega ohm-cm resistivity, greater than 3.0 mega ohm-cm resistivity, greater than 3.5 mega ohm-cm resistivity, greater than 4.0 mega ohm-cm resistivity, greater than 4.5 mega ohm-cm resistivity, or greater than 5.0 mega ohm-cm resistivity.

In some embodiments, the TMD layer is defective with the defects selected from linear nano-ribbon parallel array, patterned shape nano-ribbon array, strained lattice defects, vacancies, interstitial defects, dislocation defects, foreign atom implanted defects, nano-pinhole defects or nanoporous defects.

In some embodiments, the size-limited TMD layer contains strained lattice defects, vacancies, interstitial defects, dislocation defects or foreign atom implanted defects with a defect density of at least $10^5/cm^2$. In some embodiments, the defect density is greater than $10^5/cm^2$, for example, greater than $10^6/cm^2$, greater than $10^7/cm^2$, greater than $10^8/cm^2$, greater than $10^9/cm^2$, or greater than $10^{10}/cm^2$.

In some embodiments, the defects in the TMD layer are nanoporous defects or nano-pinhole defects having an equivalent diameter of at least 2 nm with a defect density of at least $10^3/cm^2$. In some embodiments, the defect density is greater than $10^3/cm^2$, for example, greater than $10^4/cm^2$, greater than $10^5/cm^2$, greater than $10^6/cm^2$, greater than $10^7/cm^2$, or greater than $10^8/cm^2$.

In some embodiments, the TMD layer is defective with the bandgap opened additionally by at least 0.2 eV, preferably by at least 0.5 eV compared to the TMD without defects. In some embodiments, the TMD layer is defective with the bandgap opened additionally by greater than 0.5 eV, for example, greater than 0.6 eV, greater than 0.7 eV, greater than 0.8 eV, greater than 0.9 eV, greater than 1.0 eV, greater than 1.1 eV, greater than 1.2 eV, greater than 1.3 eV, greater than 1.4 eV, greater than 1.5 eV, greater than 1.6 eV, greater than 1.7 eV, greater than 1.8 eV, greater than 1.9 eV, or greater than 2.0 eV.

In some embodiments, the TMD layer surface exhibits hydrophilic characteristics; (i) with the hydrophilic area having a water droplet contact angle of at most 50 degrees, preferably at most 30 degrees, even more preferably at most 15 degrees; (ii) with an improved biomolecule attachment frequency with the adhesion improvement by at least 30%, preferably by at least 50%, even more preferably by at least 100% increased adhesion event as compared to the all hydrophobic TMD surface during microfluidic chamber processing of fluid supplying to provide biomolecules, nucleotides, and related biological or chemical components, as well as washing or fluid replacement operations; and (iii) the hydrophilic characteristics is associated with defects including strained lattice, vacancies, interstitials, dislocations, nanopores, foreign atom doping, with the defect density being at least $10^3/cm^2$, preferably at least $10^5/cm^2$. In some embodiments, the hydrophilic area has a water droplet contact angle of less than 15 degrees, for example, less than 14 degrees, less than 13 degrees, less than 12 degrees, less than 11 degrees, less than 10 degrees, less than 9 degrees, less than 8 degrees, less than 7 degrees, less than 6 degrees, or less than 5 degrees.

In some embodiments, the improved biomolecule attachment frequency has an adhesion improvement greater than 75%, for example, greater than 80%, greater than 85%, greater than 90%, greater than 95%, greater than 96%, greater than 97%, greater than 98%, greater than 99%, greater than 99.9%, greater than 99.99%, greater than 99.999%, or greater than 99.9999%. In some embodiments, the defect density is greater than $10^5/cm2$, for example, greater than $10^6/cm2$, greater than $10^7/cm2$, greater than $10^8/cm2$, greater than $109/cm2$, or greater than $10^{10}/cm2$.

In some embodiments, the TMD layer surface consists of a mixed structure of a hydrophilic region and a hydrophobic region, and (i) the hydrophilic area has a water droplet contact angle of at most 50 degrees, preferably at most 30 degrees, even more preferably at most 15 degrees; (ii) the area fraction of hydrophilic region is at least 10%, preferably at least 30%, even more preferably at least 50% area fraction of the exposed TMD surface to attract a single biomolecule; (iii) the hydrophilic regions are in the form of circular, oval, rectangular, or irregular islands, or in a striped configuration; (iv) the TMD surface having defects such as vacancies, interstitials, dislocations or aggregated defects, nanopores, chemically doped regions with foreign atoms, or striped pores, with the density of such defects being at least $10^3/cm^2$, preferably at least $10^5/cm^2$; (v) such a composite hydrophilic-hydrophobic configuration enables improved biomolecule attachment frequency with the adhesion improvement by at least 30%, preferably by at least 50%, even more preferably by at least 100% increased adhesion event as compared to the all hydrophobic TMD surface during microfluidic chamber processing of fluid supplying to provide biomolecules, nucleotides, and related biological or chemical components, as well as washing or fluid replacement operations; and (vi) the size of either hydrophilic islands or hydrophobic islands is desirably 1-30 nm, preferably 1-10 nm, more preferably 1-5 nm.

In some embodiments, the water droplet contact angle is less than 15 degrees, for example, less than 14 degrees, less than 13 degrees, less than 12 degrees, less than 11 degrees, less than 10 degrees, less than 9 degrees, less than 8 degrees, less than 7 degrees, less than 6 degrees, or less than 5 degrees. In some embodiments, the area fraction of the hydrophilic region is greater than 50% of the area fraction of the exposed TMD surface, for example, greater than 55%, greater than 60% percent, greater than 65%, greater than 70%, greater than 75%, greater than 80%, greater than 85%, greater than 90%, or greater than 95%. In some embodiments, the defect density is greater than $10^5/cm2$, for example, greater than $10^6/cm2$, greater than $10^7/cm2$, greater than $10^8/cm2$, greater than $10^9/cm2$, or greater than $10^{10}/cm2$.

In some embodiments, the TMD layer has tunable hydrophilicity, wherein: (i) the TMD layer is either suspended between two electrodes or fixed on top of two electrodes without suspended structural configuration; (ii) the TMD bridge surface is size-limited for attachment of single biomolecule; (iii) on-demand switching of hydrophobic to hydrophilic surface state is enabled by a device configuration of at least a pair of vertical electrodes positioned below and above the sensor bridge structure so as to apply electric field of at least 10 V/nm, preferably at least 30 V/nm to alter the semiconducting properties and widen the bandgap by at least 5%, preferably at least 10%, and make the TMD more hydrophilic with the water droplet contact angle to decrease by at least 5 degrees, preferably by at least 20 degrees for easier accommodation of microfluidic chamber environment and improved adhesion probability of single enzyme molecule such as DNA or RNA polymerase increasing by at least 30%; (iv) the electric field applied is a DC electric field or AC electric field; (v) the hydrophilic improvement is capable of being reversed to return to hydrophobic state to enable a release of previously used biomolecule and to avoid unnecessary attachment of biomolecules; and (vi) optionally having at least 1,000, preferably as many as 10,000 or even more preferably at least 1 million devices, with one or more selected electrode-paired devices simultaneously or in a series operation tunable to be hydrophilic or hydrophobic.

In some embodiments, the electric field is greater than 30 V/nm, for example, greater than 35 V/nm, greater than 40 V/nm, greater than 45 V/nm, or greater than 50 V/nm. In some embodiments, the bandgap is widened by greater than 10%, for example, greater than 15%, greater than 20%, greater than 25%, greater than 30%, greater than 35%, greater than 40%, greater than 45%, or greater than 50%.

In some embodiments, the biomolecule to be attached onto the TMD is an enzyme polymerase molecule. In some embodiments, the polymerase molecule is a RNA polymerase. In some embodiments, the polymerase molecule is a DNA polymerase.

In some embodiments, the biomolecule to be attached onto the TMD is selected from various other biopolymers of DNA, RNA, proteins, ribozyme, aptamer or polysaccharide.

In some embodiments, the two-dimensional shaped TMD layer is locally converted to three-dimensionally shaped TMD, so as to provide mechanical support for robust and reliable TMD positioning, with additional defects at the curved or kinked position with displaced or strained lattice in TMD, to produce higher-energy-state positions for enhanced adhesion of enzyme biomolecules, with the altered shape TMD having the following structural characteristics of; (i) an introduction of new modes of defects and shape discontinuity for higher-energy-state local regions; (ii) a shape-altering insert structure made of dielectric material selected from polymer materials or ceramics materials; (iii) the shape-altering insert structure having a uniformly or non-uniformly protruding structure beyond the level of metallic conductor electrode top surface so as to make the TMD layer non-flat geometry selected the configuration of being bent, curvatured, dome-shaped, irregular-shaped, buckled, or locally punctured shape and introduce displaced; (iv) the shape-altered TMD layer already possessing a defective structure comprising lattice defects of strained lattice, vacancies, interstitials, dislocations, nanopores, chemically doped regions with a defect density of at least $10^3/cm^2$; (v) the altered shape selected from hemispherical, rectangle, oval, wavy, or other periodic or irregular geometry; and (vi) the shape-altering insert permanently left underneath the TMD layer to serve as a beneficial mechanical support to guard against mechanical detachment or damage of the TMD layer during microfluidic handling of the sequencing device systems and associated inadvertent force applied to the suspended or barely bonded TMD layer on the nanogap region, or etched away to leave a mechanically compliant, protruding TMD layer.

In some embodiments, the TMD layer is in contact with the dielectric substrate with no nanogap, with a pair of metallic electrodes extended from the both ends of the TMD island as electric lead wires.

In some embodiments, the enzyme polymerase molecule connection to the TMD surface is via functional groups or functional group pairs selected from a list of streptavidin-biotin pair, antigen-antibody interaction, bifunctional ligands using mercaptocarbonic acids [HS—$(CH_2)n$—COOH, n=1-15], peptide functional groups, thiol-alkyne pair, COOH—$NH_2$ functional group pair, a thiol-maleimide azide pair, silanization linkage using mercaptosilane compounds, and a NHS (N-hydroxysuccinimide) ester-amine pair.

In some embodiments, the dNTP nucleotide being attached to the enzyme polymerase molecule is a modified nucleotide type to enhance the incorporation signals, or produce signals with enhanced differences between the different bases (A, C, G, T) incorporation events, for greater accuracy determining the template sequence, with such dNTP modifications include modifications of; (i). the base, such as 7-deaza forms, 8-bromo forms; (ii) the alpha- and beta-phosphates, such as thiolated forms or bromated forms of these phosphates; (iii) the gamma-phosphate modifications, including the addition of phosphates, such as tetra-, penta- or hexa-phosphates forms; or (iv) the groups added to the terminal phosphate.

In some embodiments, the electrode arrangement comprises a triode configuration with a gate electrode placed parallel to each of said source and drain electrodes or perpendicular to each nanogap between each of source and drain electrodes in the electrode array.

In some embodiments, the electrodes, TMD layer, masking dielectric, and enzyme molecule are arranged into an array configuration so as to allow massively parallel electronic sequencing analysis using devices organized into a system having at least 1,000, preferably at least 1 million devices. In some embodiments the system as greater than 1 million devices, for example, greater than 2 million devices, greater than 3 million devices, greater than 4 million devices, greater than 5 million devices, greater than 6 million devices, greater than 7 million devices, greater than 8 million devices, greater than 9 million devices, or greater than 10 million devices.

In some embodiments, a sequential interrogation of an array of electrodes in the TMD-containing enzyme polymerase molecular sensor is enabled for DNA or genome sequencing by using a common lead wire on one side of the array.

In some embodiments, the electrodes, TMD layer, masking dielectric, and enzyme molecule are arranged into a three-dimensional array of molecular electronics genome-sequencing platform using a stacked microfluidic chamber or a common microfluidic chamber for a stacked layer devices, so as to allow massively parallel electronic sequencing analysis using devices organized into a system having at least 1,000, preferably at least 1 million devices.

Methods

In some embodiments, a method of fabricating a TMD based DNA or genome sequencing device is provided, said method comprising: (a) providing an array of metallic conducting electrode pairs with a source and drain arrangement deposited and patterned on a dielectric substrate; (b) depositing a single-layer or few-layer TMD by using a liquid container lift-up placement method onto the electrode array, by using a vacuum transfer method, or by using a stamp transfer method; (c) nanopatterning a dielectric masking layer placed on the TMD surface with an opening which is size-limited so as to allow only a single enzyme biomolecule to attach onto the exposed TMD surface for sequencing analysis; (d) placing the sequencing device into a microfluidic system and supplying a fluid containing denaturized nucleotide molecules or modified nucleotides, and chemical agents; and (e) making an electronic measurement and computer analysis on the event of individual nucleotide monomers or modified nucleotide components attachment onto an enzyme polymerase molecule one at a time to obtain electrical pulse signals to determine the specific nature of the nucleotide being attached.

In some embodiments, the TMD layer is made defective by nanopatterning into linear nano-ribbon parallel array or patterned shape nano-ribbon array, or introducing disturbed lattice defects of strained lattice, vacancies, interstitials, dislocations, chemical doped or ion implant doped regions, or providing nanoporous defects.

In some embodiments, the defects in TMD layer are introduced by beam irradiation selected from ion implantation beam, plasma reactive ion etch (RIE) atmosphere, broadened optical, electron, ion or neutron beam, so as to introduce defect density of at least $10^5/cm^2$.

In some embodiments, the irradiated structure is post-irradiation annealed at 100-600° C. In some embodiments, the irradiated structure is post-irradiation annealed at less than 100° C. In some embodiments, the irradiated structure is post-irradiation annealed at greater than 600° C.

In some embodiments, the TMD lattice defects or nanopores or nano-pinholes are introduced by chemical etching using oxidizing chemicals, strong acids, strong alkaline solutions, so as to introduce defect density of at least $10^5/cm^2$. In some embodiments, the defect density is greater than $10^5/cm2$, for example, greater than $10^6/cm^2$, greater than $10^7/cm^2$, greater than $10^8/cm^2$, greater than $10^9/cm^2$, or greater than $10^{10}/cm^2$.

In some embodiments, the TMD with nanoporous defects are introduced by using block copolymer templated hole generation so as to introduce defect density of at least $10^5/cm^2$. In some embodiments, the defect density is greater than $10^5/cm2$, for example, greater than $10^6/cm^2$, greater than $10^7/cm^2$, greater than $10^8/cm^2$, greater than $10^9/cm^2$, or greater than $10^{10}/cm^2$.

In some embodiments, the TMD with nanoporous defects are introduced by using anodized aluminum oxide templated hole generation so as to introduce defect density of at least $10^5/cm^2$. In some embodiments, the defect density is greater than $10^5/cm^2$, for example, greater than $10^6/cm^2$, greater than $10^7/cm^2$, greater than $10^8/cm^2$, greater than $10^9/cm^2$, or greater than $10^{10}/cm^2$.

In some embodiments, the TMD with nanoporous defects are introduced by using nanoimprinting patterning so as to introduce defect density of at least $10^5/cm^2$. In some embodiments, the defect density is greater than $10^5/cm^2$, for example, greater than $10^6/cm^2$, greater than $10^7/cm^2$, greater than $10^8/cm^2$, greater than $10^9/cm^2$, or greater than $10^{10}/cm^2$.

In some embodiments, the TMD with nanoporous defects are introduced by using metallic nanoparticles spray deposited onto TMD, allowing diffusional reactions and differential chemical etching.

In some embodiments, the TMD with nano-pinhole defects are introduced by using an incomplete thin film mask deposition so as to prepare a mask with nanoscale pinholes through which the TMD layer underneath can be etched using chemical, plasma or ion bean etching method to create nano-pinhole defects. The mask material is then removed by chemical or plasma etch to expose the TMD layer with nano-pinhole defects of at least $10^5/cm^2$. In some embodiments, the defect density is greater than $10^5/cm^2$, for example, greater than $10^6/cm^2$, greater than $10^7/cm^2$, greater than $10^8/cm^2$, greater than $10^9/cm^2$, or greater than $10^{10}/cm^2$.

In some embodiments, the TMD layer material outside a specific region intended for a single biomolecule to be attached is intentionally damaged, with the crystal structure of TMD material affected and behave like an insulator or very high resistivity material with at least 100 ohm-cm, preferably at least 10,000 ohm-cam, even more preferably at least 1 mega ohm-cm resistivity using a processing methods selected from the group consisting of (i) electron beam irradiation, (ii) ion beam irradiation, (iii) optical or laser beam irradiation, (iv) particle beam irradiation, and (v) ion implantation of foreign species atoms.

In some embodiments, the TMD layer material is made to exhibit a hydrophilic state obtained by using one or more of the following processing techniques: (i) by using a plasma treatment using oxygen-containing plasma or other types of plasma containing nitrogen, chlorine, fluorine or mixed elements, or (ii) by using imperfect crystallization with defects such as strained lattice, vacancies, interstitials, dislocations nanopores or aggregated defects) in the $MoS_2$ structure (or TMD structure in general), e.g., by sulfurization anneal (or selenium or tellurium diffusion anneal process) at lower temperatures during sulfurization synthesis of TMD layer from the pre-deposited metal layer, with the process temperature selected to be lower by at least 50° C., preferably by at least 200° C. lower than the temperature for obtaining high-quality crystallization with more than 90% of the material having well crystallized TMD layer material, or (iii) by using a non-completed crystallization process with defects such as strained lattice, vacancies, interstitials, dislocations nanopores or aggregated defects) in the $MoS_2$ structure (or TMD structure in general), e.g., by sulfurization anneal (or selenium or tellurium diffusion anneal process) for shorter time periods during sulfurization synthesis of TMD layer from the pre-deposited metal layer, with the process time selected to be shorter by a factor of at least 3, preferably by a factor of 10 than the annealing time needed for obtaining high-quality crystallization with more than 90% of the material having well crystallized TMD layer material or (iv) by a deposition of a thin hydrophilic surface layer less than 10 nm thickness, such as transition metals like Ti, Zr, Hf, V, Nb, Ta, Cr, Mo, W, Mn, Fe, Co, Ni, Cu, Zn, or ceramic islands of these elements such as $TiO_2$, NiO, $Fe_2O_3$ using physical deposition, chemical deposition, electrochemical deposition, or ion implantation.

In some embodiments, the TMD layer material is made to exhibit a combined hydrophilic and hydrophilic mixed phase state obtained by using one or more of the following processing techniques; (i) by using a plasma treatment using oxygen-containing plasma or other types of plasma containing nitrogen, chlorine, fluorine or mixed elements, or (ii) by using imperfect crystallization with at least 10%, preferably at least 30% area fraction of TMD surface material having an imperfect crystal lattice configuration, with defects such as vacancies, interstitials, dislocations nanopores or aggregated defects) in the $MoS_2$ structure (or TMD structure in general), e.g., by sulfurization anneal (or selenium or tellurium diffusion anneal process) at lower temperatures and shorter times during sulfurization synthesis of TMD layer from the pre-deposited metal layer, with the process temperature selected to be lower by at least 50° C., preferably by at least 200° C. lower than the temperature for obtaining high-quality crystallization with more than 90% of the material having well crystallized TMD layer material, or (iii) by using a non-completed crystallization process with at least 10%, preferably at least 30% area fraction of TMD surface material having an imperfect crystal lattice configuration, with defects such as vacancies, interstitials, dislocations nanopores or aggregated defects) in the $MoS_2$ structure (or TMD structure in general), e.g., by sulfurization anneal (or selenium or tellurium diffusion anneal process) for shorter time periods during sulfurization synthesis of TMD layer from the pre-deposited metal layer, with the process time selected to be shorter by a factor of at least 3, preferably by a factor of 10 than the annealing time needed for obtaining high-quality crystallization with more than 90% of the material having well crystallized TMD layer material, or (iv) by a partial deposition of hydrophilic islands such as metallic islands of transition metals like Ti, Zr, Hf, V, Nb, Ta, Cr, Mo, W, Mn, Fe, Co, Ni, Cu, Zn, or ceramic islands of these elements such as $TiO_2$, NiO, $Fe_2O_3$, with an areal fraction of 5-50%, preferably at least 10%, more preferably at least 30%, using physical deposition, chemical deposition, electrochemical deposition, or ion implantation. In some embodiments, the areal fraction is greater than 50%. In some embodiments, the areal fraction is less than 10%.

In some embodiments, the tunable hydrophilic TMD layer material is produced by using the following processing method; (i) a DC or AC electric field is applied to the vertically arranged two electrodes, one above and one below the TMD layer, (ii) with the applied electric field being at least 10 V/nm, preferably at least 30 V/nm to alter the semiconducting properties, (iii) with the bandgap widened by at least 5%, preferably at least 10%, and (iv) with the TMD made more hydrophilic with the water droplet contact angle to decrease by at least 5 degrees, preferably by at least 20 degrees for easier accommodation of fluidic chamber environment and improved adhesion of single enzyme molecule such as DNA or RNA polymerase.

In some embodiments, a method of maintaining the sequencing device is provided of any of the devices described herein, wherein the device when not in use is evacuated and back-filled with inert gas so as to minimize inadvertent adhesion or adsorption of unwanted molecules.

In some embodiments, use of any of the DNA or RNA sequencing devices and systems described herein can perform a whole genome sequencing. In some embodiments, use of any of the DNA or RNA sequencing devices and systems described herein can perform partial genome sequencing.

In some embodiments, use of any of the DNA or RNA sequencing devices and systems disclosed herein can diagnose diseases. In some embodiments, use of any of the DNA or RNA sequencing devices and systems described herein can diagnose diseases such as cancer.

In some embodiments, any of the genome sequences systems described herein can be a desktop unit, a portable unit or a wearable unit.

Figure 1B:
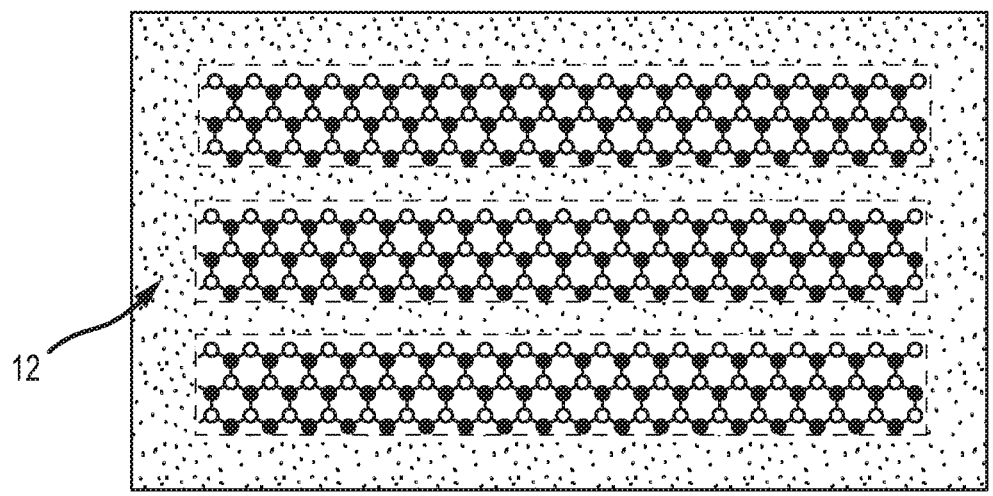
Figure 1C:
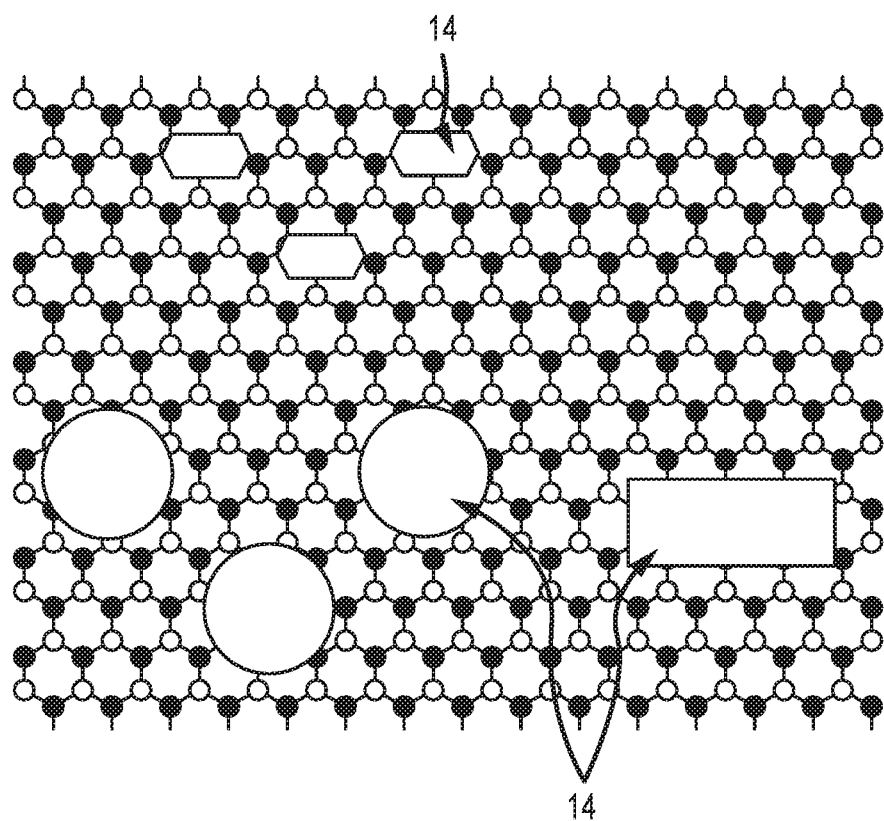

Artificially Introduced Defects and Configurations for Enhanced Biomolecule Attach and Improved Sensor Signal Referring to the drawing figures, FIGS. 1A-1C schematically illustrate examples of defects that can be artificially introduced to a TMD sheet such as $MoS_2$ or $WS_2$, using various techniques to provide an increased bandgap, and/or to provide many active site edge locations for strong adhesion of bridge structures or biomolecules (such as enzyme molecules). The TMD layer can be a single layer type or few layer type. The TMD can be narrow ribbons of linear or zig-zag shape $MoS_2$ or $WS_2$ 10 as illustrated in FIG. 1A, or can have intentionally damaged surrounding area 12 except for the linear ribbon regions, as illustrated in FIG. 1B, or can contain a multiplicity of periodic or random defects 14 as illustrated in FIG. 1C.

With reference to FIG. 1A, linear or zig-zag shape $MoS_2$ or $WS_2$ ribbon array (single layer of few layer) with nanogaps between ribbons can be obtained by nanopatterned removal of material. The edges of narrow ribbons provide favorable adhesion sites for biomolecules such as an enzyme molecule (e.g., DNA or RNA polymerase). The presence of edge defects also can increase the bandgap for more versatile semiconductor characteristics. In some embodiments, the ribbon width dimension is in the range of 1-500 nm. In some embodiments, the ribbon width dimension is in the range of 3-30 nm. In some embodiments, the gap spacing between the ribbons is in the range of 2-20 nm.

With reference to FIG. 1B, the intentionally damaged, insulating or high-resistivity surrounding areas outside the linear or zig-zag shape $MoS_2$ or $WS_2$ ribbon array regions can be introduced by electron beam radiation, ion beam radiation, or ion implantation, or other optical or particle radiations. In some embodiments, the desired width of the embedded ribbons in FIG. 1B is in the range of 1-500 nm. In some embodiments, the desired width range of the embedded ribbon is in the range of 3-30 nm. In some embodiments, the gap spacing between the ribbons is in the range of 2-20 nm.

With reference to FIG. 1C, various other types of intentionally induced defects (aside from the ribbon type or areal type defects of FIGS. 1A-1B) are generally illustrated. They can be periodic or random lattice defects (vacancy type or interstitial type, 1-20 nm size regime) artificially introduced larger-than-lattice defects (periodic or random islands, e.g., 2-200 nm size) with circular, square, rectangle or irregular-shape defects [e.g., introduced by lithographic patterning (e.g., e-beam lithography, nano-imprint lithography, template mask induced removal such as using pre-patterned diblock co-polymer membrane, anodized aluminum oxide membrane followed by plasma (or RIE) etch to remove $MoS_2$ or $WS_2$ type TMD material]. These defects can also be introduced as latent defects by intentionally damaging some the selected areas by e-beam irradiation, ion-beam irradiation, ion implantation, or other optical or particle radiations.

Process for Nanopatterning of Transition Metal Dichalcogenides Layers

Figure 2A:
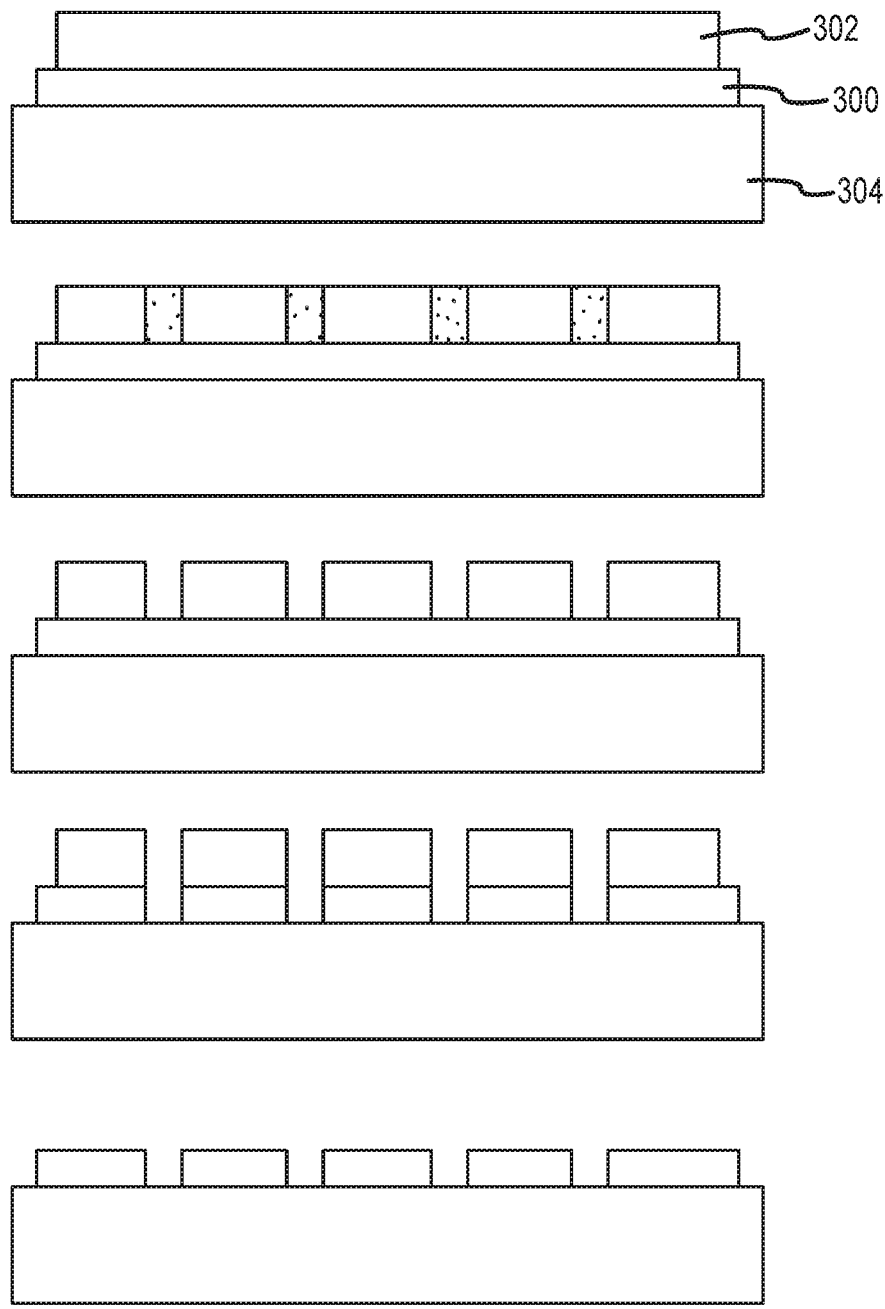
FIGS. 2A and 2B illustrate example nanopatterning processes of TMD such as $MoS_2$ or $WS_2$, using electron beam lithography (FIG. 2A) or nanoimprint lithography (FIG. 2B). In these embodiments, the TMD layer itself is physically reshaped into nanopatterns such as ribbons or islands. An alternative method is to intentionally damage the region of TMD outside the needed material area as shown in the previous figure, by using intentional disruption of crystal structure or lattice structure using e-beam, ion-beam, ion implantation, optical beam, and other radiations.
Figure 2B:
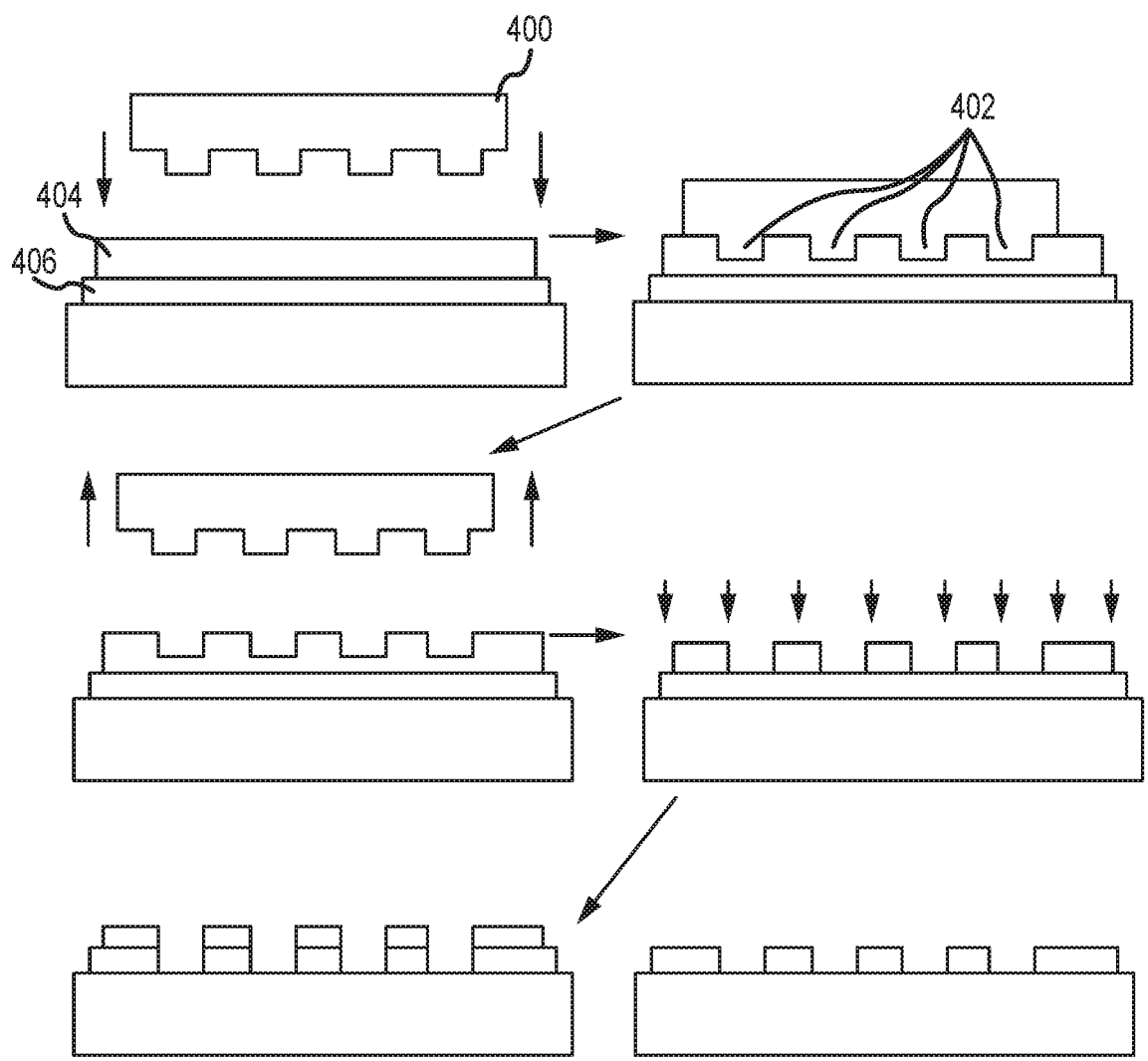

Shown in FIGS. 2A and 2B are examples of nanopatterning processes of TMD materials such as $MoS_2$ or $WS_2$, using electron beam lithography (FIG. 2A) and nanoimprint lithography (FIG. 2B). In these embodiments, the TMD layer itself is physically reshaped into nanopatterns such as ribbons or islands.

FIG. 2A illustrates the process of e-beam patterning of a $MoS_2$ 300 layer using negative or positive resist. The $MoS_2$ 300 layer (or a TNS layer in general) is coated with a resist material 302 (e.g., either a well-known positive photoresist layer such as PMMA (polymethyl methacrylate) or a negative photoresist layer such as HSQ (hydrogen silsesquioxane) or SU-8) by spin coating or thin film deposition. The photoresist is then exposed to UV light irradiation (or ion beam, neutron beam or x-ray beam irradiation in terms of general lithography), and a pattern is formed by differential developing and chemical or other process of removal of UV-reacted vs UV-unreacted local regions of the resist layer. A generally higher resolution nanopattern in the resist layer is obtained by using a negative resist than a positive resist. A short time exposure (e.g., shorter than several seconds) to UV, ion beam, neutron beam or x-ray beam irradiation, followed by a colder temperature development of the resist layer (e.g., at or below minus 10° C.) generally yields a higher resolution, e.g., sub-10 nm, and desirably sub-5nm resolution. A straight single beam or a multi-beam interference pattern may be utilized for exposure of the resist layer. The nanopatterning can be done into a periodic, non-periodic, or irregular configuration.

Once a resist pattern is obtained, the $MoS_2$ layer underneath is etched through the nanoholes in the resist layer mask by chemical etch or reactive ion etch (RIE) to selectively remove the $MoS_2$ material so as to generate a nano-patterned $MoS_2$, as shown in FIG. 2A. The left-over resist is then chemically etched away to provide a clean, nano-patterned $MoS_2$. FIG. 2B illustrates the process of nanoimprint patterning of an $MoS_2$ layer using a mold to first imprint the resist layer. An alternative method is to intentionally damage the region of TMD outside the needed material area as discussed above by using intentional disruption of crystal structure or lattice structure using e-beam, ion-beam, ion implantation, optical beam, and other radiations. In the nanoimprint processing, a premade, nanosized mold 400 (or a nano-stamp) is prepared first, e.g., by UV, ion beam, neutron beam or x-ray beam irradiation. The nanostamp is then utilized so as to mechanically impress into the resist layer 402, preferably by pre-heating the resist layer to close to the glass transition temperature where the polymer resist becomes soft for easier mechanical imprinting. The imprint-patterned resist is then subjected to a reactive ion etching (RIE) until the bottom substrate, in this case, the $MoS_2$ layer, is exposed to the chemical or RIE etching to pattern and etch the $MoS_2$ layer. The residual resist layer is then chemically etched away.

Figure 3A:
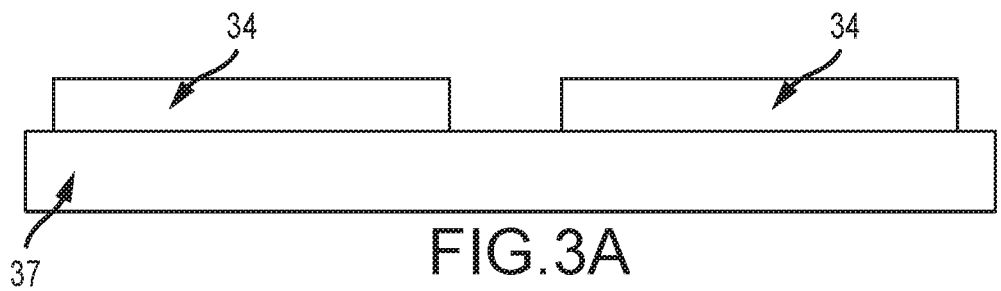
FIGS. 3A-3D illustrate an embodiment of fabrication of an exemplary molecular bridge of DNA or RNA sensor comprising size-limited, $MoS_2$ islands (TMD islands in general), comprising depositing and patterning conducting electrode pair (source and drain) (FIG. 3A), placing a suspended $MoS_2$ layer (FIG. 3B), adding a protective dielectric coating (FIG. 3C), allowing preferably a single molecule enzyme (polymerase) to attach onto the $MoS_2$, and enabling each of the polymerase reaction of nucleotide attachment (nucleotide monomers like A, T, C, G, U etc.) to change electrical properties of the molecular bridge for sequencing analysis (FIG. 3D)
Figure 3B:
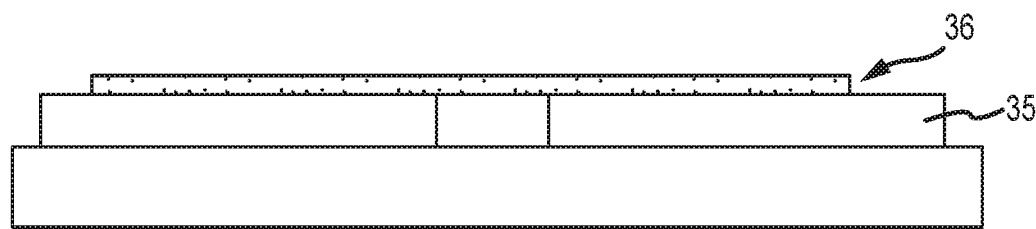
Figure 3C:
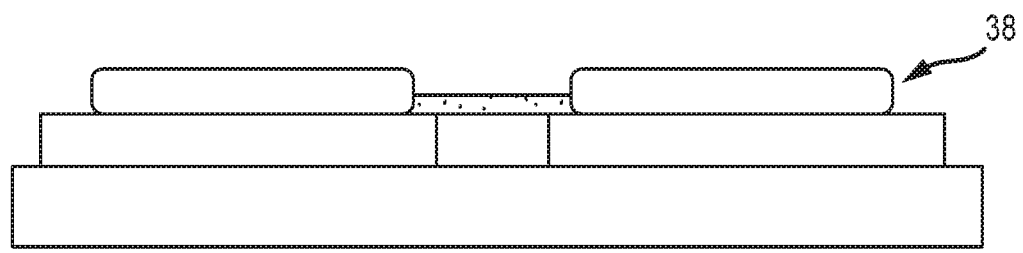
Figure 3D:
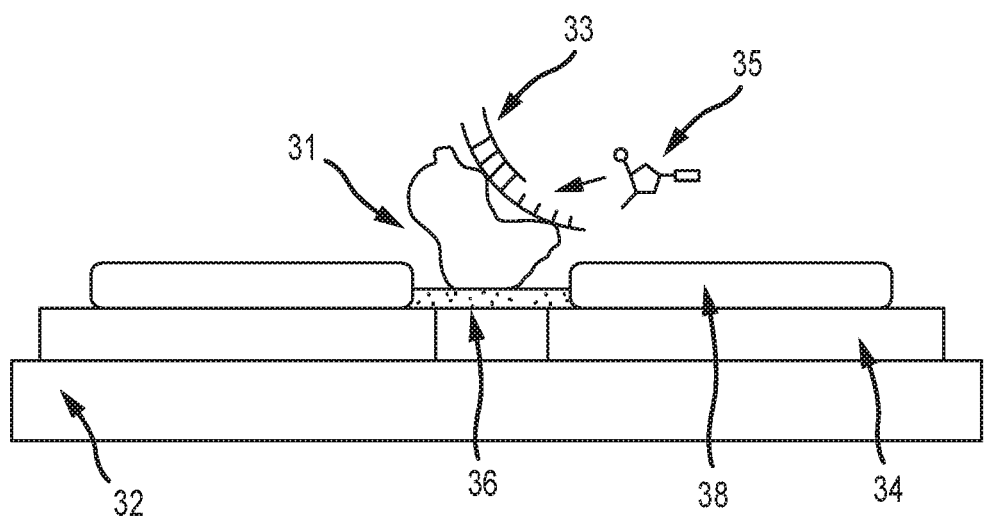

Molecular Bridge Sensor Construction using Size-Limited Exposed TMD Layers for Single Biomolecule Only Attachment onto the Sensor Bridge Referring to the drawings, FIGS. 3A-3D represent fabrication steps to create an exemplary molecular bridge of DNA or RNA sensor comprising size-limited, $MoS_2$ islands (TMD islands in general). FIG. 3A illustrates the deposit and patterning of conducting electrode pairs 34 (pairs of source and drain electrodes). As illustrated, conducting electrode pairs 35 (Au, Pt, Ag, Pd, Rh, or their alloys, for signal detection), each pair consisting of a source and drain electrode separated by a "nanogap, (e.g., 2-20 nm)" are deposited and patterned on a dielectric substrate 37 such as $SiO_2$ or $Al_2O_3$. Then, as illustrated in FIG. 3B, a $MoS_2$ layer 36 (or TMD transition metal dichalcogenide layer in general) is suspended over the nanogap to physically connect source and drain electrodes within each pair of electrodes. This TMD layer may have a regular or narrow-ribbon configuration, or may intentionally be made defective. The TMD layer may be nanopatterned by nanoimprinting or e-beam lithography if needed. FIG. 3C illustrates the step of adding a protective dielectric coating 38 over the $MoS_2$ layer. The dielectric coating is protective and size-limiting, and may be a polymer such as PMMA, or a ceramic layer like $SiO_2$. The dielectric layer 38 size limits the $MoS_2$ layer to exposed areas measuring about 2-20 nm such that a single biomolecule can fit within the limitation and bind to the exposed $MoS_2$ layer (e.g., polymerase enzyme attachment). Lastly, FIG. 3D illustrates allowing, preferably, only a single enzyme molecule 31 (e.g. a DNA or RNA polymerase) to attach onto each exposed size-limited areas of $MoS_2$ 36 and bind thereon, to enable each of the nucleotide 35 attachment (nucleotide monomers like A, T, C, G, U, etc.) in the polymerase reaction 33 to change electrical properties of the molecular bridge for sequencing analysis. As illustrated in FIG. 3D, a molecular bridge solid state sensor on a $MoS_2$ island is used for genome or DNA sequencing via detection of a change of current pulse or other signal upon attaching or detaching of a nucleotide 35 or other biomolecule to the single enzyme molecule 31.

In further detail, a conducting electrode pair (e.g., made of highly conductive and corrosion resistant metals such as Au, Pt, Ag, Pd, Rh, or their alloys), (FIG. 3A), is deposited and patterned on the surface of a dielectric substrate like $SiO_2$, $Al_2O_3$, or a Si substrate with a relatively thick insulator layer of $SiO_2$, $Al_2O_3$, coated on the surface. A nanogap of e.g., 2-20 nm is provided between the two metal lead wires serving as a source and a drain. A suspended TMD like $MoS_2$ layer (regular $MoS_2$ or preferably a $MoS_2$ structure intentionally made defective) is added over the electrode gap as shown in FIG. 3B. One example technique is to get the TMD layer floated on the surface of water or alcohol, and the substrate (with a pre-patterned metal electrode pair) is lifted up from underneath the water or alcohol to collect the TMD layer, followed by a drying procedure.

The TMD sheet is then coated with a protective dielectric coating (e.g., polymer layer like PMMA or ceramic layer like $SiO_2$) and patterned, as illustrated in FIG. 3C, to limit the exposed area of the TMD to nanometer regime island geometry (e.g., 3-30 nm average size). The dimensional limitation allows preferably only a single molecule enzyme 31 (e.g. polymerase) to attach onto the TMD layer, FIG. 3D, preventing a multiple molecule attachment and signal mix-up, and enable each of the enzyme molecules (like DNA or RNA polymerase) to react with a nucleotide 35 to attach onto the polymerase (nucleotide monomers like A, T, C, G, U etc.) to detectably change electrical properties of the molecular bridge for sequencing analysis. The desirable dimension of size-limited exposed TMD layer is preferably less than 30 nm average equivalent diameter, more preferably less than 20 nm equivalent diameter, even more preferably less than 10 nm equivalent diameter, by lithographically defined coverage of dielectric material layer of polymer or ceramic outside a specific region intended for attaching only a single molecule. The size-limited region can have a circular shape, oval shape, square or rectangular shape, or irregular shape, with the equivalent diameter defined here as the calculated diameter of a corresponding equal-area sized circle.

As described and detailed herein, a polymerase is an enzyme that synthesizes long chains or polymers of nucleic acids. For example, DNA polymerase and RNA polymerase can copy a DNA or RNA template strand, respectively, using base-pairing interactions, which is utilized to assemble DNA and RNA molecules. When a particular type of nucleotide or other biomolecule is attached to the enzyme polymerase biomolecule, a unique pulse current signal is generated which provides information on what type of nucleotides is being attached or detached. Part of the sequencing operation includes the nucleotide attachment to form a double-strand DNA associated with the enzyme polymerase.

The biomolecule to be attached on the TMD includes, in addition to various enzyme molecules, various other polymers, DNA, RNA, proteins, ribozyme, aptamer or polysaccharide. Other single molecule functionalizations of these defective TMD structures can provide sensors for other applications besides genome sequencing. For example, an enzyme other than polymerase can be attached, creating a sensor for the activity of that enzyme. This can be used to sense the presence of the enzyme substrate, and can also be used to characterize the precise kinetics of the enzyme, for application to enzyme evolution, selection and optimization. If a single molecule binding probe is attached to the defective TMD, such as a single stranded DNA or RNA oligomer hybridization probe, or an antibody against an antigen, or a protein that engages in a protein-interaction binding, this can be used to sense the binding events, and thus acts as a sensor for the presence of the binding target.

Modified dNTPs for Enhanced Sequencing Applications of Bridge Molecules

For DNA or genome sequencing applications, the bridge molecule may be conjugated to a polymerase, bound with a primed single-stranded template DNA as shown specifically be element 33 in FIG. 3D, and provided with a buffer containing nucleotides, dNTPs (deoxynucleotide triphosphates) for incorporation. Electric current through the bridge molecule is monitored as dNTPs are incorporated to synthesize the complementary strand of the template DNA. In the preferred embodiment, native dNTPs like A, T, C, G are used (dATP, dTTP, dCTP and dGTP).

In another embodiment, any or all of these may be replaced by corresponding modified dNTPs, having various molecular modifications that may enhance the incorporation signals, or produce signals with enhanced differences between the different base (A, C, G, T) incorporation events, for greater accuracy determining the template sequence. Such dNTP modifications could include: modifications of the base, such as 7-deaza forms, 8-bromo forms, or modification of the alpha- and beta-phosphates, such as thiolated forms or bromated forms of these phosphates, or gamma-phosphate modifications, including the addition of phosphates, such as tetra-, penta- or hexa-phosphates forms.

In addition, modifications may include groups added to the terminal phosphate, and it is known that the polymerase is highly tolerant of many diverse groups added to the terminal phosphate, thus providing a large class of modified dNTPs for these purposes. The use of such modified dNTPs to enhance signals does not require any labeling of the template DNA, or any other use of labels; instead, the modified molecular forms modify the conductivity properties of the complex, and thereby directly enhance the resulting electronic detection signals. Throughout this disclosure, whenever the expression "nucleotide" is used, it refers to either the native dNTPs like A, T, C, G (i.e., dATP, dTTP, dCTP and dGTP), or collectively refers to various types of modified dNTPs as described above.

Array Structure of Size-Limited TMD Sensor Bridges

Figure 4:
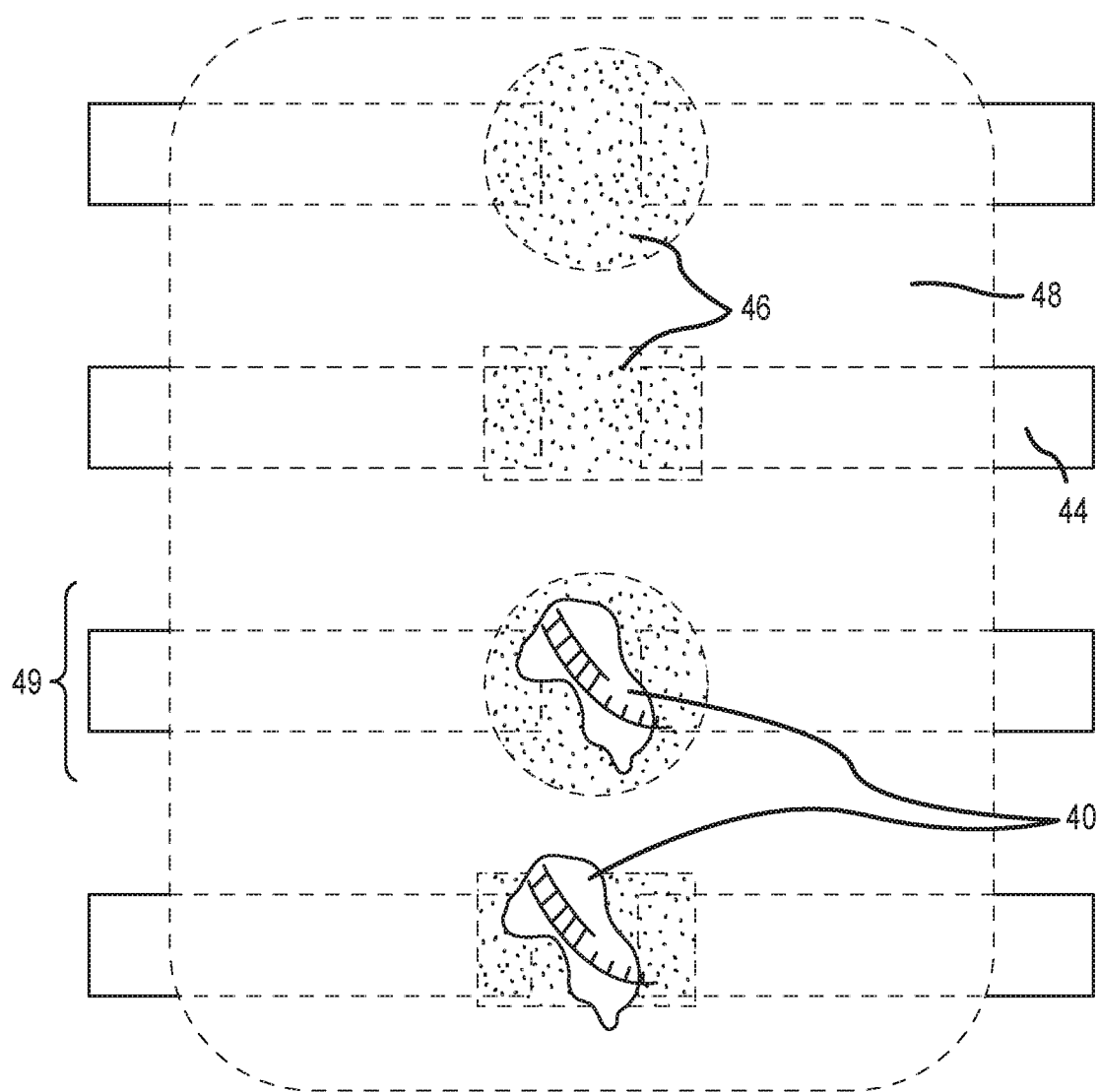
FIG. 4 illustrates the top view of an array of TMD bridges like $MoS_2$ or $WS_2$ bridge molecular sensors, with the TMD positioned as a suspended layer or substrate-adhered layer. The enzyme polymerase molecule is shown only on the lower two electrode pairs. Massively parallel electronic sequencing analysis can be performed with many devices organized into a system, having as many as 10,000 or even at least 1 million devices.

Shown in FIG. 4 is the top view of an array of TMD bridges like $MoS_2$ or $WS_2$ bridge molecular sensors, with the TMD positioned as a suspended layer or substrate-adhered layer. FIG. 4 illustrates individual units of molecular bridge sensors comprising a $MoS_2$ or $WS_2$ layer bridge 49. The exposed island region is surrounded by a patterned defined dielectric coating mask 48 (e.g., PMMA, PDMS, other adhesion-impeding polymer layer or SiO2 etc.) to prevent/minimize biomolecule attachment. The molecular bridge sensors comprise conducting electrodes and lead wires 44. The enzyme polymerase 40 molecule is shown only on the lower two electrode pairs. Size-limited (circular, oval, rectangular, square, or other shape) and locally exposed TMD like MoS2 or WS2 46 are shown on the upper two electrode pairs. Massively parallel electronic sequencing analysis can be performed with many devices organized into a system, having as many as 10,000 or even at least 1 million devices. Size-limited (circular, oval, rectangular, square, irregular or other shape) and locally selectively exposed TMD like $MoS_2$ or $WS_2$ (preferably defective or porous). A large TMD sheet can be placed by lifting up of floating TMD layer sheet onto device surface covering many pairs of electrodes, and then mask patterned. The exposed island region is surrounded by a pattern-defined dielectric coating mask (e.g., PMMA, PDMS, other adhesion-impeding polymer layer or $SiO_2$ etc.) to prevent/minimize biomolecule attachment.

Figure 5A:
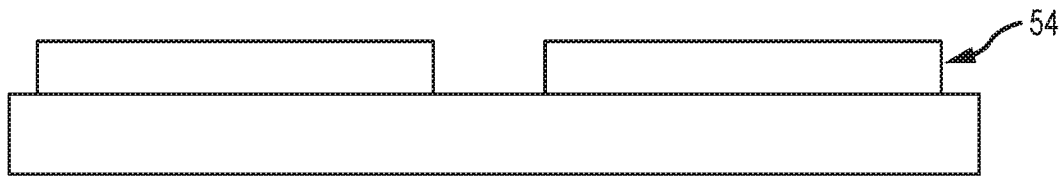
FIGS. 5A-5D illustrate an embodiment of fabrication steps for an exemplary molecular bridge of DNA or RNA sensor comprising size-limited, $MoS_2$ islands (TMD islands in general), comprising: depositing and patterning conducting electrode pairs (source and drain) (FIG. 5A), placing a suspended $MoS_2$ layer (FIG. 5B), intentionally altering the TMD except the central masked regions by irradiation or doping to make it insulating or highly resistive (FIG. 5C), allowing preferably a single molecule enzyme (polymerase) to attach onto the $MoS_2$, and enable each of the polymerase reaction of nucleotide attachment (nucleotide monomers like A, T, C, G, U, etc.) to change electrical properties of the molecular bridge for sequencing analysis (FIG. 5D)
Figure 5B:
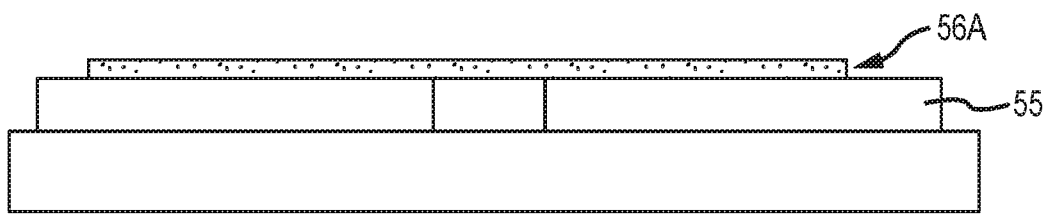
Figure 5C:
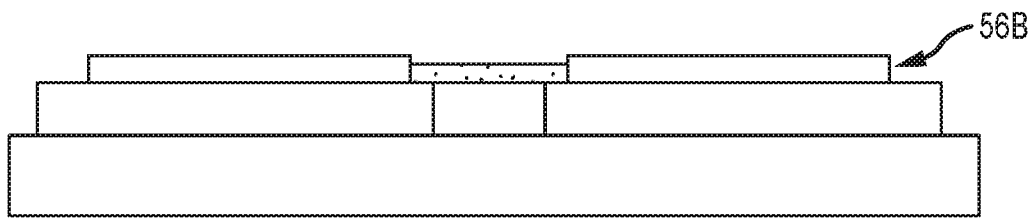

FIGS. 5A-5D illustrate various embodiments of fabrication steps usable to create an exemplary molecular bridge of DNA or RNA sensor comprising size-limited, $MoS_2$ islands (TMD islands in general). First, and as shown in FIG. 5A, a conducting electrode pair 54 (source and drain) is deposited and patterned on a substrate, with each source and drain electrode spaced apart by a nanogap. The conducting electrode pair may comprise Au, Pt, Ag, Pd, Rh, or their alloys, for signal detection, and the nanogap may be in the range of about 2-20 nm. As illustrated in FIG. 5B, a suspended $MoS_2$ layer 56A (or transition metal dichalcogenide layer in general), having either a regular structured or defective $MoS_2$, is placed on the electrode pair, suspended across the nanogap. Then, as shown in FIG. 5C, the outer regions of the TND layer 56A like $MoS_2$ or $WS_2$ is intentionally damaged to convert the layer to the damaged layer 56B. This is accomplished by, for example, doping with ion implantation or by bombardment with electrons or other radiation, converting select regions of the layer to an insulator or to very high resistivity areas so as to serve as an effective mask to enable a single biomolecule (e.g., polymerase enzyme) attachment.

Figure 5D:
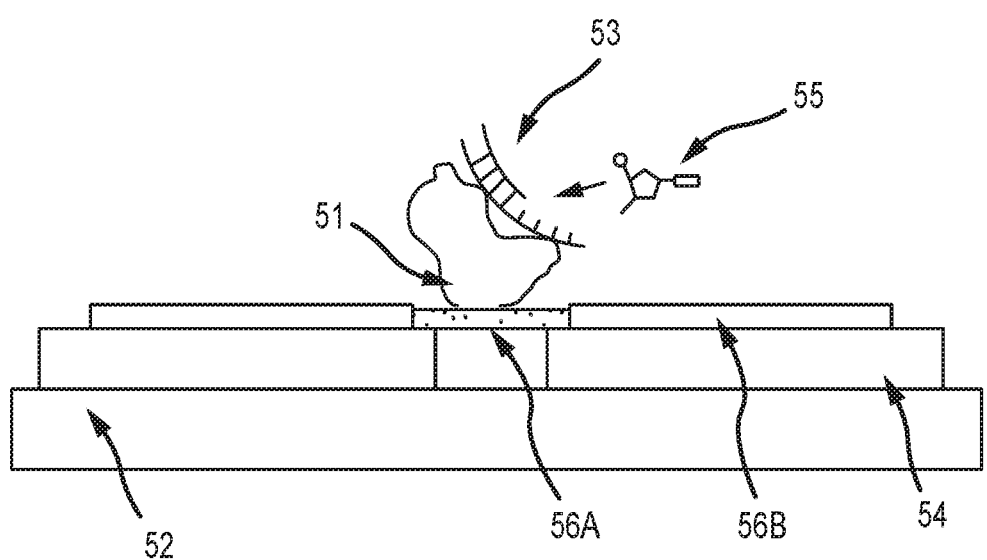

The schematic in FIG. 5D describes a single molecule enzyme 51 (polymerase) to attach onto the $MoS_2$ molecular bridge solid state sensor on the $MoS_2$ island 56A for genome or DNA sequencing via detection of change of current pulse or other signals upon attaching or detaching of nucleotide 55

(nucleotide monomers like A, T, C, G, U etc.) or other biomolecules during sequencing of the double stranded nucleic acid 53.

Figure 6A:
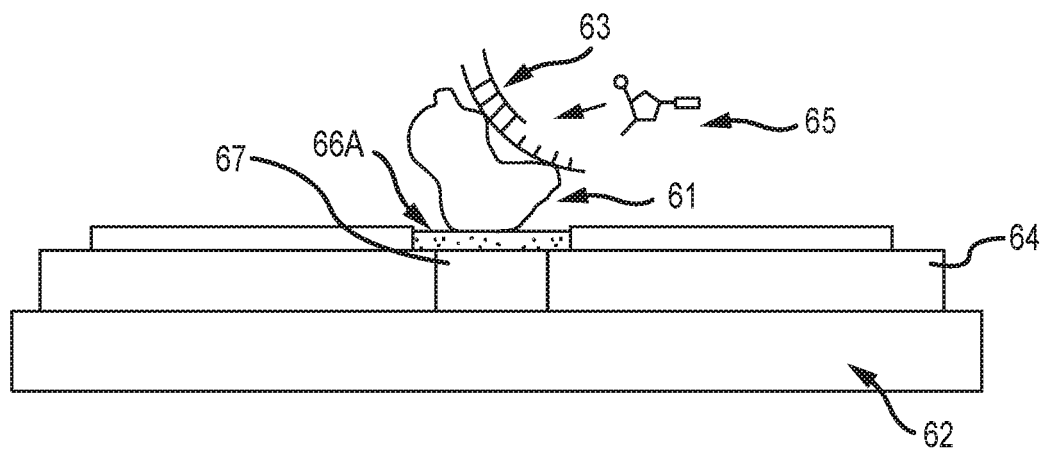
FIGS. 6A-6C illustrate exemplary embodiments of two configurations of TMD such as $MoS_2$ or $WS_2$ bridge placement as a suspended TMD bridge (FIG. 6A), and a substrate-adhered TMD bridge (FIG. 6B). A top view of the TMD bridge structure with attached polymerase enzyme is also shown in FIG. 6C. Top view shows that the single molecule enzyme (polymerase) on TMD enables each of the polymerase reaction of nucleotide attachment (nucleotide monomers like A, T, C, G, U, etc.) to change electrical properties of the molecular bridge for sequencing analysis.
Figure 6B:
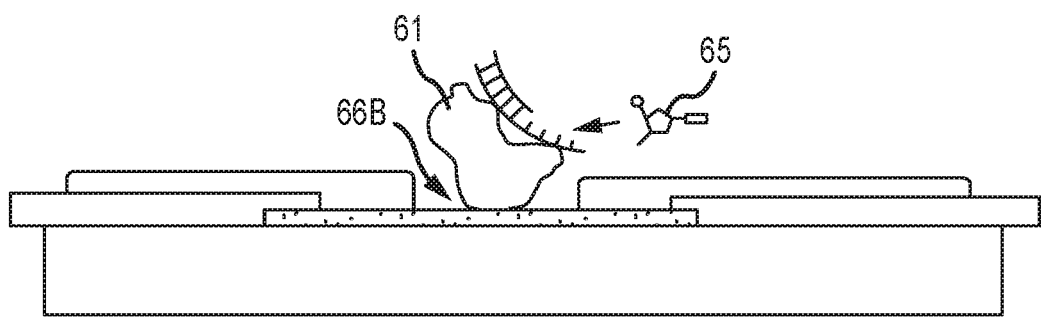
Figure 6C:
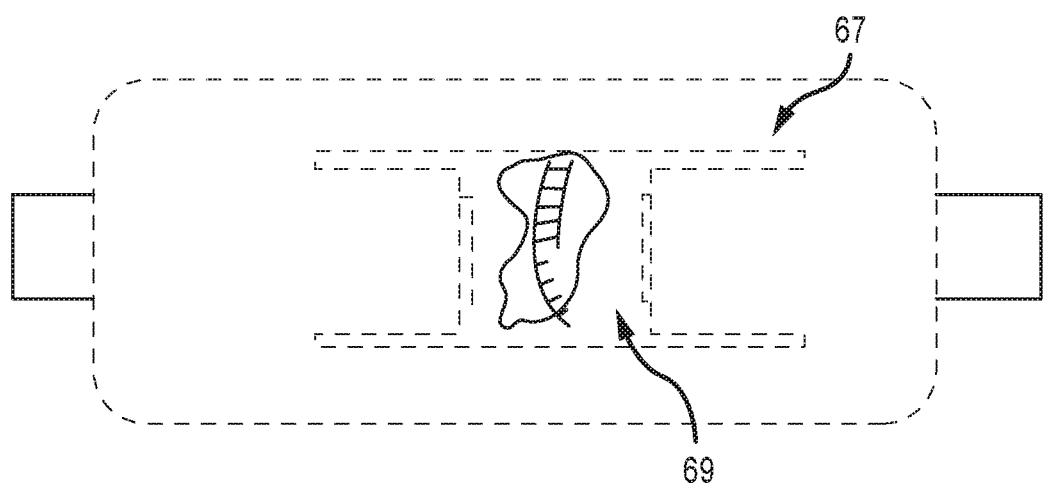

Suspended Configuration vs. Substrate-Adhered TMD Bridge Structures for Sequencing Presented in FIGS. 6A-6C are exemplary embodiments of two configurations of TMD, such as $MoS_2$ or $WS_2$, bridge placement. The schematic in FIG. 6A illustrates a suspended TMD bridge 66A while that in FIG. 6B shows a substrate-adhered TMD bridge 66B. A conducting electrode pair 64 comprising a nanogap 67 is positioned on a dielectric substrate 62 (FIG. 6A). A single enzyme molecule 61 (e.g., DNA or RNA polymerase) is attached onto a suspended TMD bridge 66A (FIG. 6A). A nucleotide monomer 65 (A, T, C, G, U, etc.) is detected upon attachment to the double stranded DNA strand 63 (FIG. 6A). A conducting electrode pair is positioned on a dielectric substrate (FIG. 6B). A single enzyme molecule 61 (e.g., DNA or RNA polymerase) is attached onto a substrate-adhered TMD bridge 66B (FIG. 6B). A nucleotide monomer 65 (A, T, C, G, U, etc.) is detected upon attachment to the double stranded DNA strand (FIG. 6B). A $MoS_2$ layer (preferably defective or porous) sheet is patterned by e-beam or preferably nano-imprinting lithography and plasma etched, and then is masked by dielectric (e.g., PMMA or adhesion-impeding polymer layer) to prevent biomolecule attachment. A top view of the TMD bridge structure with attached polymerase enzyme is shown in FIG. 6C. The top view shows that the single molecule enzyme (polymerase) on TMD enables each of the polymerase reaction of nucleotide attachment (nucleotide monomers like A, T, C, G, U, etc.) to change electrical properties of the molecular bridge for sequencing analysis. The $MoS_2$ sheet 67 (preferably defective or porous) is patterned. The size-limiting of locally exposed $MoS_2$ region 69 (circular, square, or other shape), preferably as a defective or porous sheet, for single molecule attachment (e.g., 2-20 nm width), can be accomplished, e.g., by nanoimprint lithography with associated ion plasma etching. This method is preferred over e-beam lithography in order to minimize e-beam damage of the TMD layers.

Use of Functionalization for Biomolecule Bonding

The defective TMD also allows an easy and strong bonding with biomolecules as the TMD edges and defects provide many active sites for atomic bonding and chemical bonding. While a direct adhesion of biomolecules such as enzyme polymerase molecule is more desirable for simpler structuring and less interfacial electrical resistance, embodiments herein not exclude a use of functional bridging to ensure stronger attachment of biomolecules onto TMD. In addition to the direct bonding of the enzyme polymerase biomolecule onto the TMD surface, such a bonding can alternatively be achieved using functionalized ligands.

Figure 7A:
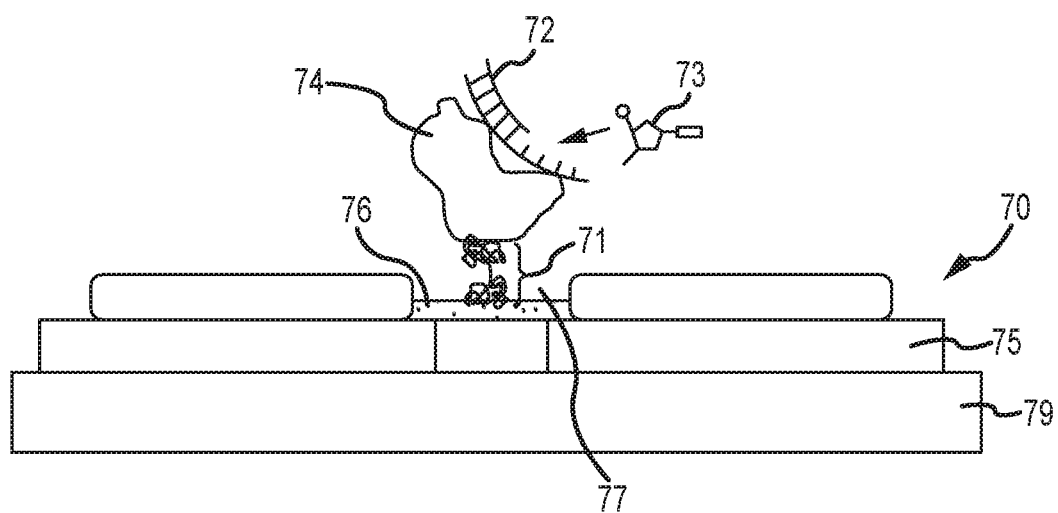
FIGS. 7A and 7B illustrate enzyme molecule connection to a TMD bridge via functional groups, with two resulting exemplary embodiments of a solid state molecular sensor, based on a suspended TMD bridge (FIG. 7A), and a substrate-adhered TMD bridge (FIG. 7B). Preferably a defective or porous TMD layer is utilized, which is masked to a limited size area (e.g., 2-20 nm) to enforce a single molecule attachment using a patterned dielectric coating (e.g., PMMA, PDMS or other adhesion-impeding polymer layer or $SiO_2$ layer)
Figure 7B:
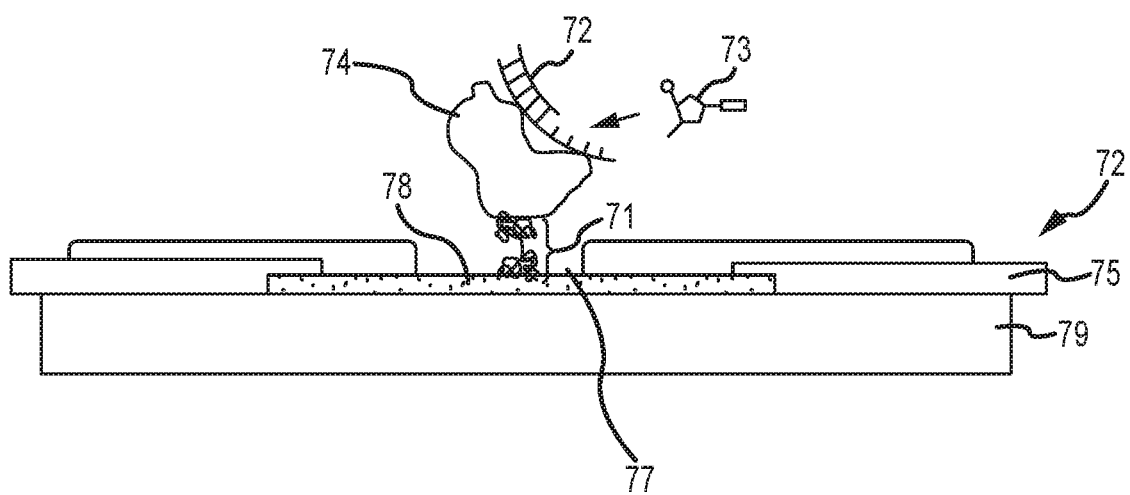

The enzyme molecule connection to TMD may be via functional groups or ligands. FIGS. 7A and 7B illustrate two exemplary embodiments of a solid state molecular sensor, based on enzyme attachment to a suspended TMD bridge (FIG. 7A) and enzyme attachment to a substrate-adhered TMD bridge (FIG. 7B). The sensors can be used for genome or DNA or RNA sequencing detection via change of current or other signals upon attaching or detaching of nucleotide or other biomolecules. FIG. 7A illustrates a molecular bridge solid state sensor 70 for genome or DNA or RNA sequencing detection via change of current or other signals upon the attachment or detachment of individual nucleotide monomers or other biomolecules. FIG. 7B illustrates an embodiment of a molecular bridge sensor 72 with the TMD layer affixed onto the dielectric substrate via Van der Waals forces and the dielectric coating disposed above it. In some embodiments, a defective or nanoporous TMD layer is used, such as $MoS_2$ or $WS_2$, which is masked to limited size areas (e.g., 2-20 nm each), to enforce only a single molecule attachment per each limited size area, such as by using a patterned dielectric coating (e.g., PMMA, PDMS or other adhesion-impeding polymer layer or $SiO_2$ layer). An enzyme molecule 74 (e.g., DNA or RNA polymerase is linked to a suspended TMD bridge such as $MoS_2$ or $WS_2$ 76 (FIG. 7A). Alternatively, an enzyme molecule 74 (e.g. DNA or RNA polymerase) is linked to a substrated-adhered TMD bridge 78 (FIG. 7B). Functionalization paired groups 71 that can be optionally used to link enzyme molecule to TMD include, e.g., streptavidin-biotin pair, antibody-antigen interaction, bifunctional ligands using mercaptocarbonic acids [HS—$(CH_2)n$—COOH, n=1-15], peptide functional groups, antibody-antigen pair, thiol-alkyne pair, COOH—$NH_2$ functional group pair, a thiol-maleimide azide pair, silanization linkage using mercaptosilane compounds, and a NHS (N-hydroxysuccinimide) ester-amine pair. Nucleotide monomers 73 (A, T, C, G, U, etc.) are detected as they are added to the DNA strand. Conducting electrodes and lead wires 75 (Au, Pt, Ag, Pd, Rh, or their alloys, etc.) are used for signal detection. The sensors comprise a dielectric substrate 79 ($SiO_2$, $Al_2O_3$, etc.) and a nanogap 77.

Figure 8A:
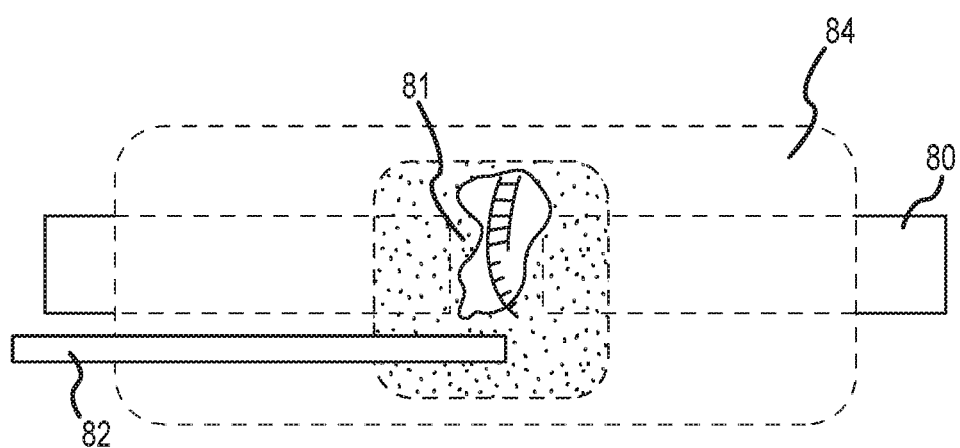
FIGS. 8A and 8B illustrate embodiments of gated structure sequencing devices of TMD bridge like $MoS_2$ or $WS_2$, with the gate electrode placed as parallel to the source and drain electrodes (FIG. 8A), or perpendicular to the nanogap spacing between the two (source and drain) electrodes (FIG. 8B). The tip of the gate electrode can also be placed above or below the nanogap.
Figure 8B:
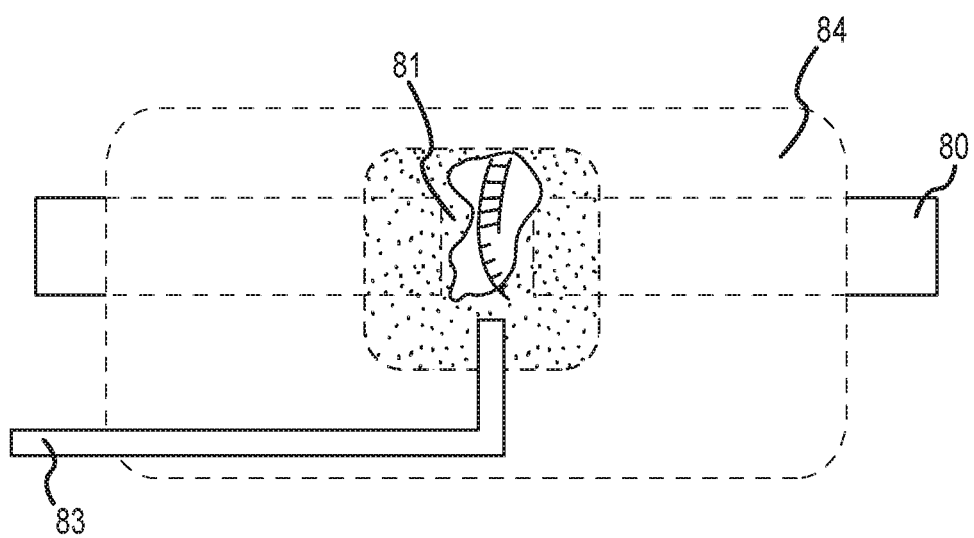

FIGS. 8A and 8B illustrate embodiments of TMD-containing molecular bridge sensors usable for sequencing detection that further comprise a third electrode operating as a gate electrode. Gated structure of TMD bridge sequencing devices may comprise disposition of the gate electrode positioned parallel to the source and drain electrodes 80 (FIG. 8A) or perpendicular to the nanogap spacing 81 between the two (source and drain) electrodes (FIG. 8B). In FIG. 8A, the gate electrode 82 is facing the device junction in a parallel geometry for triode type sensor operation. In FIG. 8B, the gate electrode 83 is facing the device junction in a perpendicular way for triode type sensor operation. The TMD or $MoS_2$ or $WS_2$ (defective or porous TMD) sheet is masked by a dielectric surrounding 84 to prevent biomolecule attachment. The dielectric masks TMD except in a selected limited area. The conducting electrodes (source & drain) contain a nanogap (e.g., 2-50 nm). The tip of the gate electrode can also be placed above or below the nanogap. In either embodiment illustrated, the TMD bridge may comprise $MoS_2$ or $WS_2$.

Intentionally Damaged Surrounding TMD Region

Figure 9:
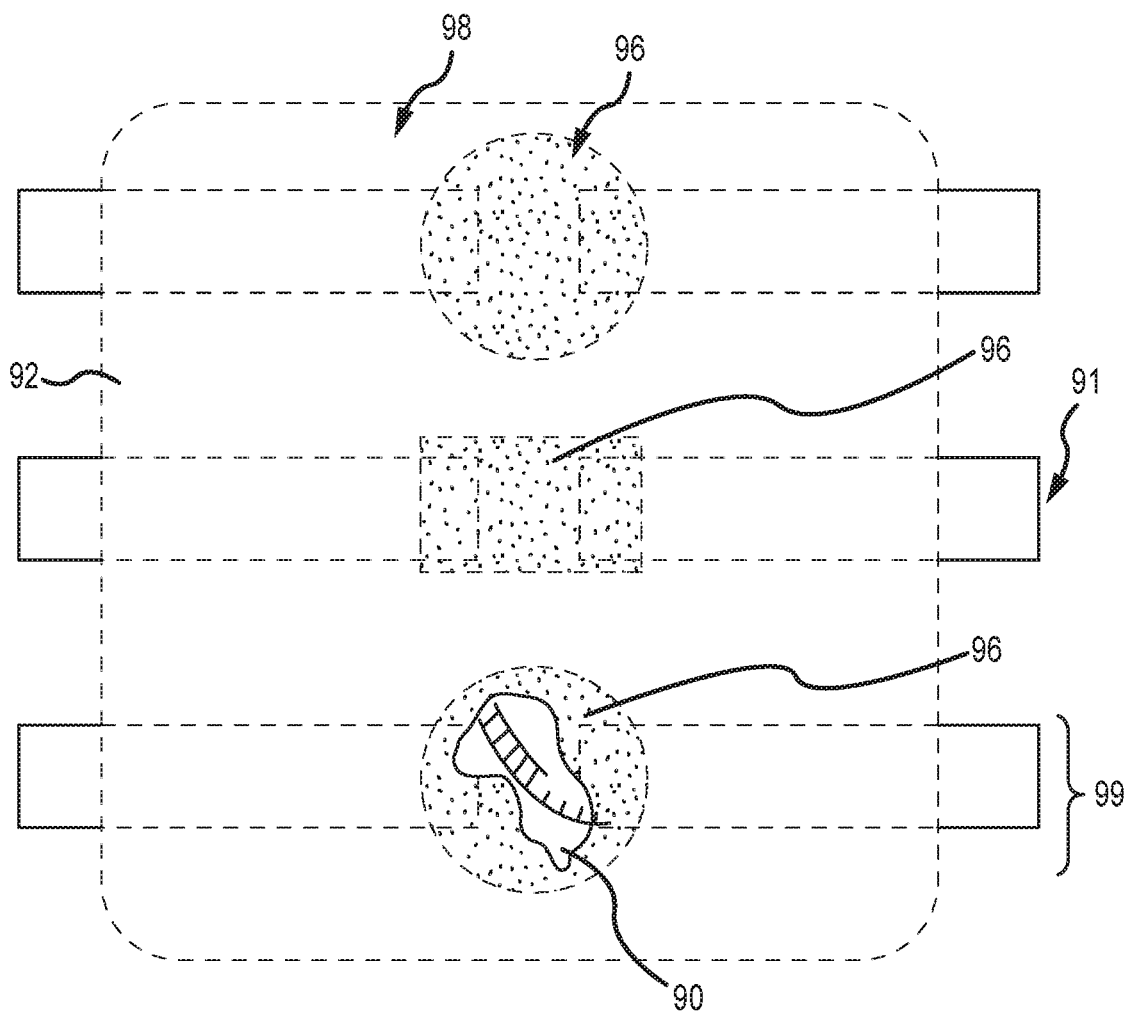
FIG. 9 illustrates a top view of an array of TMD bridge molecular sensors like $MoS_2$ or $WS_2$ with the TMD positioned as a suspended layer or substrate-adhered layer. The enzyme polymerase molecule is shown only on the lowest electrode pair of the array. Massively parallel electronic sequencing analysis can be performed with many devices organized into a system, having as many as 10,000 or even at least 1 million devices.

FIG. 9 illustrates a top view of an array of TMD bridge molecular sensors like $MoS_2$ or $WS_2$ with the TMD layer positioned as a suspended layer or substrate-adhered layer. The enzyme polymerase molecule 90 is shown only on the lowest molecular bridge sensor 99, comprising a $MoS_2$ layer bridge. FIG. 9 comprises units of molecular bridge sensors comprising a $MoS_2$ layer bridge 99. Each molecular sensor comprises conducting electrodes and lead wires 91. As illustrated in FIG. 9, intentionally damaged surrounding TMD region 98, such as $MoS_2$ or $WS_2$, may be processed by doping with ion implantation or by bombardment with electrons or other radiation, to be converted to an insulator or very high resistivity region so as to serve as an effective mask. Circular or rectangular or other shaped regions 96 of undamaged $MoS_2$ (preferably defective or porous) having the exposed island region 92 surrounded by damaged $MoS_2$ having insulative properties or very high resistivity. Optional addition of dielectric mask material, (e.g. PMMA, PDMS, other adhesion-impeding polymer layer, or $SiO_2$ and other oxide or nitride dielectric layer) is not excluded from the scope of the embodiments disclosed herein. A multiple array of conducting electrode and lead wires 91 (e.g. Au, Pt, Ag, Pd, Rh, or their allows, etc.) may be used for signal detection. Massively parallel electronic sequencing analysis can be performed with many devices organized into a system, having as many as 10,000 or even at least 1 million devices. Intentionally damaged surrounding TMD region 98 (such as constructed with $MoS_2$ or $WS_2$) can be utilized, e.g., with a processing such as by doping with ion implantation or by bombardment with electrons, ion beams or other optical or particle radiations), to be converted to an insulator or very high resistivity region so as to serve as an effective mask. The high resistivity region is made to have a resistivity value of at least 100 ohm-cm resistivity, preferably at least 0.1 mega ohm-cm resistivity for the regions outside a specific region intended for attaching only a single molecule. Circular or rectangular geometry central region of undamaged $MoS_2$ (preferably defective or porous), with the exposed island region surrounded by damaged $MoS_2$ having insulator or very high resistivity characteristics can be constructed. While dielectric polymer or insulating silica masking may not be needed in such an intentionally severely damaged TMD mask surrounding the core undamaged or less-damaged TMD region, thus providing a reduced probability of electrical signal interference and reduced chance of biomolecule attachment, an optional addition of dielectric mask material, e.g., PMMA, PDMS, other adhesion-impeding polymer layer, or $SiO_2$ and other oxide or nitride dielectric layer) is not excluded as these additional dielectric mask will help to prevent biomolecule attachment.

Hydrophilic-Hydrophobic Composite Structured Bridge Surface

Surface wettability is an important aspect for handling of biomolecules and related components including DNAs, RNAs, nucleotides, enzymes, polymerase and so forth in aqueous environment such as in microfluidic devices for label-free genome sequencing systems. High-quality and clean TMD layers are in general hydrophobic. In some embodiments, the surface of the TMD layer is at least partially converted to a hydrophilic or super-hydrophilic surface. The hydrophilic surface is arbitrarily defined here as a surface with a water droplet contact angle of at most 50 degrees, preferably at most 30 degrees, even more preferably at most 15 degrees.

Figure 10A:
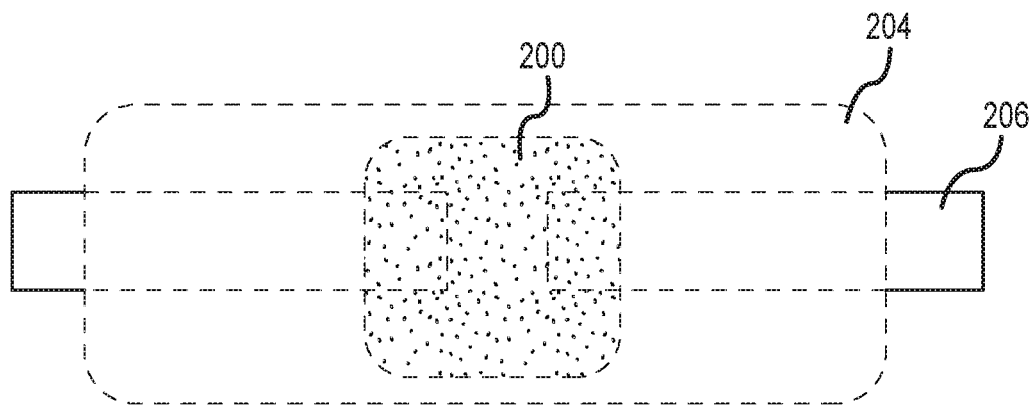
FIGS. 10A-10B illustrate exemplary embodiments of two configurations of hydrophilic-enabled TMS bridge surface structures. The embodiment detailed in FIG. 10A comprises a hydrophilic TMS surface, either all of the TMD surface or preferably the exposed part of the TMD layer, is provided by (i) plasma treatment (e.g., with oxygen-containing plasma) to convert the hydrophobic surface of the TMD layer to a hydrophilic surface by imperfect crystallization (by at least 10%, preferably at least 30% area fraction of TMD surface material) of $MoS_2$ type structure, e.g., by sulfurization/annealing at lower temp. The embodiment detailed in FIG. 10B comprises composite hydrophilic-hydrophobic configuration so as to enable easier biomolecule attachment and also allow other local covalent or hydrophobic-hydrophobic bonding. The size of either hydrophilic islands or hydrophobic islands is desirably 1-30 nm, preferably 1-10 nm, more preferably 1-5 nm, with the area fraction in the 85-15 ratio (or 15-85 ratio), preferably 70-30 ratio (or 30-70 ratio). The hydrophilic portion can be made by using masked plasma treatment or defective TMD layer (e.g., incomplete crystallization)
Figure 10B:
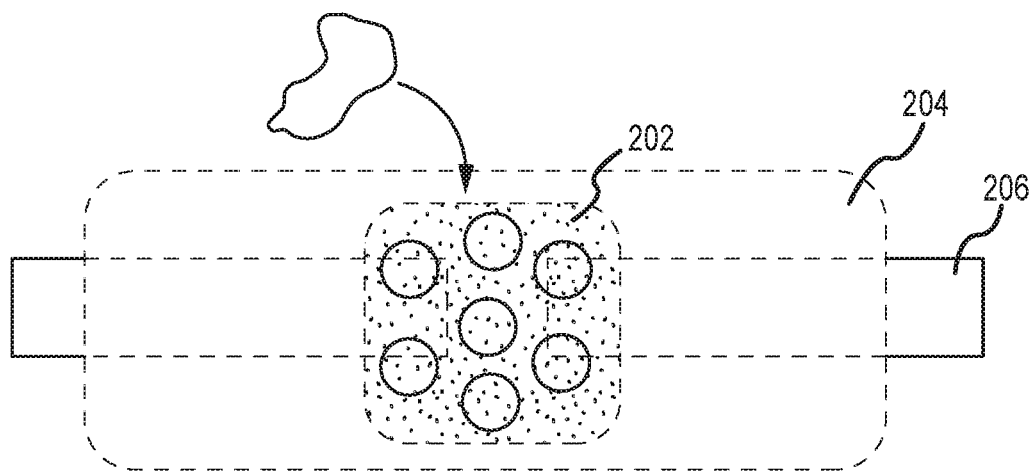

As illustrated in FIGS. 10A-10B, the TMD molecular bridge structure comprising electrode pairs 206, can be made to have a wholly hydrophilic surface 200 (FIG. 10A) or partly hydrophilic surface 202 (FIG. 10B) to enhance biomolecule attachment, e.g., by using plasma treatment using oxygen-containing plasma (or other types of plasma containing nitrogen, chlorine, fluorine or mixed elements), or using imperfect crystallization (by at least 10%, preferably at least 30% area fraction of TMD surface material having an imperfect crystal lattice configuration, with defects such as vacancies, interstitials, dislocations or aggregated defects) of $MoS_2$ type structure, e.g., by sulfurization/annealing at low temperature (or TMD structure in general). The TMD sheet 204 (e.g., preferably defective or porous like MoS2 or WS2) sheet, masked by dielectric (e.g., PMMA or adhesion-impeding polymer layer) to prevent biomolecule attachment.

An example of imperfect crystallization is to intentionally perform a less complete sulfurization annealing (or selenium or tellurium diffusion anneal process) at lower temperatures and shorter times. The annealing temperature after diffusional alloying of sulfur, selenium or tellurium into a deposited metal layer of transition metals (such as Mo, W, Zr, Hf, Co, Ni) is selected to be at least 50° C., preferably at least 200° C. lower than the temperature so that less completely crystallized structure with defects can be obtained as compared with the case of higher temperature anneal for obtaining a high-quality crystallization with more than 90% of the material having well crystallized TMD layer material.

Alternatively, a non-completed crystallization process can be applied with at least 10%, preferably at least 30% area fraction of TMD surface material having an imperfect crystal lattice configuration, with defects such as vacancies, interstitials, dislocations nanopores or aggregated defects) in the $MoS_2$ structure (or TMD structure in general), e.g., by sulfurization anneal (or selenium or tellurium diffusion anneal process) for shorter time periods during sulfurization synthesis of TMD layer from the pre-deposited metal layer, with the process time selected to be shorter by a factor of at least 3, preferably by a factor of 10 than the annealing time needed for obtaining high-quality crystallization with more than 90% of the material having well crystallized TMD layer material.

Exemplary embodiments illustrating two configurations of hydrophilic-enabled TMS bridge surface structures are presented in FIG. 10A and FIG. 10B. The structure in FIG. 10A represents wholly hydrophilic bridge surface 200. The hydrophilic region is patterned or synthesized as a less perfect crystals (e.g., ~3-20 um width). Another embodiment, is to introduce a composite (i.e. hydrophilic and hydrophobic) mixed surface configuration as described in FIG. 10B, which illustrates a composite configuration mix of hydrophilic islands and hydrophobic regions matrix regions 202. Such a composite hydrophilic-hydrophobic configuration enables easier biomolecule attachment and also allows other local covalent or hydrophobic-hydrophobic bonding to be utilized. The size of either hydrophilic islands or hydrophobic islands is desirably 1-30 nm, preferably 1-10 nm, more preferably 1-5 nm, with the area fraction in the 85-15 ratio (or 15-85 ratio), preferably 70-30 ratio (or 30-70 ratio), even more preferably 50-50 ratio. The hydrophilic portion can be made by using masked plasma treatment (e.g., exposure to oxygen plasma), or by employing defective TMD layer (e.g., incomplete crystallization), or a partial deposition of hydrophilic islands such as metallic nanoislands of transition metals like Ti, Zr, Hf, V, Nb, Ta, Cr, Mo, W, Mn, Fe, Co, Ni, Cu, Zn, or ceramic nanoislands of these elements such as $TiO_2$, NiO, $Fe_2O_3$., with an a real fraction of 5-50%, preferably at least 10%, more preferably at least 30%, using physical deposition, chemical deposition, electrochemical deposition, or ion implantation, with an a real fraction of 5-100%, preferably 10-50%.

Such a composite hydrophilic-hydrophobic configuration, enables improved biomolecule attachment frequency with the adhesion improvement by at least 30%, preferably by at least 50%, even more preferably by at least 100% increased adhesion event as compared to the all hydrophobic TMD surface during microfluidic chamber processing of fluid supplying to provide biomolecules, nucleotides, and related biological or chemical components, as well as washing or fluid replacement operations. The size of either hydrophilic islands or hydrophobic islands is desirably 1-30 nm, preferably 1-10 nm, and more preferably 1-5 nm. In either embodiment of FIGS. 10A and 10B, the TMD (e.g., preferably defective or porous like $MoS_2$ or $WS_2$) sheet, is masked by a dielectric 204 (e.g., PMMA or adhesion-impeding polymer layer) to prevent biomolecule attachment. Conducting electrodes and lead wires 206 (Au, Pt, Ag, Pd, Rh, or their alloys, etc.) are used for signal detection.

Size-limited, locally exposed TMD region (circular, square, or other shape) allows for single molecule attachment (e.g., 2-20 nm).

Figure 11:
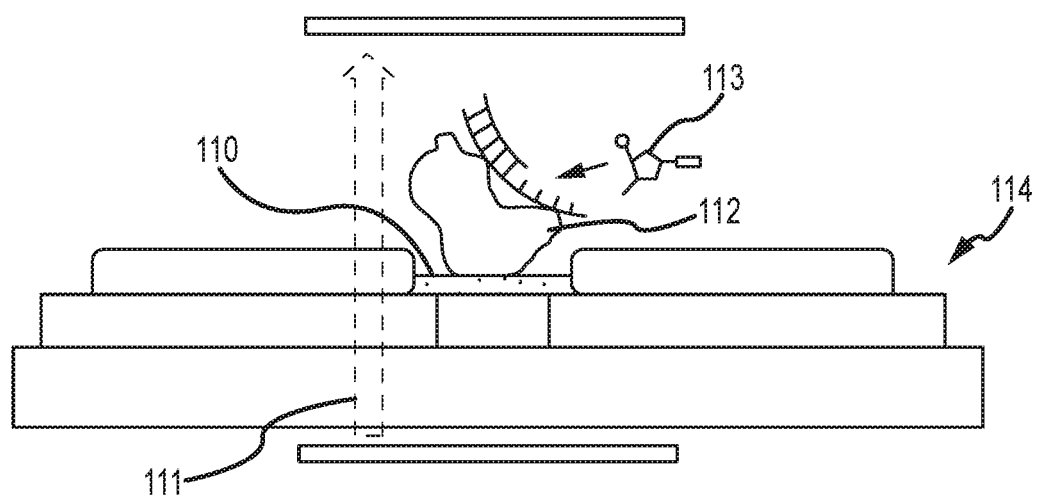
FIG. 11 illustrates a cross-sectional view of hydrophilicity-controllable TMD bridge molecular sensors like $MoS_2$ or $WS_2$ with the TMD positioned as a suspended layer (or, alternatively as substrate-adhered layer) and vertical electrodes to apply electric field to alter the semiconducting properties (to widen the bandgap) and make the TMD more hydrophilic for easier accommodation of fluidic chamber environment and improved adhesion of single enzyme molecule such as DNA or RNA polymerase. An array of these DNA or genome sequencing sensor can be made as a massively parallel sequencer system.

Use of Tunable Electric Field to Alter Hydrophilicity/Hydrophobicity and Bandgap Property Shown in FIG. 11 is a cross-sectional view of hydrophilicity-controllable TMD bridge molecular sensors based on TMD layers like $MoS_2$ or $WS_2$ with the TMD positioned as a suspended layer (or substrate-adhered layer). The suspended TMD bridge is attached and fixed onto the substrate by van der Waals force and a size-limited bridge using dielectric mask coating. The molecular bridge solid state sensor performs genome or DNA sequencing detection via change of current or other signal specifics upon attaching or detaching of a series of nucleotides or other biomolecules to the enzyme polymerase.

In some embodiments, vertical electrodes are positioned below and above the sensor bridge structure as in FIG. 11 to apply an electric field to alter the semiconducting properties (to widen the bandgap) and make the TMD more hydrophilic for easier accommodation of fluidic chamber environment and improved adhesion of single enzyme molecule such as DNA or RNA polymerase. The desired intensity of the vertical electric field to be applied is at least 10 V/nm, preferably at least 30 V/nm, in order to convert the TMD layer from hydrophobic to hydrophilic for enhanced biomolecule attachment, then the field is removed to return to a hydrophobic surface to avoid unnecessary attachment of biomolecules.

FIG. 11 illustrates an additional embodiment of a molecular bridge solid state sensor 114 that can be used genome or DNA sequencing detection via a change or current or other signals upon attaching or detaching of nucleotides or other biomolecules to polymerase. As illustrated in FIG. 11, a suspended TMD bridged 110 that is attached/affixed by van der Waals forces and dielectric mask coating. A single enzyme biomolecule 112 is attached onto the size limited TMD bridge 110. A vertical electrical field 111 (>10 V/nm, preferably >30 V/nm) is applied to convert the TMD layer from hydrophobic to hydrophilic for biomolecule 112 attachment. The electric field is then removed so that the surface is converted back to a hydrophobic surface to avoid unnecessary attachment of biomolecules, or to more easily remove the previously attached biomolecules as needed. After biomolecule e.g., DNA or RNA polymerase) attachment, the addition of a nucleotide monomer 113 (A, T, C, G, U, etc.) is be detected upon a change in the electrical signal after attachment of the monomer to the DNA strand.

Such a tunable electric field also serves another important function, i.e., to more easily remove the previously attached biomolecules via hydrophilicity/hydrophobicity alterations as needed, so that a new fresh biomolecule such as a single enzyme polymerase molecule like DNA or RNA polymerase can now be attached onto the size-limited TMD bridge location in order to continue genome sequencing indefinitely without having to replace the bridge or the sensor assembly. An application of DC electric field or AC electric field can be utilized for enhanced attachment or detachment of the biomolecule.

An array of these DNA or genome sequencing sensors can be made as a massively parallel sequencer system, having as many as 10,000 or even at least 1 million devices.

Figure 12:
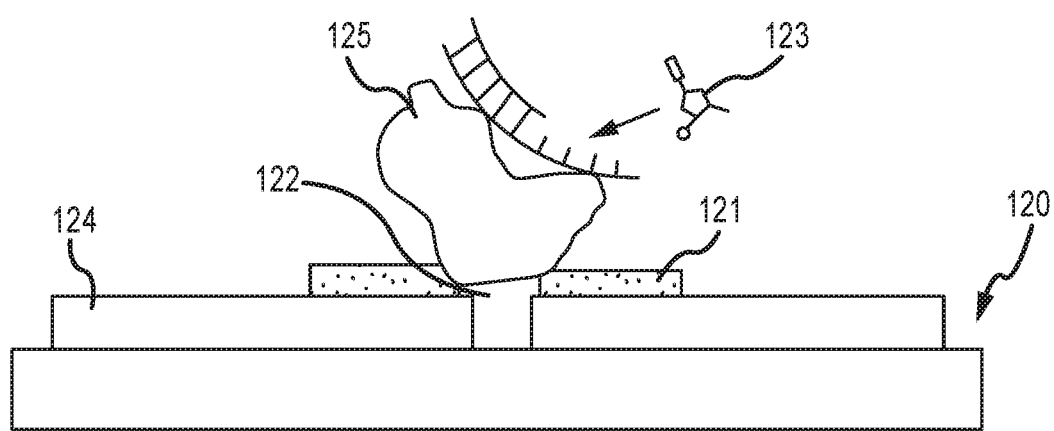
FIG. 12 illustrates an embodiment of a molecular bridge solid state sensor using nanogapped TMD layers for genome or DNA sequencing detection. Changes of current pulse shape and intensity or other signal aspects are measured upon attaching or detaching of a nucleotide or other biomolecules at the split-TMD tunnel junction configuration.

Split, Nanogapped TMD as a Well-Adherable Substrate for Tunnel Junction Construction Shown in FIG. 12 is a molecular bridge solid state sensor 120 using nanogapped TMD for genome or DNA sequencing detection. As shown in FIG. 12 a split, nanogapped TMD island regions like MoS2 or WS2 121 and a well-adhereable substrate for tunnel junction is used. The TMD island is split into two regions with a nanogap 122 of 2-20 nm between the two TMD regions. When a nucleotide 123 or other biomolecule is attached to the enzyme biomolecule 125 (e.g., DNA or RNA polymerase) in the $MoS_2$ type TMD nanogap 122 in a tunnel junction configuration, a unique pulse current signal is generated at the split-TMD tunnel junction, which provides information on what type of nucleotide is being attached. Conducting electrode pairs and lead wires 124 (Au, Pt, Ag, Pd, Rh, or their alloys, etc.) are used for signal detection. The drawing of FIG. 12 shows a side view of the molecular bridge solid state sensor using nanogapped TMD for genome or DNA sequencing detection. Changes of current pulse shape and intensity, or other signal aspects, are measured upon the attaching or detaching of a nucleotide or other biomolecule at the split-TMD tunnel junction configuration.

Block Copolymer Membrane Based Alteration of TMD Structure for Intentional Defects The TMD layer can be processed using nanotemplating to induce a very high density of nanopore type defects, which can increase bandgap as well as enhance the adhesion of the biomolecule (e.g., enzyme molecule of DNA or RNA polymerase) onto the TMD surface for robust and reliable sequencing. Shown in FIGS. 13A-13F is an exemplary fabrication procedure using diblock copolymer mask to produce a nanopatterned TMD bridge. A TMD layer 130 can be grown by various known methods such as CVD synthesis, exfoliation or sulfurization activation of thin deposited metal layer surface. The drawing of FIG. 13A shows the resulting TMD layer like $MoS_2$ or $WS_2$ on a metal foil, forming the starting material. Synthesis of the TMD like $MoS_2$ or $WS_2$ layers can occur through exfoliation, CVD, or sulfurization of metal film. After the metal is etched away (FIG. 13B), the floating TMD layer 131 in water or solvent 132 is transferred by lifting up onto the device surface, e.g., nano-gapped, Au, Pd or Pt electrode pair on $SiO_2$ (or $SiO_2$-coated Si substrate) 133, to position the TMD layer as a suspended bridge.

The TMD surface on top of the device above the $MoS_2$ layer 131 and substrate layer 133 is then covered by a thin layer of evaporated $SiO_2$ 134 and a lift-up-deposited or transfer-deposited thin film of spin-coated block-copolymer, e.g., PS-b-P4VP copolymer 135, as shown in FIG. 13C. The PS-b-P4VP type block-copolymer film is annealed and RIE is used to remove one of the phases. This results in a nanoscale two-phase structure, leaving the porous PS matrix 136 as the template for subsequent patterning (as shown in FIG. 13D) on which a fluoride-based reactive ion etching (RIE) is performed to remove the $MoS_2$ layer. The SiO2 oxide layer is penetrated and patterned, partially degrading the PS film, and forming the hard mask hole pattern out of the thin $SiO_2$ 137, as shown in FIG. 13E. The TMD layer in the exposed hole area is etched away by $O_2$ plasma that penetrates through the hole array in the silica mask layer, after which the $SiO_2$ mask is removed by etching. Finally, nanoporous TMD on $SiO_2$ substrate is obtained 138, as shown in FIG. 13F which is then patterned into a size-limited island TMD by dielectric masking to allow only a single molecule attachment (e.g., an enzyme polymerase biomolecule) for nucleotide attachment analysis.

An alternative method of placing the TMD layer on the substrate is to utilize a transfer method (instead of lift-up method using a floating TMD membrane from a solution), e.g., using a gentle vacuum device or a stamp to pick up the TMD sheet and release it on the desired location on the substrate surface, optionally using a releasing agent material at the interface between the pick-up device and the TMD layer.

Various types of diblock copolymers or triblock copolymers can decompose into different types and sizes of two phase structures, and the block copolymer masked patterning approach can produce desirably ~2-50 nm size defects, preferably 2-10 nm size defects on TMD for bandgap opening and enhanced biomolecule adhesion. The desired density of artificially introduced nanopores on TMD by block copolymer template approach is at least $10^5/cm^2$ preferably at least $10^7/cm^2$, even more preferably at least $10^{10}/cm^2$.

AAO Membrane Based Alteration of TMD Structure for Intentional Defects

Other templates other than diblock copolymers can also be utilized for nanoporous TMD synthesis, e.g., AAO (anodized aluminum oxide) membrane. Shown in FIGS. 13G-13L is an AAO membrane based nanopatterning of TMD for molecular bridge sensors useful DNA sequencing. The TMD layer 140 synthesized by CVD, exfoliated, or made by diffusional synthesis of S, Se, Te onto thin metal surface, FIG. 13G, is placed on a substrate 141 by list-up process, shown in FIG. 13H. An alternative method of placing the TMD layer on the substrate, prior to placement of AAO membrane is to utilize a transfer method (instead of lift-up method using a floating TMD membrane from a solution), e.g., using a gentle vacuum device or a stamp to pick up the TMD sheet and release on the desired location on the substrate surface, optionally using a releasing agent material at the interface between the pick-up device and the TMD layer.

Figure 13M:
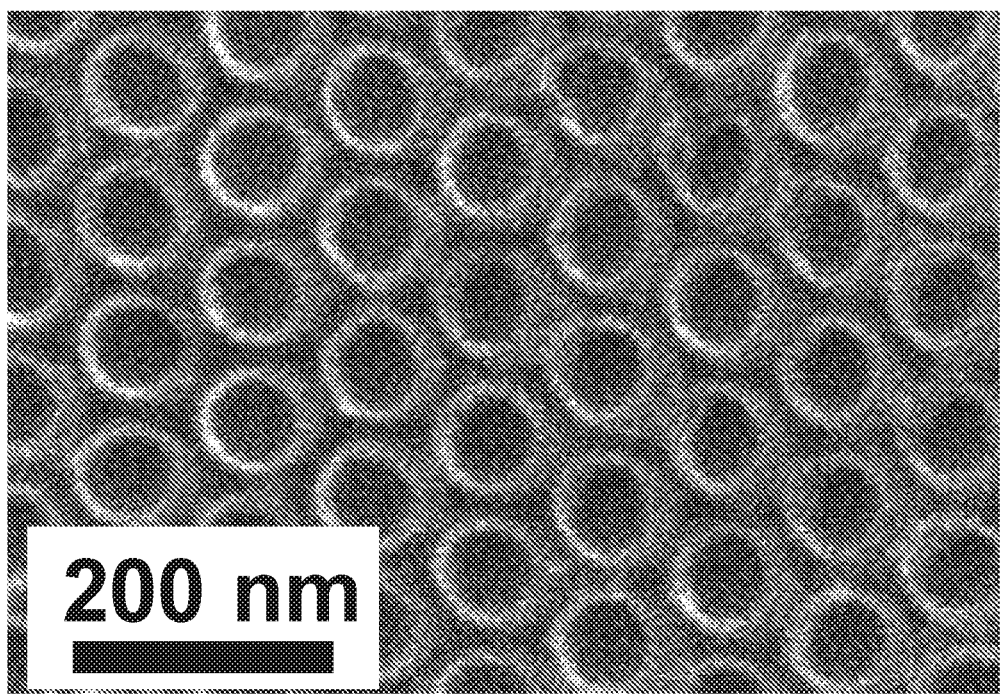
FIG. 13M is an image of exemplary patterning of $MoS_2$ layer using AAO membrane to produce an 80 nm diameter hole array. The floating AAO membrane of FIG. 13G was collected onto the top surface of $MoS_2$ layer coated $SiO_2$ substrate, and the nanopatterning was conducted using $BCl_3$/Ar plasma etching at 100 W under 4.5 mTorr for 4 min, with the AAO as the mask.

The AAO nanohole membrane 142 fabricated (FIG. 13I) is placed on TMD ($M_oS^2$) e-coated substrate surface 143 (FIG. 13J) followed by RIE etching of TMD through the AAO array holes 144 (FIG. 13K) and removal of AAO template to obtain nanoporous TMD layer to reveal the nanopatterned $MoS_2$ layer 145 (FIG. 13L). The desired density of artificially introduced nanopores on TMD by AAO template approach is at least $10^5/cm^2$ preferably at least $10^7/cm^2$, even more preferably at least $10^{10}/cm^2$. FIG. 13M is an image of exemplary patterning of $MoS_2$ layer using AAO membrane to produce an 80 nm diameter hole array. The floating AAO membrane of FIG. 13G was collected onto the top surface of $MoS_2$ layer coated $SiO_2$ substrate, and the nanopatterning was conducted using $BCl_3$/Ar plasma etching at 100 W under 4.5 mTorr for 4 min, with the AAO as the mask.

FIG. 13G shows TMD synthesis like $MoS_2$ or $WS_2$ through exfoliation, CVD or sulfurization on metal foil. After the metal is etched away, the $MoS_2$ layer is floating in water or solvent 146 (FIG. 13H). The floating $MoS_2$ 147 layer is transferred by lifting it up into the device surface on $SiO_2$ (or $SiO_2$-coated Si substrate), to position the TMD layer as a suspended bridge (FIG. 13H). An AAO nanohole membrane 142 is synthesized (e.g., by anodization of Al foil) and the Al matrix is dissolved away (FIG. 13I). The AAO membrane is floated in solvent or water 148 and the $MoS_2$ coated substrate 143 is lifted up to pick up the AAO membrane 149 (FIG. 13J). A layer of dry AAO coating is added and RIE is performed to penetrate the AAO masked holes 144 (FIG. 13K). The AAO is removed to produce nanopatterned TMD like $MoS_2$ or $WS_2$, 145 (FIG. 13L). The nanopatterning was conducted using $BCl_3$/Ar plasma etching at 100 W under 4.5 mTorr for 4 min, with the AAO used as the mask.

Defective TMD layers obtained by nanopore generation, such as via the processes described, for example, in FIGS. 13A-13M, may be additionally and optionally post-etch annealed (e.g., at 100°-600° C. for 10 minutes to 24 hrs.) for bandgap change and easier biomolecule attach.

Yet another embodiment to generate nanoporous TMD is to utilize nanoimprinting patterning (see, for example: FIGS. 2A-2B) so as to introduce a defect density of at least $10^5/cm^2$. A master nanoimprinting mold (e.g. stamps), such as, with 10 nm regime nanoislands, nanoholes or nanolines, can be generated by e-beam lithography. Many daughter stamps can then be generated using the known pattern transfer techniques to allow nanopatterning of many devices.

Evolution or Mask Layer Being Deposited on Graphene

At the early stage of deposition, the mask material can have more defective structure like FIG. 14A or B. As the film gets thicker for longer period deposition (e.g., by sputtering or evaporation), the pinholes or defects gradually become less frequent as shown in FIGS. 14C and D. FIG. 14A shows graphene 162 on a support 164 (sequencing structure base or split substrates for graphene suspension). Atoms 160 are being sputtered on the surface of graphene 162. Plasma etch 166 is carried out to create graphene with nanodefects 168 (FIG. 14E).

Figure 15A:
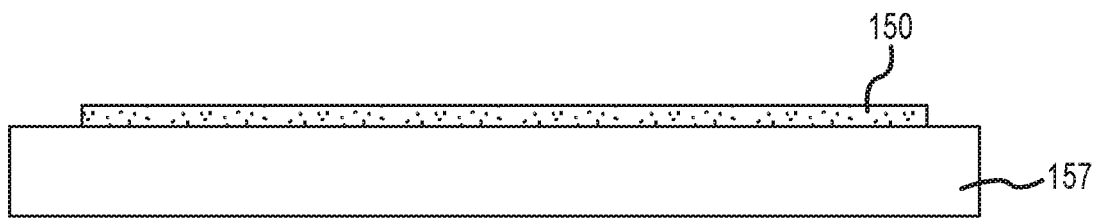
FIGS. 15A-15D illustrate exemplary perforated and defective TMD like $MoS_2$ or $WS_2$ for molecular bridge DNA or RNA sensors and method for making sensors.
Figure 15B:
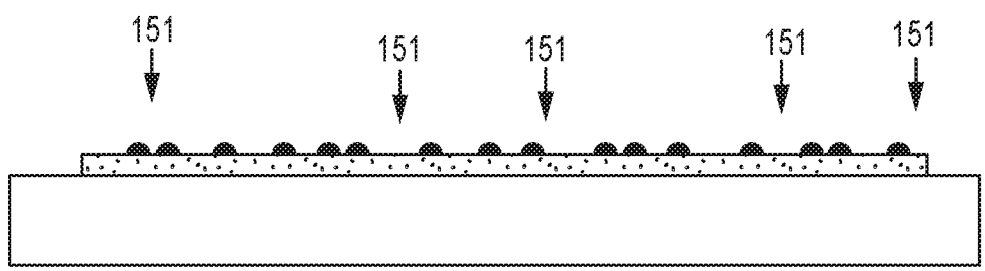
Figure 15C:
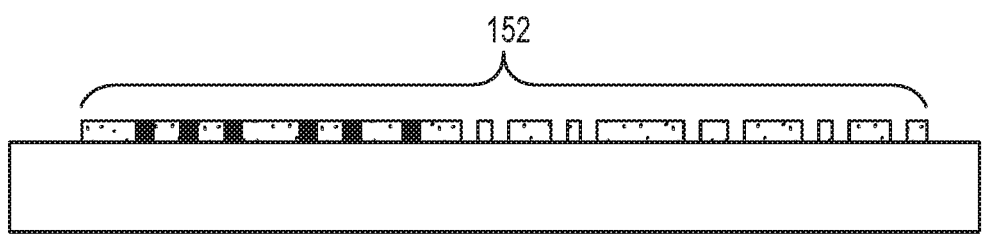
Figure 15D:
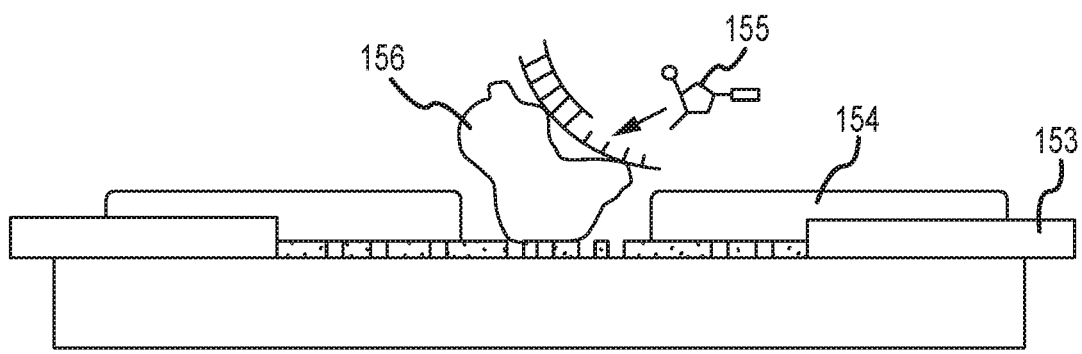

Defective or Nanoporous TMD Layer by Diffusional Reaction with Metallic Nanoparticles Desirably defective TMD or nanoporous TMD can also be prepared by thermally induced reaction of TMD material with metallic nanoparticles. Shown in FIGS. 15A-15D is an exemplary defective or perforated TMD like $MoS_2$ or $WS_2$ for molecular bridge sensors for DNA, RNA or genome sequencing. As shown in FIG. 15A, the surface of the TMD layer 150 is coated with metallic nanoparticles (NPs with 1-20 nm dimension), e.g., by early stage of island type thin film deposition of e.g., Cu, Zn, In, Sn, Al, by sputtering or evaporation, which is optionally followed by annealing to ball up the metal into nanoparticles 151 (nanoislands) (as shown in FIG. 15B), which upon further annealing will form compositionally altered island array 152 through diffusional reactions to form altered composition defects, or nanopores in the TMD layer by differential chemical etching or RIE etching (as shown in FIG. 15C). The altered TMD nanoregions become defective by reaction with 1-20 nm size nanoparticles (e.g., local TMD diffusional composition change with metallic nanoislands). These nanoislands can also be differentially chemical or RIE etched way for creation of nanopores in the TMD layer, which could allow for easier biomolecule attachment and for additional bandgap opening, if desired. Electrical lead wires 153 and size-limiting dielectric layer 154 (polymer or ceramic) is then added (as shown in FIG. 15D) to make the solid state electronic sensor for single enzyme molecule attachment and associated analytes attachment and sequencing analysis. The electrical lead wires 153 (Au, Pt, Pd, alloys) detect a nucleotide monomer 155 (A, T, C, G, U, etc.) upon attachment of the monomer to a strand of DNA (as shown in FIG. 15D). A single enzyme molecule 156 (e.g., DNA or RNA polymerase) is attached onto a size-limited TMD bridge (as shown in FIG. 15D).

FIGS. 15A-15D also illustrate a method of manufacturing molecular bridge DNA or RNA sensors comprising perforated and/or defective TMD such as $MoS_2$ or $WS_2$. FIG. 15A shows a TMD layer 150 deposited on a dielectric substrates 157, as obtainable by any of the methods described above. FIG. 15B shows coating the TMD surface with 1-20 nm sized metallic nanoislands 151. As mentioned, this step may comprise early stage island-like thin film deposition, optionally followed by annealing to ball up the metal into nanoislands. FIG. 15C demonstrates inducing diffusional reactions by heating to form altered composition defects or nanopores in the TMD layer, such as by differential chemical etching or RIE etching. FIG. 15D shows adding electrical lead wires 153 and a size-limiting dielectric layer 154 (e.g. polymer or ceramic). Each size-limited region is then disposed to accept a single enzyme molecule for attachment to the exposed TMD. The final sensor resulting thereby is a solid state electronic sensor for analyte attachment and sequencing analysis.

The desired density of artificially introduced nanopores on TMD is at least $10^5/cm^2$ preferably at least $10^7/cm^2$, even more preferably at least $10^{10}/cm^2$. On such nanoporous TMD, electrical lead wires and size-limiting dielectric layer (polymer or ceramic) can be added to make the solid state electronic sensor for single enzyme molecule and associated analytes attachment and sequencing analysis. The single molecule enzyme (polymerase) on TMD enables each of the polymerase reaction of nucleotide attachment (nucleotide monomers like A, T, C, G, U or modified nucleotides) to uniquely change electrical properties of the molecular bridge for DNA, RNA or genome sequencing analysis.

Instead of using a phase decomposition, a porous mask, nanoparticles and other approaches, a defective TMD can also be obtained by a beam irradiation for enhanced molecular bridge DNA or RNA sensors. As shown in FIGS. 16A-16D, a TMD layer disposed on the electrode system can be irradiated by ion implantation beam, plasma reactive ion etch (RIE) atmosphere, broadened optical, electron, particular or neutron beam. The defective TMD layer so obtained by irradiation (with an optional addition of post-irradiation annealing), can be combined with electrical lead wires and size-limiting dielectric mask layer (polymer or ceramic) to make the solid state electronic sensor for single enzyme molecule and associated analytes attachment and sequencing analysis. The desired density of defects in TMD produced by irradiation is at least $10^5/cm^2$, preferably at least $10^7/cm^2$ even more preferably at least $10^{10}/cm^2$. DNA, RNA or genome sequencing analysis is enabled when the single molecule enzyme (polymerase) on TMD causes each of the polymerase reactions of nucleotide attachment (nucleotide monomers like A, T, C, G, U or modified nucleotides) to uniquely change electrical properties of the molecular bridge sensor.

Such defective TMD layers obtained by beam irradiation may be additionally post-etch annealed (e.g., at 100-600° C. for 10 minutes to 24 hrs. for stress relief treatments or atomic rearrangements) for bandgap change and easier biomolecule attachment, as exemplified in FIGS. 16A-16D.

Figure 16A:
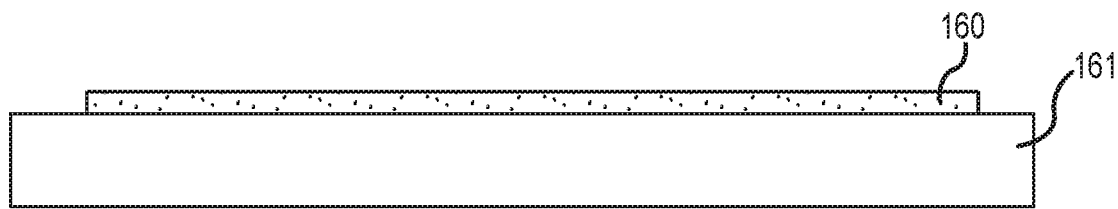
FIGS. 16A-16D illustrate defective TMD like $MoS_2$ or $WS_2$ by a beam irradiation for enhanced molecular bridge DNA or RNA sensors.
Figure 16B:
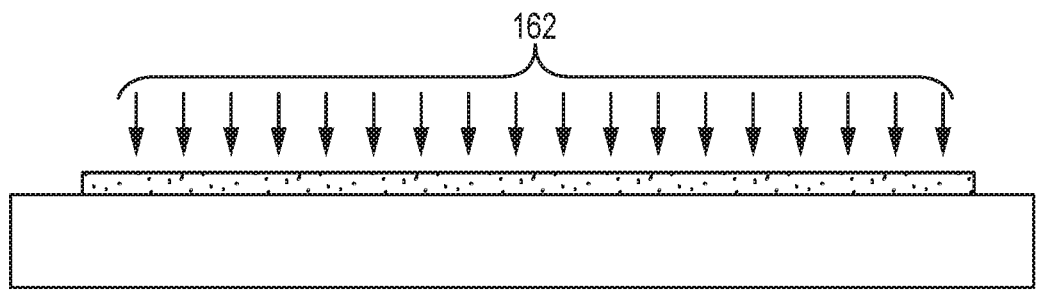
Figure 16C:
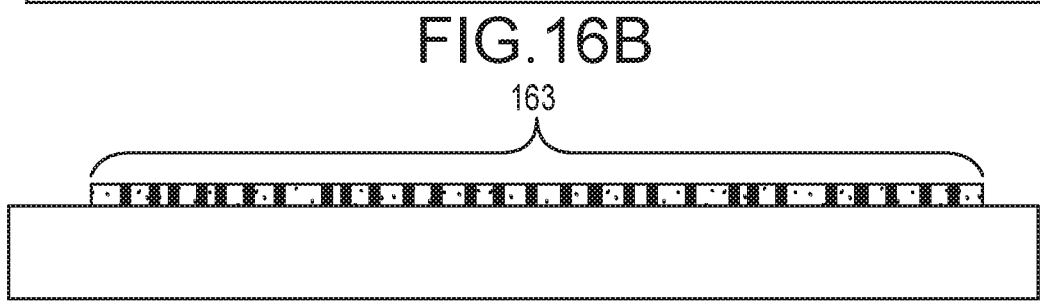
Figure 16D:
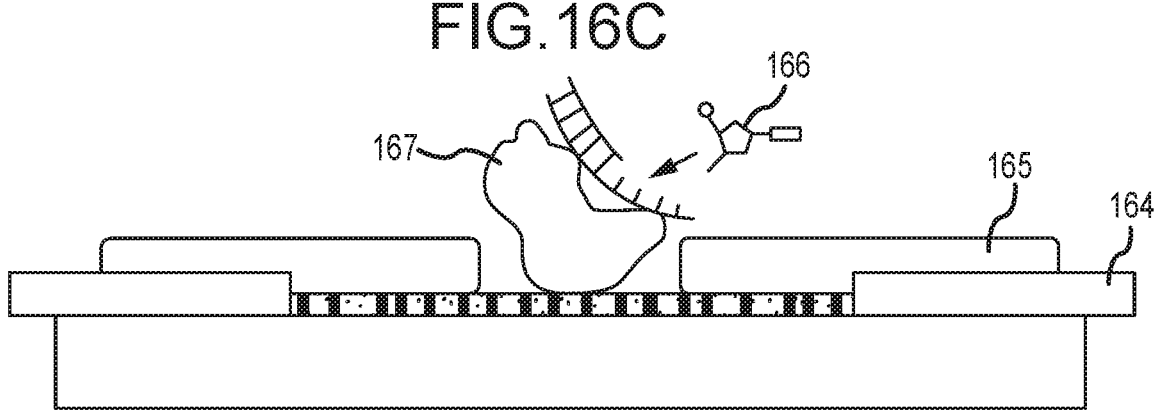

The method illustrated in FIGS. 16A-16D begins with placement of a TMD layer 160 on a dielectric substrate 161 ($SiO_2$, $Al_2O_3$, etc.) (as shown in FIG. 16A). FIG. 16B illustrates the TMD being broad-beam irradiated with ion implantation beam (e.g., with N, C, F, O, H, Ar, Ni, Ti, Mn, Fe, Cu, Al, and other species), plasma reactive ion etch (RIE) atmosphere, broadened optical, laser beam, electron, ion or defocused neutron beam 162. The broad beam irradiation with ion implantation may include any of N, C, F, O, H, Ar, Ni, Ti, Mn, Fe, Cu, or Al, or other species, and the broad beam may include plasma RIE defocused neutron beam, laser beam and/or electron beam. In FIG. 16C, defective TMD is produced by irradiation 163. Optional post-irradiation annealing may be used to induce point defects, interstitials or agglomerated nanoparticles or nanopore defects for bandgap change and for easier biomolecule attachment. In FIG. 16D, electrical leads 164 (Au, Pt, Pd, alloys) are added along with the size-limiting dielectric mask layer 165 (polymer or ceramic) for single molecule attachment, creating a solid state electronic sensor for detection and analysis of analyte attachment and sequencing. Nucleotide monomers 166 (A, T, C, G, U, etc.) are detected by the electrical lead wires upon attachment to the DNA strand. A single enzyme molecule 167 (e.g., DNA or RNA polymerase) is attached onto a size-limited $MoS_2$ bridge. The density of defects in the TMD layer like $MoS^2$ and $Ws^2$ is at least $10^5/cm^2$, preferably at least $10^7/cm^2$.

Figure 17A:
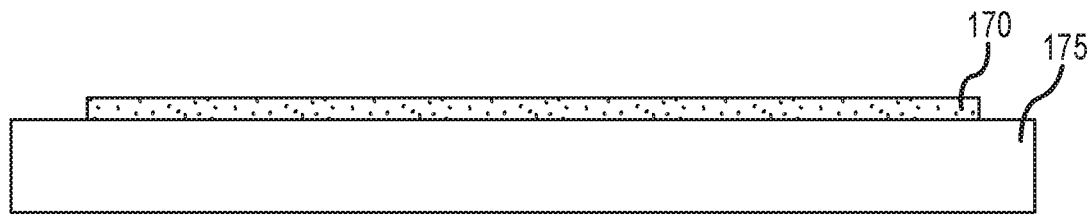
FIGS. 17A-17D illustrate chemically induced defective TMD like $MoS_2$ or $WS_2$ (disturbed lattice regions or nanopores).
Figure 17B:
Figure 17C:
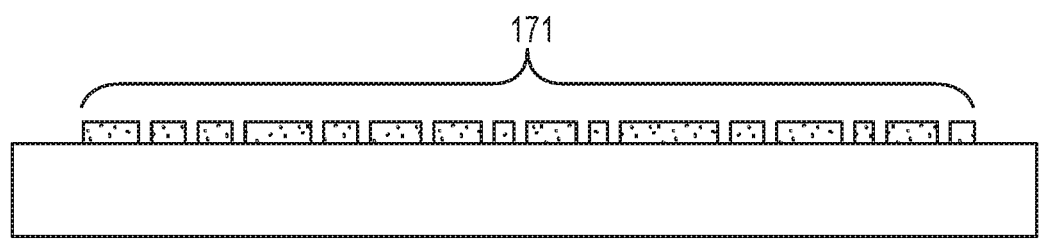
Figure 17D:
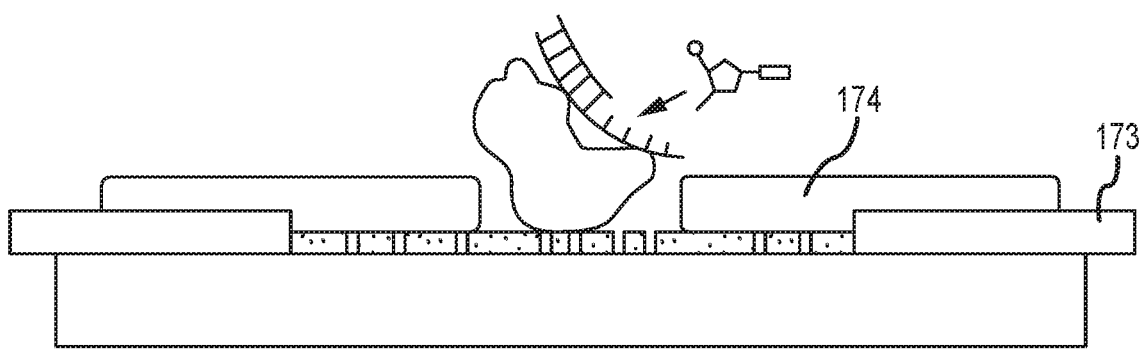

Nanoscale or lattice-scale defects can also be created, by using various chemical reactions. FIGS. 17A-17D illustrate an embodiment of a method for manufacturing a chemically induced defective TMD layer like $MoS_2$ or $WS_2$. (with disturbed lattice regions or nanopores). As shown in FIGS. 17A-17D, a TMD layer 170 (as shown in FIG. 17A) is chemically etched on the TMD surface in an electrochemical etching bath 172 (as shown in FIG. 17B), which creates defective TMD 171 (with the optional addition of post-etch annealing) (as shown in FIG. 17C). Electrical lead wires 173 and a size-limiting dielectric layer 174 (polymer or ceramic) are used to make the solid state molecular electronic sensor for single enzyme molecule and associated analytes attachment and sequencing analysis (FIG. 17D). The TMD layer 170 is on a sequencing solid state sensor substrate 175 (dielectric substrate ($SiO_2$, $Al_2O_3$, etc)) (FIG. 17A) and is immersed in a chemical etching or electrochemical etching bath 172 (FIG. 17B). The steps in chemical etching may comprise an oxidizing reaction etch, with (i) acidic solutions including concentrated $H_2SO_4$, $HNO_3$, $KClO_3$, or their mixtures, preferably hot, (ii) alkaline solutions like hot KOH or NaOH, or (iii) use of a de-alloyed and nanoporous layer of Au—Ag alloy as a mask to etch the TMD surface. Chemical etching creates a defective TMD layer 171 (FIG. 17C). The chemically modified TMD may optionally be given a post-irradiation annealing (e.g., 100-600° C. for 10 minute to 24 hrs.) to optimize the defective structure for enhanced bandgap change and easier biomolecule attach. Electrical lead wires 173 and a size-limiting dielectric layer 174 (polymer or ceramic) are then added (FIG. 17D) to make the solid state electronic sensor for single enzyme molecule and associated analytes attachment (e.g., nucleotide monomer (A, T, C, G, U, or modified nucleotides) and sequencing analysis.

Chemical etching can be performed, e.g., as an oxidizing reaction etch, with i) acidic solutions including concentrated $H_2SO_4$, $HNO_3$, $KClO_3$ or their mixtures, preferably using a hot solution, or ii) alkaline solutions like hot KOH or NaOH, or iii) by using a de-alloyed and nanoporous layer of e.g., Au—Ag alloy film (2-20 nm thickness, sputter or evaporation deposited) as a mask to etch the TMD.

Defective TMD obtained by chemical etching, such as for example by the method illustrated in FIGS. 17A-17D, may be optionally and additionally post-etch annealed (e.g., at 100-600° C. for 10 minutes to 24 hrs.) for stress relief annealing, bandgap change, and easier biomolecule attachment.

Figure 18A:
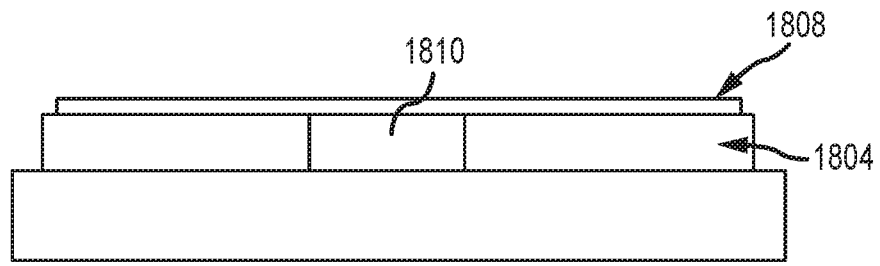
FIGS. 18A-18D illustrate a shape-altered TMD layer induced by a shape-altering dielectric insert within or near the nanogap. Such a shape-altering insert serves to provide additional defects for enhanced biomolecule adhesion, which can be left permanently underneath the TMD layer as a mechanical support, or dissolved away.

Three-Dimensionally Shaped TMD Layer for Sequencing by Shape-Altering of 2D Configured TMD While the TMD layers employed are typically have been described mostly as a flat layer above, embodiments herein also encompasses a non-flat, three-dimensional (3D) shaped TMD layers as another possible embodiment. Shown in FIGS. 18A-18D illustrate an example of altering a 2D layer to a 3D configuration so as to induce new modes of defects and shape discontinuity for higher-energy-state local regions. FIGS. 18A-18D illustrate a shape-altered TMD layer induced by a dielectric insert in or near the nanogap. Such an insert serves to provide additional defects for enhanced biomolecule adhesion. The insert can be left permanently underneath the TMD layer as a mechanical support, or can be dissolved away. In the FIG. 18A suspended $MoS_2$ or $WS_2$ layer 1808 (or TMD transition metal dichalcogenide layer in general), having a regular, or narrow-ribbon configuration (or a TMD layer intentionally made defective by processing) is nanopatterned by nanoimprinting (preferably) or e-beam lithography if needed. Conducting electrode pair 1804 is selected from a film of a patterned stable metal such as Au, Pt, Ag, Pd, Rh, or their alloys for signal detection) with a nanogap between each pair typically being in the range of e.g., 2-20 nm (FIG. 18A).

A shape-altered TMD layer 1806B is produced by inserting a shape-altering dielectric insert 1807 in the nanogap 1810, to provide additional defects for enhanced biomolecule adhesion. The shape-altering insert results in a shape-altered TMD layer as depicted in 1806B, 1086C, and 1086D. The shape-altering insert can be added by physical or chemical or solution deposition and back etch, deposition and patterning via lithography, or gap filling and solidification. Such a shape-altering insert may comprise a dielectric material selected from polymer materials such as PMMA ((poly)methylmethacrylate), HSQ (hydrogen silsesquioxine), or ceramic materials like $SiO_2$, $Al_2O_3$, MgO and other dielectric materials. The shaped inserts can be left under the TMD layer for mechanical reinforcement, such as in FIG. 18B, or optionally removed if desired as illustrated in FIG. 18C or FIG. 18D. The desired shape-altering insert structure can be made and deposited at the nanogap between the two electrodes, e.g., by physical or chemical or solution deposition and optional back etch, deposition and patterning via lithography, or gap filling and solidification. The shape-altering insert structure can also be deposited or placed, not just in the nanogap, but on the top surface of the electrode, if desired, For example, the TMD layer can be deposited on top of the size-limited 2-20 nm diameter metallic islands of Au, Pt, Ag, Pd, Rh, or their alloys, which are sometimes utilized to attach a single polymerase enzyme molecule onto the electrode pair.

Shape-altered TMD layer (such as $MoS_2$, $WS_2$) can optionally have a nanoporous structure, irradiated structure, lattice-defective structure with vacancies, aggregates of pores or interstitials, chemically etched defects, ion implanted defects, and so forth. The shape-altering inserts can be left as is or removed by solvent, acid or reactive ion etching (RIE). The altered shape can be hemispherical, rectangle, oval, wavy or other periodic or irregular geometry. The insert can also have some sharp or jagged tips so as to intentionally cause a local puncturing or tearing of TMD. These intentionally altered shapes provide additional defects at the curved or kinked position with displaced or strained lattice in TMD, which locally changes bandgap, and produces higher energy state positions for enhanced adhesion of enzyme biomolecules. The result of using a shape-altering insert structure 1807 is a shape-altered TMD layer, such as 1806b, 1806c, or 1806d, optionally having nanoporous structure, irradiated structure, defective structure with lattice vacancies, aggregates of pores or interstitials, chemically etched defects, ion implanted defects, or the like. The shape-altering inserts 1807 may be left in as mentioned, or removed by solvent, acid, or RIE. The altered shape may be hemispherical, rectangular, oval, wavy, or any other periodic or irregular geometry. Further, the altered shape may be any shape such that the TMD is punctured or torn. These altered shapes provide additional defects at the curved or kinked position comprising displaced or strained lattice in the TMD, which locally changes bandgap and produces higher energy state positions for enhanced adhesion or enzyme biomolecules. The desired shape-altering insert structure can be made and deposited at the nanogap between the two electrode, e.g., by physical or chemical or solution deposition and optional back etch, deposition and patterning via lithography, or gap filling and solidification. The shape-altering insert structure can also be deposited or placed, not just in the nanogap, but on the top surface of the electrode, if desired. For example, the TMD layer can be deposited on top of the size-limited, 2-20 nm diameter metallic islands of Au, Pt, Ag, Pd, Rh, or their alloys, which are sometimes utilized to attach a single polymerase enzyme molecule onto the electrode pair.

Shape-altered TMD layers (such as $MoS_2$, $WS_2$) can optionally have a nanoporous structure, irradiated structure, lattice-defective structure with vacancies, aggregates of pores or interstitials, chemically etched defects, ion implanted defects, and so forth. The shape-altering inserts can be left as is or removed by solvent, acid or reactive ion etching (RIE). The altered shape can be hemispherical, rectangle, oval, wavy, or other periodic or irregular geometry. The insert can also have some sharp or jagged tips so as to intentionally cause a local puncturing or tearing of TMD. These intentionally altered shapes provide additional defects at the curved or kinked position with displaced or strained lattice in TMD, which locally changes bandgap, and produces higher-energy-state positions for enhanced adhesion of enzyme biomolecules.

Figure 18B:
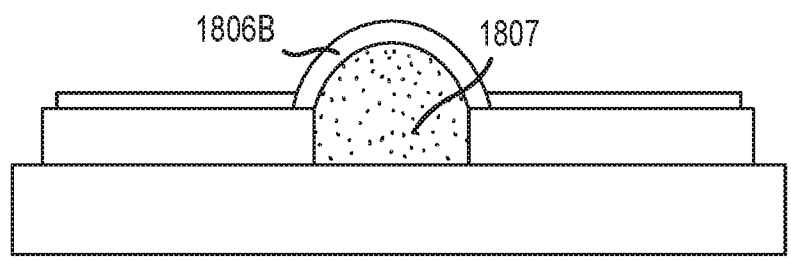
Figure 18C:
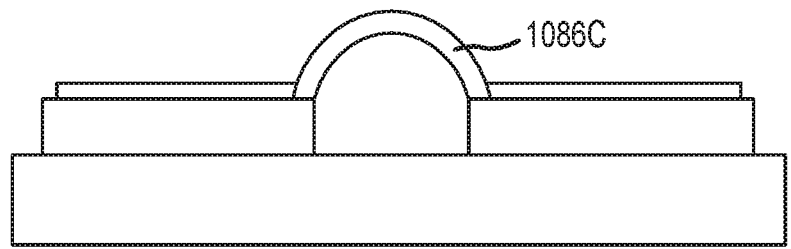
Figure 18D:
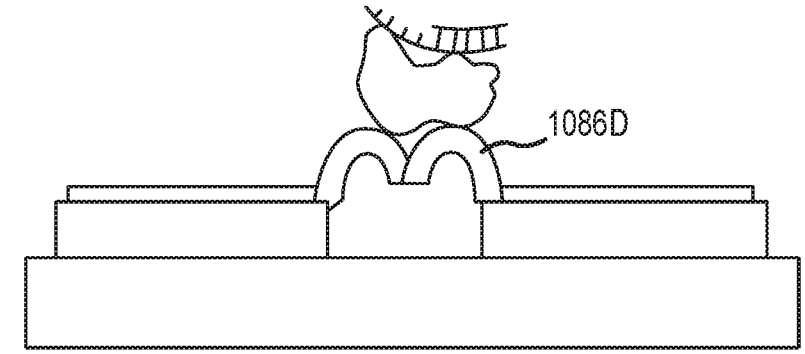

As illustrated in FIG. 18B, the insert can be left permanently underneath the TMD layer to serve as a beneficial mechanical support (e.g., to guard against mechanical detachment or damage of the TMD layer during microfluidic handling of the sequencing device systems and associated inadvertent force applied to the suspended or barely bonded TMD layer on the nanogap region). Thus such an intentionally added protruding insert structure in the nanogap serve a dual function of (i) mechanical reinforcement for enhanced durability/reliability of the attached TMD layer during a microfluidic operation or washing (and associated durability of the linked polymerase biomolecule and single/double strand DNAs on TMD near the nanogap), and (ii) enhancement of attachment of polymerase type enzyme biomolecule (or any desired biomolecule in general) onto the nanogap for sequencing operations.

Figure 19:
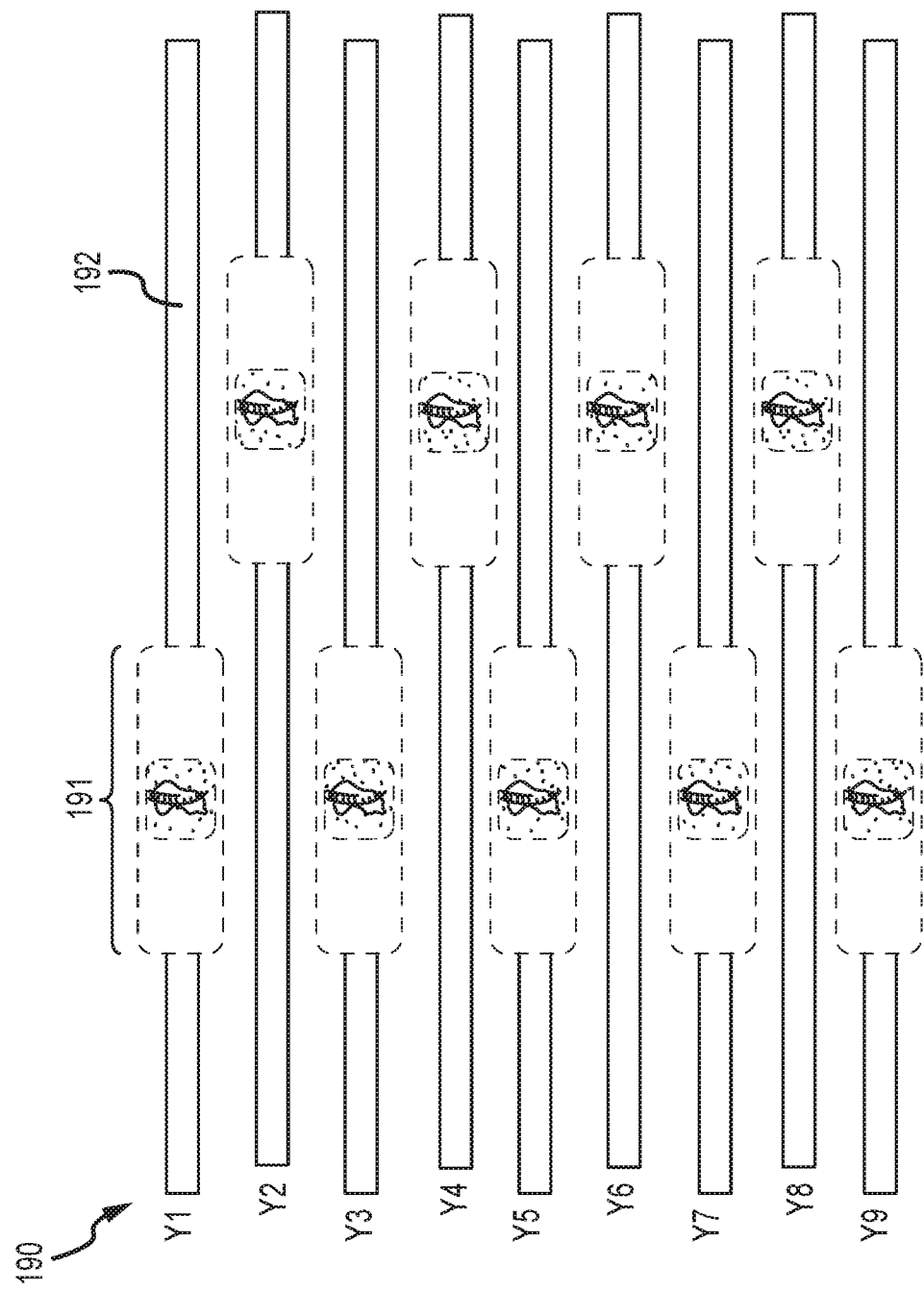
FIG. 19 illustrates an embodiment of a massively parallel array of solid state molecular sensor device comprising many TMD-containing enzyme polymerase structures (e.g., with $MoS_2$ or $WS_2$ layer) for DNA or genome sequencing. An areal distribution of the devices with associate routing of electrical wiring is provided.

Solid state molecular sensors for nucleic acid sequencing device comprising a combined structure of size-limited TMD and a single biomolecule enzyme polymerase, such as any of the embodiments illustrated in FIG. 1A-FIG. 18D can be made into an array of at least thousands of device assembly, as illustrated in FIG. 19. The availability of many parallel devices makes the sequencing analysis to be conducted faster, with more accuracy. Also, such a parallel processing scheme will make the overall system less costly. FIG. 19 illustrates an embodiment of a massively parallel array of a solid state molecular sensor device 190 comprising many TMD-containing enzyme polymerase structure (e.g. $MoS_2$ or $WS_2$ layer) for DNA or genome sequencing and label-free detection of nucleotide attachment. A TMD-containing enzyme polymerase molecular sensor 191 allows for label-free detection of nucleotide attachment. An areal distribution of the devices with associated routing of electrical wiring may be provided as illustrated. For example, Au lead wires 192 (surface insulated or coated to prevent protein adhesion) may be used. The availability of many parallel devices makes the sequencing analysis to be conducted faster, with more accuracy. Also, such a parallel processing scheme will make the overall system to be less costly.

Figure 20:
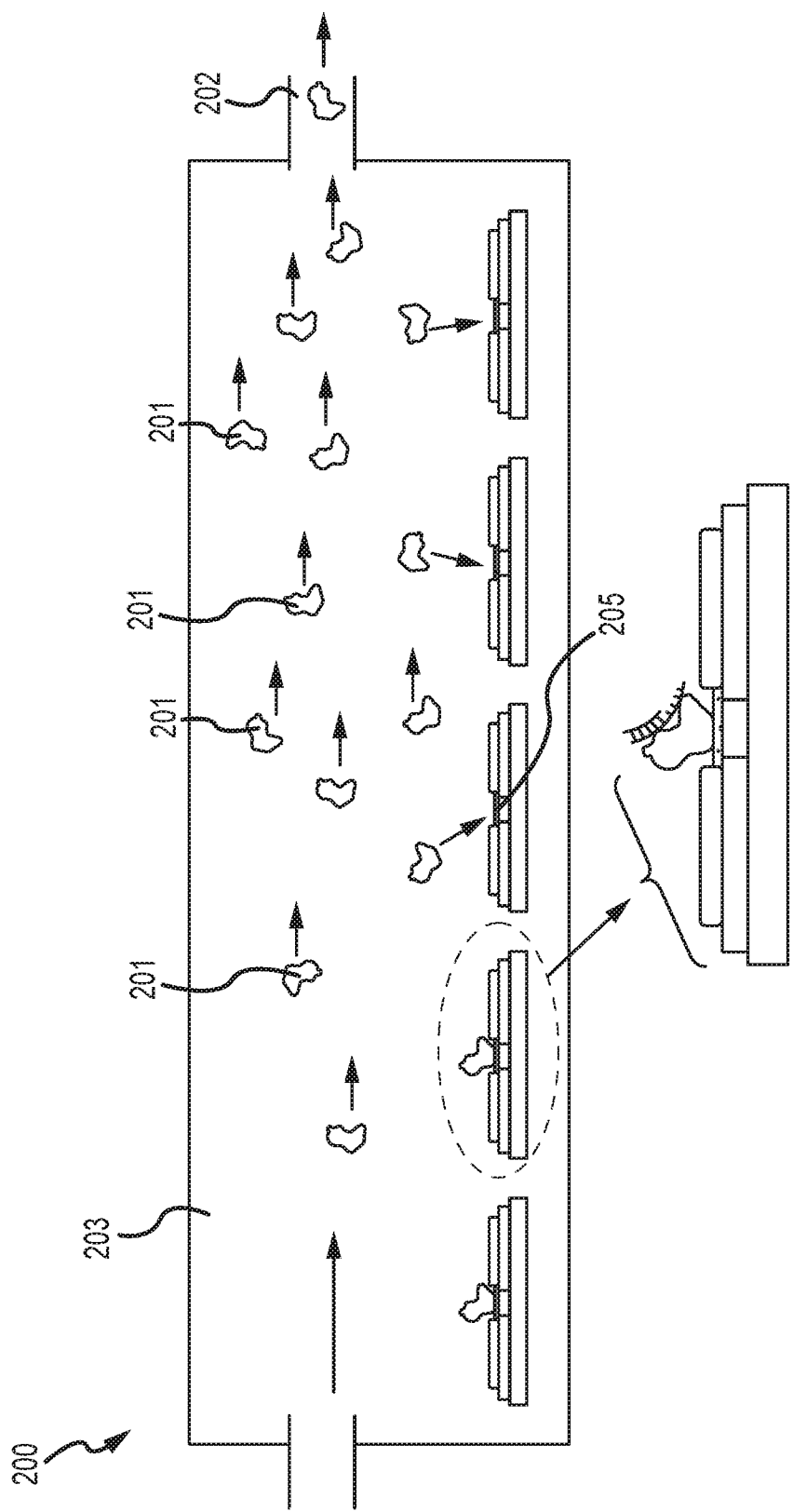
FIG. 20 illustrates an embodiment of a microfluidic chamber into which enzyme or other biomolecules are supplied in a phosphate-buffered saline (PBS) or other liquid solutions. Individual single enzyme molecules are selectively attached with a high probability onto each of the size-limited, exposed TMD island regions (e.g., $MoS_2$ or $WS_2$ layer) on the massively parallel sensor array. The unused biomolecules which did not adhere to the TMD islands are washed away out of the fluidic chamber. The analytes to be detected such as nucleotides or proteins are then supplied into the chamber to attach to the enzyme polymerase to induce electrical signal pulse for sequencing analysis.

FIG. 20 schematically illustrates operation of a microfluidic chamber wherein enzyme or other biomolecules are attached onto each TMD-containing molecular sensor device arranged in a massively parallel configuration. FIG. 20 illustrates a microfluidic reaction chamber 200 that is used to seed and attach biomolecules. In brief, this reaction chamber allows floating biomolecules 201 to be attached onto the exposed TMD islands, with unused biomolecules washed away through the chamber exit 202. In this operation, a phosphate-buffered saline (PBS) type aqueous solution 203 (or other solutions) containing enzymes or other biomolecules is supplied to a microfluidic reaction chamber 200. Individual single enzyme molecules are selectively attached with a high probability onto each of the size-limited, exposed TMD island regions 205 on the massive parallel sensor array. The probability of a single molecule attachment onto each TMD island is high because of the size-limited island configuration of the TMD, which is further enhanced because of the artificially and intentionally added, very large number of defects and more active binding sites such as the edge sites in nano-ribbons or in nanoporous layer TMD. In some embodiments, the success ratio of a single molecule adhesion to the available TMD island bridge locations is at least 30%, preferably at least 60%, and even more preferably at least 80%.

The unused biomolecules which did not adhere to the TMD islands are washed away out of the fluidic chamber. The analytes to be detected, such as nucleotides, DNA segments, or proteins, are then supplied into the chamber to attach to the enzyme polymerase to induce electrical signal pulse for biomolecule identification or DNA sequencing analysis.

Figure 21:
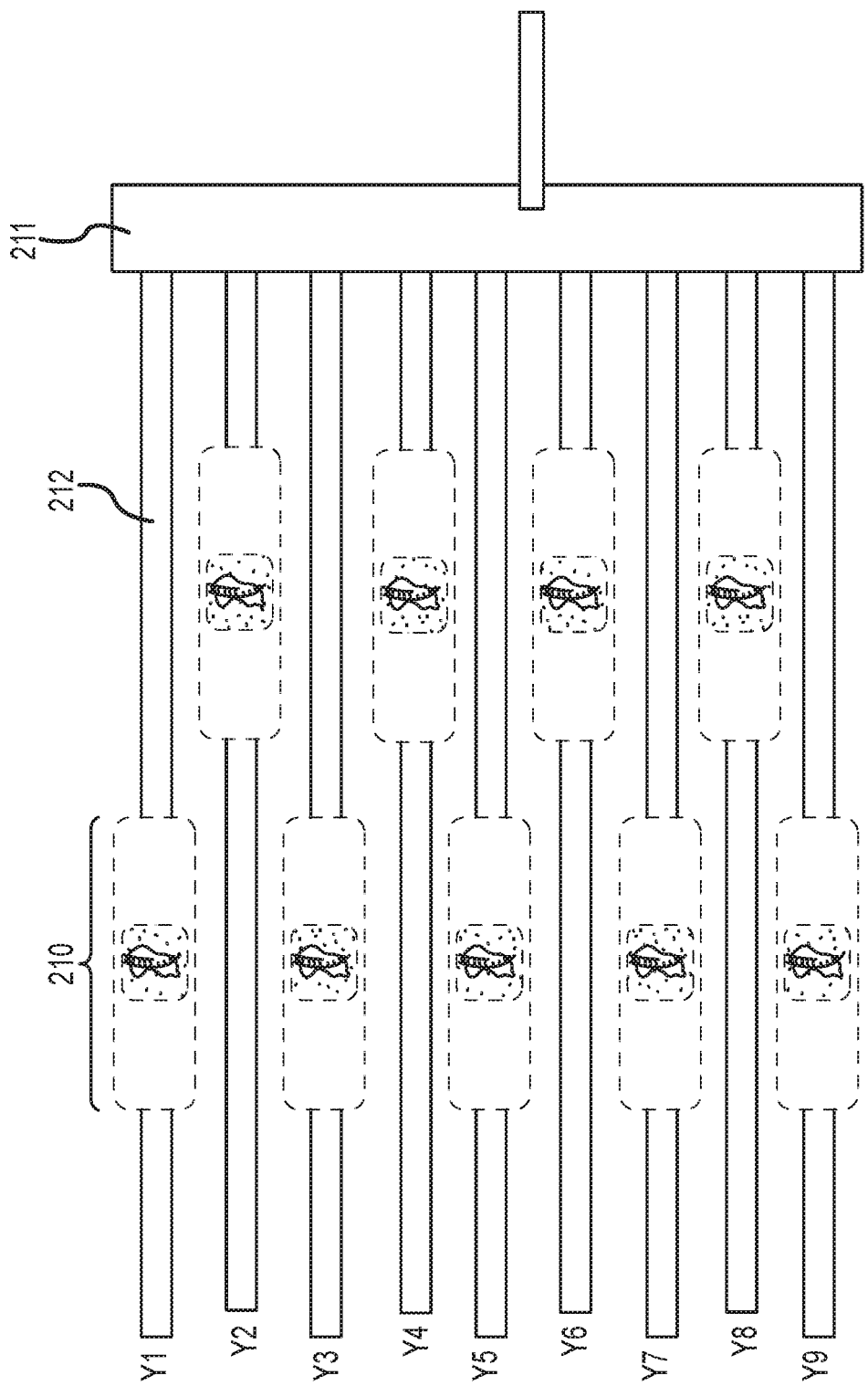
FIG. 21 illustrates an exemplary sequential interrogation of electrodes from the TMD-containing enzyme polymerase molecular sensor (e.g., with $MoS_2$ or $WS_2$ layer) for DNA or genome sequencing by using a common lead wire on one side of the array.

Electrical connections for many parallel devices may be complex and take up device surface real estate space. One way of reducing the complexity and analysis time is to utilize a sequential interrogation of electrodes from the TMD-containing enzyme polymerase molecular sensor by using a common lead wire on one side of the array, as illustrated in FIG. 21, by shorting one side of all lead wires and taking turns with left side electrical lead wires one at a time, e.g., every millisecond, as shown in FIG. 21. This method has an advantage of requiring less electronic measurement complications of handling many thousands of parallel signals all at once.

FIG. 21 illustrates an embodiment of a TMD-containing enzyme polymerase molecular sensor for label-free detection or nucleotide detachment. A sequential interrogation of electrodes is applied from the TMD-containing enzyme polymerase molecular sensor 210 (e.g., with $MoS_2$ or $WS_2$ layer) for DNA or genome sequencing by using a common lead wire 211 on one side of the array. Au lead wires 212 are surface insulated or coated to prevent protein adhesion. All of the right side electrodes are connected as a common lead wire, whereas the left side electrodes are interrogated one at a time, sequentially.

Even larger data can be obtained if the sensor device structure, such as exemplified in FIG. 19 or FIG. 21, is stacked in three dimension as shown in FIGS. 22A-22B, with accompanying microfluidic chambers for each stack (FIG. 22A) or using one or more common microfluidic chambers (FIG. 22B). FIGS. 22A-22B illustrate a three-dimensional array of molecular electronics genome-sequencing platform comprising TMD-based enzyme polymerase structure, e.g., with MoS2 or WS2 layers. An electrically insulating top coating (not shown) such as a polymer or an oxide layer (e.g., aluminum oxide, Si oxide, etc) is applied except in the exposed TMD region having an enzyme polymerase structure for nucleotide attachment. In some embodiments, there are 10 to 1,000 layers with each layer having, e.g., 100 to ~10,000 devices in individualized microfluidic chambers with PBS solution and nucleotide control arrangements and an electronic sensing array. FIG. 22A illustrates an exemplary embodiment of one common microfluidic chamber 220 containing 10-1,000 layers, with each layer having, e.g., 100 to ~10,000 devices. Each device layer has a multitude of molecular sensors 211. In such 3D configurations, at least one thousand to one million devices could be operated simultaneously for extremely rapid DNA or genome sequencing. For example, an electrically insulating top coating (not shown in FIGS. 22A-22B), such as a polymer or oxide coating (e.g. $Al_2O_3$, $SiO_2$, etc.), is applied over the surface except for the exposed TMD regions having the enzyme polymerase for nucleotide attachment. As illustrated in FIG. 22A, each 2D molecular electronics genome-sequencing device array is separately packaged into an individual microfluidic system 212, with each of the microfluidic layers stacked into a 3D configuration. In FIG. 22B, 2D molecular electronics genome-sequencing device arrays are stacked into 3D configurations but are housed in a single microfluidic system 213. The total number of molecular sensors can be at least 1,000, and can be as many as 1 million or more for massive parallel genome sequencing analysis.

When the sequencing device is not in use or being delivered or stored, it is important to make sure that the chamber is thoroughly washed and dried with a clean gas so that an adhesion or adsorption of unwanted gas molecules, dirt or dust in the form of nanoparticles and/or microparticles, is minimized. The sequencing device when not in use is desirably evacuated using a vacuum pump and back-filled with an inert gas so as to minimize the presence of unwanted gas molecules or dirt particles.

Figure 23:
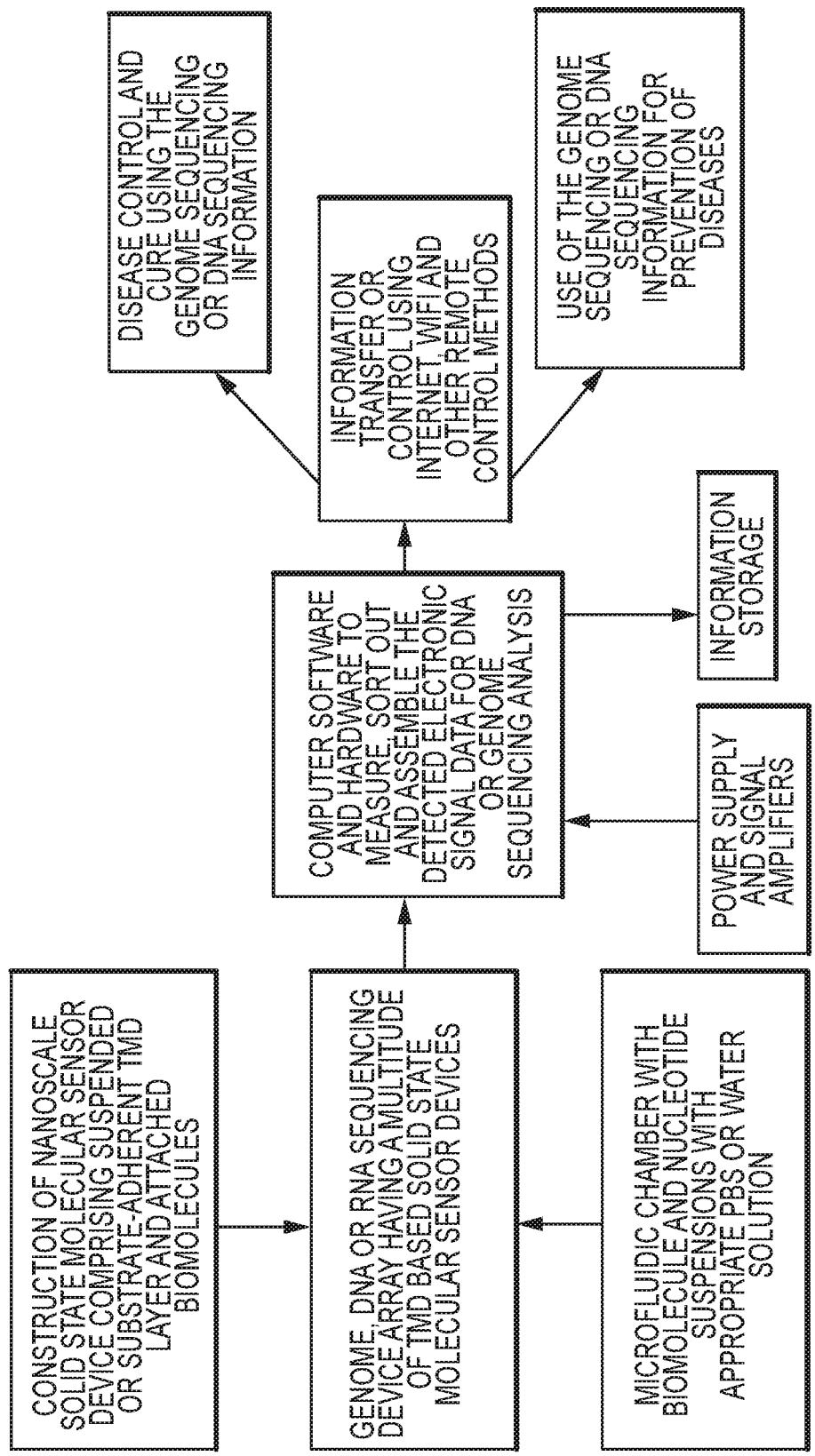
FIG. 23 illustrates a block diagram flowchart of DNA or genome sequencing system comprising TMD such as $MoS_2$ or $WS_2$ and enzyme polymerase sensor array, microfluidic structures, signal detection electronic circuits and associated devices, data analysis, storage or transmission devices, as well as applications of the sequencing devices for control, cure or prevention of diseases.

The overall genome or DNA sequencing system is described in FIG. 23 as a block flow diagram. Appropriate data analysis and storage software, computer systems (and Wi-Fi capability if desired) are incorporated, and microfluidic system is connected to the massively parallel electronic detection device array using the combined structure of TMD and single biomolecule enzyme polymerase, as well as coupling agents together with nucleotides to be sequenced. Instead of the desktop style units, portable or wearable units with information transfer or control via internet, Wi-Fi, cell phone or other methods can also be constructed and utilized. The high throughput DNA or genome sequencing device systems can be used for control, management and cure of diseases, as well as prediction and prevention of diseases from the genome sequence analysis for individual person.

The hierarchical process of nanofabrication, assembly and packaging of the device structures of FIG. 1A to FIG. 23 is desirably compatible with standard electronic device assembly such as c-MOS device fabrication and assembly. Parallel or areal processing steps, rather than individual processing steps, are thus preferred.

In some embodiments, the DNA or RNA molecular sensing device comprising modified or defective TMD structures such as MoS2 or WS2 is useful for partial or whole genome sequencing, or for diagnosis of diseases such as cancer. In some embodiments, the genome sequencing system can be operated as a desktop unit, a portable unit, or a wearable unit.

In some embodiments, the DNA or RNA molecular sensing device comprising modified or defective TMD structures such as $MoS_2$ or $WS_2$ is useful for partial or whole genome sequencing, or for diagnosis of diseases such as cancer. The genome sequencing system can be operated as a desktop unit, a portable unit or a wearable unit.

EXAMPLES

Example 1: Method of Electron Beam (E-Beam) Patterning of $MoS_2$ Layer using E-Beam Lithography $MoS_2$ 300 is suspended or on a substrate 304 (FIG. 2A). A portion is of the $MoS_2$ is subjected to an E-Beam 302. Resist is developed for nanopatterning (FIG. 2A). Chemical etch or Reactive Ion Etching is used to pattern the $MoS_2$ (FIG. 2A). The resist is removed to pattern the $MoS_2$ (FIG. 2A).

Example 2: Method of Nanoimprint Patterning of $MoS_2$ Layer $MoS_2$ 406 is suspended or on a substrate and resist material is applied to the $MoS_2$ (FIG. 2B). A mold 400 is applied to nanoimprint the resist material 404 on the $MoS_2$ layer (FIG. 2B). The mold is then released and reactive ion etching is applied to the resist material to form a nanopattern (FIG. 2B). Chemical etching or reactive ion etching is then used to pattern the $MoS_2$ (FIG. 2B). The resist material is then removed to reveal the patterned $MoS_2$ (FIG. 2B).

Example 3: Method of Synthesizing a Molecular Bridge of DNA or RNA Sensor Comprising Size-Limited $MoS_2$ Islands using Protective, Size-Limiting Dielectric Coating A $MoS_2$ (or TMD transition metal dichalcogenide) layer 36 is suspended over a conducting electrode pair 35 (Au, Pt, Ag, Pd, Rh, or their alloys, etc for signal detection) with a nanogap of e.g., 2-20 nm (FIG. 3B). The suspended $MoS_2$ has a regular or narrow-ribbon configuration or it is intentionally made defective (FIG. 3B). If necessary, the $MoS_2$ layer is patterned using an E-Beam or nanoimprinting (FIG. 3B). A protective, size-limiting dielectric coating 38 (e.g., polymer layer like PMMA or ceramic layer like $SiO_2$) is added (FIG. 3C). The $MoS_2$ is now size limited (e.g., 2-20 nm) for preferably a single biomolecule (e.g., polymerase enzyme) attachment (FIG. 3C). The Molecular bridge solid state sensor or $MoS_2$ island can be used for genome or DNA sequencing via detection of change of current pulse or other signals upon attaching or detaching of nucleotide or other biomolecules (FIG. 3D).

Example 4: Method of Synthesizing a Molecular Bridge of a DNA or RNA Sensor Comprising Size-Limited $MoS_2$ Islands using an Intentionally Damaged TND Region Like $MoS_2$ or $WS_2$ A $MoS_2$ (or TMD transition metal dichalcogenide) layer 56A is suspended over a conducting electrode pair 55 (Au, Pt, Ag, Pd, Rh, or their alloys, etc for signal detection) with a nanogap of e.g., 2-20 nm (FIG. 5B). The suspended $MoS_2$ layer 56A (or transition metal dichalcogenide layer in general), has a regular structure or defective MoS2 (FIG. 5B). An intentionally damaged TND region like $MoS_2$ or $WS_2$ is applied 56B (FIG. 5C). The TND region can be processed by doping with ion implantation or by bombardment with electrons or other radiation, which converts it to an insulator or very high resistivity region to function as an effective mask to enable a single biomolecule (e.g., polymerase enzyme) attachment (FIG. 5D). The molecular bridge solid state sensor or $MoS_2$ island can be used for genome or DNA sequencing via detection of change of current pulse or other signals upon attaching or detaching of nucleotide or other biomolecules (FIG. 5D).

Example 5: Method of Synthesizing a Molecular Bridge of DNA or RNA Sensor using a Suspended TMD Bridge A suspended TMD bridge 66A is attached or affixed by van der Waals forces and a dielectric coating (FIG. 6A). A single enzyme molecule 61 (e.g., DNA or RNA polymerase) is attached onto the size limited TMD bridge 66A (FIG. 6A). A nucleotide monomer 65 is detected upon attachment to the DNA strand 63 due to a change in current that results from attachment (FIG. 6A).

Example 6: Method of Synthesizing a Molecular Bridge of DNA or RNA Sensor using a Substrate-Adhered $MoS_2$ Bridge A $MoS_2$ layer 66B is substrate-adhered to the dielectric coating (FIG. 6B). A molecular bridge sensor with the TMD layer is affixed onto a dielectric substrate via van der Waals forces and a dielectric coating (FIG. 6B). A single enzyme molecule 61 (e.g., DNA or RNA polymerase) is attached onto the sized-limited TMD bridge (FIG. 6B). A nucleotide monomer 65 is detected upon attachment to the DNA strand due to a change in current that results from attachment (FIG. 6B).

Example 7: Method of Synthesizing a Molecular Bridge of DNA or RNA Sensor by Connecting an Enzyme to a Suspended TMD Bridge via a Functionalization Group An enzyme molecule 74 (e.g. DNA or RNA polymerase) is linked to a suspended TMD bridge 76 via a functionalizing group 71 (FIG. 7A). A nucleotide monomer 73 is detected upon attachment of the monomer to the DNA strand 72 through a change in current (FIG. 7A).

Example 8: Method of Synthesizing a Molecular Bridge of DNA or RNA Sensor by Connecting an Enzyme to a Substrate-Adhered TMD Bridge via a Functionalization Group An enzyme molecule 74 (e.g. DNA or RNA polymerase) is linked to a substrate-adhered TMD bridge 78 via a functionalization group 71 (FIG. 7B). A nucleotide monomer 73 is detected upon attachment of the monomer to the DNA strand 72 through a change in current (FIG. 7B).

Example 9: Method of Producing Hydrophilic-Enabled TMS Bridge Surface Structures A hydrophilic region is patterned or synthesized as a less perfect crystals 200 (e.g., ~3-20 um width) (FIG. 10A). Alternatively, a composite configuration of a mix of hydrophilic and hydrophobic regions 202 can be produced (FIG. 10B). A TMD 204 (e.g., preferably defective or nanoporous (like MoS2 or WS2) sheet is masked by dielectric (e.g., PMMA or adhesion-impeding polymer layer) to prevent biomolecule attachment (FIGS. 10A and 10B). Conducting electrodes and lead wires 206 (Au, Pt, Ag, Pd, Rh, or their alloys) are used for signal detection (FIGS. 10A and 10B).

Example 10: Method of Producing a Nanopatterned TMD Bridge using a Diblock Copolymer Mask A TMD like $MoS_2$ or $WS_2$ layer 130 is synthesized on metal foil 139 (e.g., by exfoliation, CVD or sulfurization of metal film) (FIG. 13A). After the metal is etched away, the TMD layer is transferred onto a device surface, e.g., nano-gapped, Au, Pd, or Pt electrode pair on $SiO_2$ 133 (or $SiO_2$-coated Si substrate), to place the TMD layer as a suspended bridge (FIG. 13B). TMD is covered by a thin layer of evaporated $SiO_2$ 134 and a thin film of spin-coated block-copolymer PS-b-P4VP 135 (FIG. 13C). The PS-b-P4VP block copolymer 135 film is annealed and developed into a nanoscale two-phase structure, leaving the porous PS matrix 136 as the template for subsequent patterning (FIG. 13D). Fluoride-based reactive ion etching (RIE) is used to penetrate and pattern the $SiO_2$ oxide layer, partially degrading the PS film, and forming the hard mask hole pattern 137 out of the thin $SiO_2$ (FIG. 13E). The TMD layer in the exposed hole area is etched away by $O_2$ plasma and then $SiO_2$ is removed (FIG. 13F). The nanoporous TMD on $SiO_2$ 138 is obtained (FIG. 13F), which is then patterned into a limited size island TMD by dielectric masking for single molecule (e.g., enzyme) attachment.

Example 11: Method of Producing a Nanopatterned TMD Bridge using an Anodized Aluminum Oxide (AAO) Membrane A TMD like $MoS_2$ or $WS_2$ layer 140 is synthesized on metal foil (e.g., by exfoliation, CVD, or sulfurization of metal film) (FIG. 13G). The $MoS_2$ layer is placed on a substrate 141 (FIG. 13H). An AAO nanohole membrane 142 is fabricated (FIG. 13I). The AAO is placed on the $MoS_2$ substrate 143 (FIG. 13J). RIE etching of $MoS_2$ is performed through the AAO holes 144 (FIG. 13K). A nanopatterned $MoS_2$ 145 is created on the substrate after AAO mask removal (FIG. 13L).

Example 12: Method of Producing a Nanoporous TMD Bridge using an Incompletely Deposited Thin Film Mask A thin TMD material like $MoS_2$ or $WS_2$ layer is synthesized by exfoliation, chemical vapor deposition (CVD), or sulfurization of metal film and placed on a substrate Support (sequencing structure base, or split substrates for $MoS_2$ suspension. The $MoS_2$ layer is deposited either by chemical vapor deposition (CVD) or by a transfer of pre-made $MoS_2$ layer floating in aqueous or alcohol-containing solution onto a substrate by lifting up and drying. A thin film mask layer is then deposited on the top surface of $MoS_2$, with a mask layer thickness of less than 5 nm, in an incomplete manner so that some nano regions are still not completely filled and nano-pinholes are present. The thin film is deposited by sputtering (other methods of deposition include evaporation, pulsed laser deposition or chemical deposition). The material for the thin film mask is selected from a ceramic layer such as $SiO_2$ or a sputter depositable polymer such as polytetrafluoroethylene (PTFE) type polymer. The use of metallic thin film mask can also be used.

A relatively short period deposition of the thin film layer is performed so as to produce pinhole-containing, incomplete thin (less than 5 nm thick) film, with the pinhole size in the range of 0.5-5 nm average diameter, and a density of $10^5/cm^2$ or higher. An optional post-sputtering can also be applied to consolidate the pinholes to a more uniform sizes. In order to increase the pinhole type defects in sputter deposition, the thin film mask deposition is carried out preferentially at a lower temperature, preferably near or below room temperature.

The $MoS_2$ layer underneath the thin film mask is then etched away through the mask defects by using either plasma etching (e.g., oxygen, CF4, SF6, or Ar plasma) or ion beam etching method. Chemical etching with an acid, e.g., selected from $H_2SO_4$, $HNO_3$, HCl or their mixtures can also be utilized for $MoS_2$ etching.

Once the nano-pinhole defects are prepared in the $MoS_2$, the mask material is removed by selective chemical etching or plasma etching. The $SiO_2$ type masks are readily removed by a BOE (buffered oxide etch) solution etching having a 6:1 volume ratio of 40% $NH_4F$ in water to 49% HF. The mask layer can also be etched away by plasma etching or ion beam etching. If NaCl or other salt type material is sputter deposited and employed as the mask layer, it can be dissolved away by water or solvents. Polymer mask films can be removed by solvent or by plasma etching.

The nano-pinhole defective $MoS_2$ (or defective TMD materials in general) created by using such a thin film mask approach can be utilized for genome sequencing if they are prepared directly on $MoS_2$ already mounted on a support (sequencing structure base, or split substrates for $MoS_2$ suspension) by micro- or nano-patterning to have a limited-size bridge to enable a single molecule polymerase attachment. This is followed by nucleotide attachment analysis.

Alternatively, the defective $MoS_2$ (or defective TMD materials) created by using such a thin film mask approach on a general substrate or dissolvable substrate can be released from the substrate by etching away, floating the $MoS_2$ in a aqueous or alcohol-containing solution, picking up by the genome sequencing base structure and micro patterning into desired geometry.

A dielectric masking layer is placed on the defective $MoS_2$ (or defective TMD materials). The defective $MoS_2$ is created by using a thin film mask approach surface with a size-limited opening. This allows only a single enzyme biomolecule to attach onto the exposed $MoS_2$ surface in a microfluidic system into which the DNA or genome sequencing structure is inserted. An electronic measurement and computer analysis are performed on attachment or detachment of a nucleotide monomer, a protein, a DNA segment, or other biomolecular component onto the enzyme polymerase molecule one at a time, which is then monitored to measure an electrical signal pulse and determine the specific nature of the nucleotide or biomolecules being attached.

The embodiments and examples described above are only meant for exemplary purposes and are not meant to limit the scope of any of the embodiments described herein. Any equivalent modification or variation according to the spirit of any of the embodiments disclosed herein is to be also included within the scope of any of the embodiments disclosed herein.

What is claimed is:

1. A device to characterize a biomolecule, comprising:
an array of conducting electrode pairs, each pair of electrodes comprising a source and a drain electrode arrangement separated by a nanogap, the electrode array deposited and patterned on a dielectric substrate;

at least one transition metal dichalcogenide (TMD) layer disposed on each pair of electrodes, wherein the TMD layer connects each source and drain electrode within each pair, and bridges each nanogap of each pair of electrodes;

a dielectric masking layer disposed on the TMD layer and comprising an aperture in the dielectric masking layer to expose a portion of the TMD region, wherein the aperture is sized to allow one and only one biomolecule to attach to the exposed TMD region through the aperture; and a single enzyme molecule connected to the exposed TMD region via an attachment consisting of a functional group pair such that only one enzyme molecule is present within each of the apertures.

2. The device of claim 1, wherein the enzyme molecule comprises a polymerase enzyme.

3. The device of claim 1, further comprising a microfluidic system in fluid combination with the sequencing device.

4. The device of claim 1, wherein the at least one TMD layer comprises $MoS_2$, $WS_2$, $TiS_2$, $ZrS_2$, $HfS_2$, $VS_2$, $NbS_2$, $TaS_2$, $TcS_2$, $ReS_2$, $CoS_2$, $RhS_2$, $IrS_2$, $NiS_2$, $PdS_2$, $PtS_2$, or any of their modifications or combinations, including modified stoichiometry of sulfur contents having $MX_{(2-x)}$ or $MX_{(2+x)}$, wherein x is in the range of 0-1.0.

5. The device of claim 4, wherein the sulfur stoichiometry is altered to provide vacancy defects, interstitial defects, and aggregated defects so as to increase surface energy and enhance adhesion of the enzyme molecule to the exposed TMD region.

6. The device of claim 1, wherein the at least one TMD layer comprises $MoSe_2$, $WSe_2$, $TiSe_2$, $ZrTe_2$, $HfTe_2$, $VTe_2$, $NbTe_2$, $TaTe_2$, $TcTe_2$, $ReTe_2$, $CoTe_2$, $RhTe_2$, $IrTe_2$, $NiTe_2$, $PdTe_2$, $PtTe_2$, or any of their modifications or combinations, including modified stoichiometry of selenium contents having $MX_{(2-x)}$ or $MX_{(2+x)}$, wherein x is in the range of 0-1.0.

7. The device of claim 6, wherein the selenium stoichiometry is intentionally altered to provide vacancy defects, interstitial defects, and aggregated defects in order to increase surface energy of the TMD layer and enhance adhesion of the enzyme molecule to the exposed TMD region.

8. The device of claim 1, wherein the at least one TMD layer comprises $MoTe_2$, $WTe_2$, $TiTe_2$, $ZrTe_2$, $HfTe_2$, $VTe_2$, $NbTe_2$, $TaTe_2$, $TcTe_2$, $ReTe_2$, $CoTe_2$, $RhTe_2$, $IrTe_2$, $NiTe_2$, $PdTe_2$, $PtTe_2$, or any of their modifications or combinations, including modified stoichiometry of tellurium contents having $MX_{(2-x)}$ or $MX_{(2+x)}$, wherein x is in the range of 0-1.0.

9. The device of claim 8, wherein the tellurium stoichiometry is intentionally altered to provide vacancy defects, interstitial defects, and aggregated defects in order to increase surface energy of the TMD layer and enhance adhesion of the enzyme molecule to the exposed TMD region.

10. The device of claim 1, wherein the TMD layer comprises $(Mo_xW_yCo_z)S_2)$ or $(Hf_xW_yCo_z)Te_2$.

11. The device of claim 1, wherein the array of conducting electrode pairs comprise at least one of Au, Pt, Ag, Pd, Rh, or their alloys.

12. The device of claim 1, wherein the nanogap is about 2 nm to about 20 nm in length.

13. The device of claim 1, wherein the TMD layer comprises a defective TMD layer.

14. The device of claim 13, wherein the defective TMD layer comprises a linear nano-ribbon parallel array, a patterned shape nano-ribbon array, strained lattice defects, vacancies, interstitial defects, dislocation defects, foreign atom implanted defects, or nanoporous defects.

15. The device of claim 13, wherein the defective TMD layer comprises strained lattice defects, vacancies, interstitial defects, dislocation defects or foreign atom implanted defects with a defect density of at least about $10^5/cm^2$.

16. The device of claim 13, wherein the defective TMD layer comprises nanoporous defects having an equivalent diameter of at least 2 nm with a defect density of at least $10^3/cm^2$.

17. The device of claim 13, wherein the defective TMD layer has a bandgap opened to a value of at least 0.2 eV.

18. The device of claim 1, wherein the functional group pair is a streptavidin biotin pair, an antigen-antibody interaction, bifunctional ligands using mercaptocarbonic acids [$HS-(CH_2)n-COOH$, n=1-15], peptide functional groups, a thiol-alkyne pair, a $COOH-NH_2$ functional group pair, a thiol-maleimide azide pair, a silanization linkage using mercaptosilane compounds, or a NHS (N-hydroxysuccinimide) ester-amine pair.

19. A device to characterize a biomolecule, comprising:
an array of conducting electrode pairs, each pair of electrodes comprising a source and a drain electrode arrangement separated by a nanogap, the electrode array deposited and patterned on a dielectric substrate;
a transition metal dichalcogenide (TMD) layer disposed on each pair of electrodes, wherein the TMD layer connects each source and drain electrode within each pair, and bridges each nanogap of each pair of electrodes;
a dielectric masking layer disposed on the TMD layer and comprising an aperture that defines an exposed TMD region; and
a single enzyme molecule connected to the exposed TMD region via an attachment consisting of a functional group pair such that only one enzyme molecule is connected through the aperture;
wherein the aperture is formed through the TMD layer to receive one and only one biomolecule.

20. The device of claim 19, wherein the TMD comprises a defective $MoS_2$.

21. The device of claim 19, wherein the aperture is lithographically formed.

22. The device of claim 19, wherein the aperture is formed to have a diameter of about 30 nm or less.

* * * * *